United States Patent
Finlay

(10) Patent No.: US 11,655,300 B2
(45) Date of Patent: May 23, 2023

(54) COLONY STIMULATING FACTOR 1 RECEPTOR (CSF1R) ANTIBODIES AND IMMUNOCONJUGATES THEREOF

(71) Applicant: ULTRAHUMAN TWELVE LIMITED, Sandwich (GB)

(72) Inventor: William James Jonathan Finlay, Sandwich (GB)

(73) Assignee: ULTRAHUMAN TWELVE LIMITED, Sandwich (GB)

( * ) Notice: Subject to any disclaimer, the term of this patent is extended or adjusted under 35 U.S.C. 154(b) by 0 days.

(21) Appl. No.: 16/976,196

(22) PCT Filed: Feb. 28, 2019

(86) PCT No.: PCT/EP2019/055077
§ 371 (c)(1),
(2) Date: Aug. 27, 2020

(87) PCT Pub. No.: WO2019/166596
PCT Pub. Date: Sep. 6, 2019

(65) Prior Publication Data
US 2021/0301026 A1  Sep. 30, 2021

(30) Foreign Application Priority Data

Feb. 28, 2018 (GB) ..................... 1803226
Jun. 21, 2018 (GB) ..................... 1810226
Nov. 22, 2018 (GB) ..................... 1819045

(51) Int. Cl.
*C07K 16/28* (2006.01)

(52) U.S. Cl.
CPC ...... *C07K 16/2866* (2013.01); *C07K 2317/21* (2013.01); *C07K 2317/565* (2013.01); *C07K 2317/567* (2013.01); *C07K 2317/92* (2013.01)

(58) Field of Classification Search
CPC ............ C07K 16/2866; C07K 2317/21; C07K 2317/565; C07K 2317/567; C07K 2317/92
See application file for complete search history.

(56) References Cited

FOREIGN PATENT DOCUMENTS

| WO | WO 2009/112245 A1 | 9/2009 |
| WO | WO 2011/123381 A1 | 10/2011 |
| WO | WO 2011/140249 A2 | 11/2011 |
| WO | WO 2015/028455 A1 | 3/2015 |

OTHER PUBLICATIONS

International Search Report and Written Opinion dated Apr. 11, 2019 for International Application No. PCT/EP2019/055077, 18 pages.
Papadopoulos, K. P. et al., "First-in-Human Study of AMG 820, a Monoclonal Anti-Colony-Stimulating Factor 1 Receptor Antibody, in Patients with Advanced Solid Tumors," Clin Cancer Res, 23(19):5703-5710 (2017); Published Online First Jun. 27, 2017; doi: 10.1158/1078-0432.CCR-16-3261.
Ries, C. H. et al., "Targeting Tumor-Associated Macrophages with Anti-CSF-1R Antibody Reveals a Strategy for Cancer Therapy," Cancer Cell, 25:846-859 (2014).
Townsend, S. et al., "Augmented binary substitution: single-pass CDR germ-lining and stabilization of therapeutic antibodies," PNAS, 112(50):15354-15359 (2015).
Zamarin, D. et al., "Upregulation of PD-L1 in tumor microenvironment is a resistance mechanism for oncolytic virus immunotherapy," Journal for ImmunoTherapy of Cancer, vol. 5, supplement 2:87, p. 202 (Nov. 1, 2017).

*Primary Examiner* — Robert S Landsman
(74) *Attorney, Agent, or Firm* — Cooley LLP; Ivor Elrifi

(57) ABSTRACT

Provided herein are antibody molecules that bind specifically to Colony Stimulating Factor 1 Receptor (CSF1R) and related nucleic acid molecules, vectors and host cells. Also provided herein are medical uses of such antibody molecules.

Figure 1:
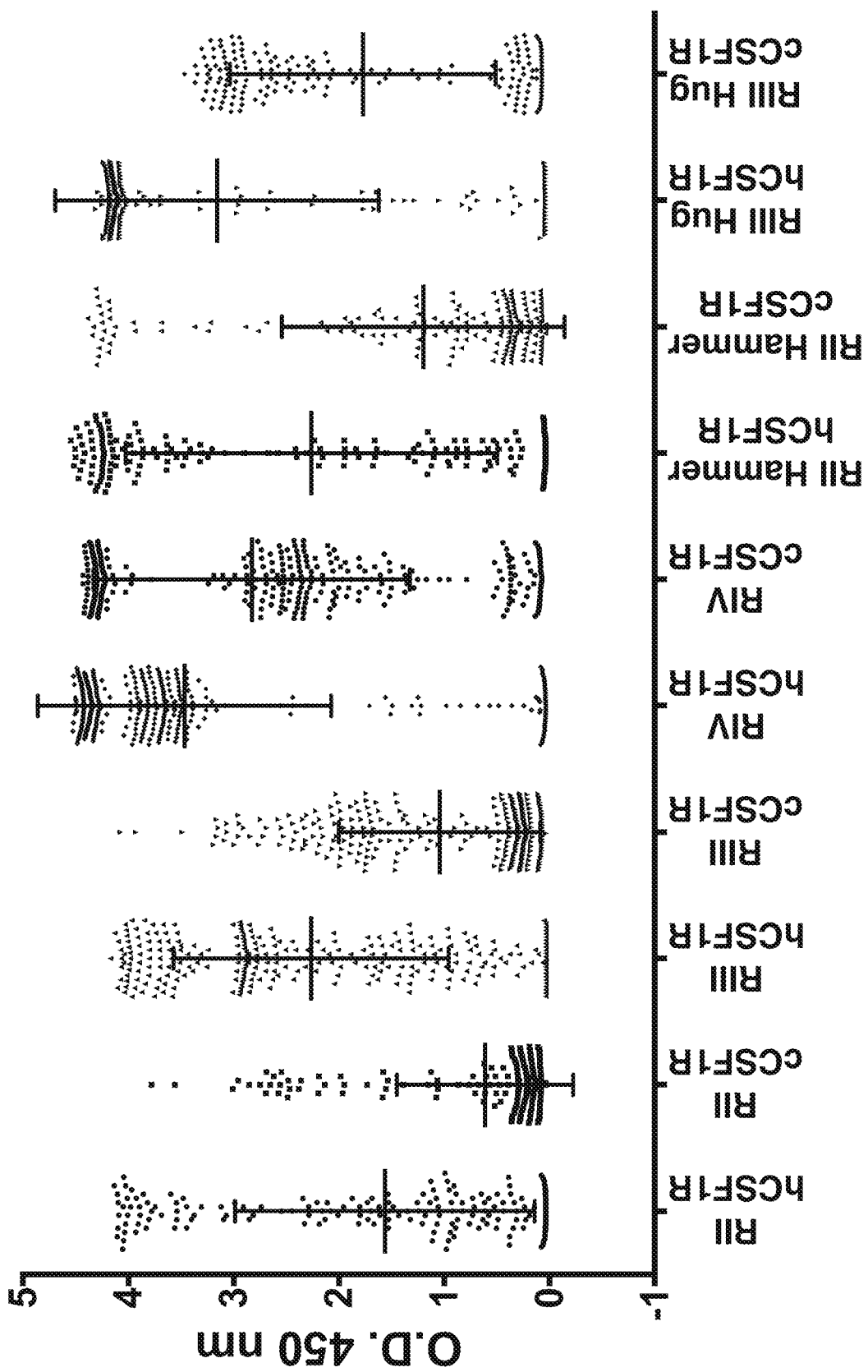

21 Claims, 22 Drawing Sheets
Specification includes a Sequence Listing.

COLONY STIMULATING FACTOR 1 RECEPTOR (CSF1R) ANTIBODIES AND IMMUNOCONJUGATES THEREOF

CROSS-REFERENCE TO RELATED APPLICATIONS

This application is a 35 U.S.C. § 371 national phase application of International Patent Application No. PCT/EP2019/055077, filed on Feb. 28, 2019, which claims the benefit of GB Patent Application No. 1819045.4, filed on Nov. 22, 2018, GB Patent Application No. 1810226.9, filed on Jun. 21, 2018, and GB Patent Application No. 1803226.8, filed on Feb. 28, 2018, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ULTL_001_03 US_SeqList_ST25.txt, date recorded: Aug. 27, 2020, file size ~158,269 bytes).

FIELD OF THE INVENTION

The invention relates to antibody molecules binding specifically to CSF1R (also known as Colony Stimulating Factor 1 Receptor, C-FMS, CD115, CSF-1R, CSFR, FIM2, FMS, HDLS, M-CSF-R) and medical uses thereof.

BACKGROUND OF THE INVENTION

CSF1R is a cell surface receptor that is a member of the immunoglobulin superfamily and is principally expressed on cells of mononuclear lineage, especially macrophages. CSF1R binds two known ligands, CSF1 (also known as M-CSF) and IL-34. The interaction of these ligands with CSF1R plays a direct role in the maturation, survival, proliferation and differentiation of mononuclear phagocytes, such as macrophages and monocytes.

While the role of CSF1R signalling in non-disease states is important for mononuclear cell regulation, it is also a key mechanism by which tumour cells recruit and maintain immunosuppressive tumour-associated macrophages (TAMs). Indeed, CSF1R has been shown to be highly expressed in TAMs in several cancers. In early stage and metastatic cancer the presence of intra-tumour CSF1R+ cells, including macrophages and neutrophils, correlates with poor survival. Hence, antagonistic anti-CSF1R mAbs have the potential to act as immunotherapeutic agents in cancer and immune disease settings, and to amplify the effectiveness of currently established therapies.

The majority of currently approved antibody therapeutics are derived from immunized rodents. Many of those antibodies have undergone a process known as "humanization", via the "grafting" of murine CDRs into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. Antibodies such as CSF1R inhibitors that target receptors on antigen-presenting immune cells, and whose pharmacological function is to stimulate immune responses, are at heightened risk of provoking anti-drug antibody responses. These anti-drug antibody responses in the patient can reduce drug half-life, potency and safety during clinical use. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized agonistic anti-CSF1R antibody would therefore have as many identical residues as possible in the v-domains to those found in both the frameworks and CDRs of well-characterized human germline sequences. Townsend et al. (2015; PNAS 112: 15354-15359) describe a method for generating antibodies in which CDRs derived from rat, rabbit and mouse antibodies were grafted into preferred human frameworks and then subjected to a human germ-lining approach termed "Augmented Binary Substitution". Although the approach demonstrated a fundamental plasticity in the original antibody paratopes, even when an investigator is in possession of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently inefficient, requiring an extra stage of modification of the starting antibody sequence. In addition, it cannot currently be accurately predicted what modifications in distal positions of the protein sequence of an individual v-domain, or even on the partner v-domain, might facilitate the removal of risk motifs while maintaining antigen binding affinity and specificity.

CDR germ-lining and development quality optimisation is thus a complex, multifactorial problem, as multiple functional properties of the molecule should preferably be maintained or improved, including in this instance: target binding specificity, CSF1R/CSF1 signalling antagonism, affinity to CSF1R from both human and animal test species (e.g. cynomolgus monkey, also known as the crab-eating macaque, i.e. *Macaca fascicularis*, and/or Rhesus monkey, i.e. *Macaca mulatta*) should be as similar as possible to facilitate highly accurate preclinical safety testing, v-domain biophysical stability and/or IgG expression yield should be optimal for manufacturing purposes. Antibody engineering studies have shown that mutation of even single residue positions in key CDRs can have dramatic negative effects on all of these desired molecular properties.

WO2011/140249A2 describes an antagonistic murine anti-CSF1R IgG molecule termed "0301", and also the preparation of humanized forms of 0301. Those humanized forms of 0301 were produced using classical humanization techniques, i.e. by grafting of Kabat-defined murine CDRs into human heavy and light chain framework sequences, with some of the human framework residues being potentially back-mutated to the correspondingly positioned 0301 murine residues. For reasons noted above, such humanized forms of 0301 described in WO2011/140249A2 are not ideal.

SUMMARY OF THE INVENTION

The present invention provides a number of anti-CSF1R antibodies and medical uses thereof.

According to one aspect of the invention, there is provided an antibody molecule which specifically binds to human CSF1R, and optionally also to cynomolgus monkey CSF1R, or an antigen-binding portion thereof, wherein the antibody molecule or antigen-binding portion comprises a heavy chain variable region with:

an HCDR1 having amino acids in sequence in the following order: G-Y/G-T-F-T/S-D/S-N/A/S/H/Y-Y/A-M/I-I/S (SEQ ID NO:13);

an HCDR2 having amino acids in sequence in the following order: M or a conservative substitution of M-G-D/G-I-N/I-P-Y/I-N/F-G-G/T-T/A-T/N-F/Y-N/A-Q-K-F-Q/K-G (SEQ ID NO:14); and an HCDR3 having amino acids in sequence in the following order: E or a conservative substitution of E (such as D)-D/G/H/S/T/P/V/N/I/Y-P/T/N/E/L/A/D/S-Y/K/R/M/P-F/D/S/T/E/W/M/Y/L/Q/K/G/A/I-S/E/G/R-N/E/Q/G/H/M-L/H/S/Y-Y/W-V-M-D-Y (SEQ ID NO:15).

In aspects of the invention, the HCDR1 of the antibody molecule or antigen-binding portion may exclude the sequences GYTFTDNYMI (SEQ ID NO:16; 0301 murine/humanized antibody HCDR1 disclosed in WO2011/140249A2), DINPYNGGTTFNQKFKG (SEQ ID NO:17; 0301 murine/humanized antibody HCDR2 disclosed in WO2011/140249A2), and/or the HCDR3 of the antibody molecule or antigen-binding portion may exclude the sequence ESPYFSNLYVMDY (SEQ ID NO:18; 0301 murine/humanized antibody HCDR3 disclosed in WO2011/140249A2).

The antibody molecule or antigen-binding portion may further comprise a light chain variable region with:

an LCDR1 having amino acids in sequence in the following order: R-A-S-Q-S-V-S/D/E-Y-D/E/Q-G-D/E-N-Y-L-N/A (SEQ ID NO:19);

an LCDR2 having amino acids in sequence in the following order: A/D-A-S-N/D-L/R-E/A-T (SEQ ID NO:20); and an LCDR3 having amino acids in sequence in the following order: Q/H/N-L/Q-S-N/S-E/Q/N-D/W-L-L/S-T (SEQ ID NO:21).

In aspects of the invention, the LCDR1 of the antibody molecule or antigen-binding portion may exclude the sequence KASQSVDYDGDNYMN (SEQ ID NO:22; 0301 murine/humanized antibody LCDR1 disclosed in WO2011/140249A2), and/or the LCDR2 of the antibody molecule or antigen-binding portion may exclude the sequence AASNLES (SEQ ID NO:23; 0301 murine/humanized antibody LCDR2 disclosed in WO2011/140249A2) and/or the LCDR3 of the antibody molecule or antigen-binding portion may exclude the sequence HLSNEDLST (SEQ ID NO:24; 0301 murine/humanized antibody LCDR3 disclosed in WO2011/140249A2).

In some aspects, disclosed herein is an anti-CSF1R antibody or an antigen-binding portion thereof, wherein the antibody comprises a heavy chain variable (VH) region and a light chain variable (VL) region, wherein (a) the VH region amino acid sequence comprises HCDR1 of GYTFSSYYMI (SEQ ID NO: 31), HCDR2 of MGDINPYNGGANYAQKFQG (SEQ ID NO: 32) and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38) and LCDR3 of QLSNEDLLT (SEQ ID NO: 39);

(b) the VH region amino acid sequence comprises HCDR1 of GYTFSSNYMI (SEQ ID NO:50), HCDR2 of MGDINPYNGGANYAQKFQG (SEQ ID NO: 32), HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60) and LCDR3 of QLSNEDLLT (SEQ ID NO: 39);

(c) the VH region amino acid sequence comprises HCDR1 of GYTFSSAYMI (SEQ ID NO:57), HCDR2 of MGDINPYNGGANYAQKFQG (SEQ ID NO:32) and HCDR3 of EGPYFSNLYVMDY (HCDR3; SEQ ID NO: 33); and the VL region amino acid sequence comprises LCDR1 of RASQSVSYEGENYLN (SEQ ID NO:37), LCDR2 of AASDRAT (SEQ ID NO:60) and LCDR3 of QLSNEDLLT (SEQ ID NO:39); or (d) the VH region amino acid sequence comprises HCDR1 of GYTFTSYYMI (SEQ ID NO:41), HCDR2 of MGDINPYNGGTTYAQKFQG (SEQ ID NO:42) and HCDR3 of EGPYFSNLYVMDY (SEQ ID NO:33); and the VL region amino acid sequence comprises LCDR1 of RASQSVSYEGENYLA (SEQ ID NO:40), LCDR2 of AASNLAT (SEQ ID NO:43) and LCDR3 of QLSNEDLLT (SEQ ID NO:39).

In some aspects, disclosed herein is an anti-CSF1R antibody or an antigen-binding portion thereof, wherein the antibody comprises a heavy chain variable (VH) region and a light chain variable (VL) region, wherein the VH region amino acid sequence comprises:
  (a) HCDR1 of SEQ ID NO: 31, SEQ ID NO: 50, SEQ ID NO: 57 or SEQ ID NO: 41;
  (b) HCDR2 of SEQ ID NO: 32 or SEQ ID NO: 42; and
  (c) HCDR3 of SEQ ID NO: 33; and the VL region amino acid sequence comprises:
  (a') LCDR1 of SEQ ID NO: 37 or SEQ ID NO: 40;
  (b') LCDR2 of SEQ ID NO: 38, SEQ ID NO: 60 or SEQ ID NO: 43; and
  (c') LCDR3 of SEQ ID NO: 39.

In some aspects, disclosed herein is an anti-CSF1R antibody or an antigen-binding portion thereof, wherein the antibody comprises a heavy chain variable (VH) region and a light chain variable (VL) region, wherein (a) the VH region amino acid sequence comprises or consists of SEQ ID NO:352 and the VL region amino acid sequence comprises or consists of SEQ ID NO:351;

(b) the VH region amino acid sequence comprises or consists of SEQ ID NO:354 and the VL region amino acid sequence comprises or consists of SEQ ID NO:353;

(c) the VH region amino acid sequence comprises or consists of SEQ ID NO:356 and the VL region amino acid sequence comprises or consists of SEQ ID NO:355; or (d) the VH region amino acid sequence comprises or consists of SEQ ID NO:358 and the VL region amino acid sequence comprises or consists of SEQ ID NO:357.

In some aspects, disclosed herein is an anti-CSF1R antibody or an antigen-binding portion thereof, wherein the antibody comprises a heavy chain variable (VH) region comprising HCDR1, HCDR2, and HCDR3 and a light chain variable (VL) region comprising LCDR1, LCDR2, and LCDR3, wherein (a) the HCDR1 comprises the amino acid sequence G-$X_1$-T-F-$X_2$-$X_3$-$X_4$-$X_5$-$X_6$-$X_7$, wherein $X_1$ is Y or G, $X_2$ is T or S, $X_3$ is D or S, $X_4$ is N, A, S, H or Y, $X_5$ is Y or A, $X_6$ is M or I, and $X_7$ is I or S (SEQ ID NO: 25);

(b) the HCDR2 comprises the amino acid sequence $X_1$-G-$X_2$-I-$X_3$-P-$X_4$-$X_5$-G-$X_6$-$X_7$-$X_8$-$X_9$-$X_{10}$-Q-K-F-$X_{11}$-G, wherein $X_1$ is M or a conservative substitution of M, $X_2$ is D or G, $X_3$ is N or I, $X_4$ is Y or I, $X_5$ is N or F, $X_6$ is G or T, $X_7$ is T or A, $X_8$ is T or N, $X_9$ is F or Y, $X_{10}$ is N or A, and $X_{11}$ is Q or K (SEQ ID NO: 26);

(c) the HCDR3 comprises the amino acid sequence $X_1$-$X_2$-$X_3$-$X_4$-$X_5$-$X_6$-$X_7$-$X_8$-$X_9$-V-M-D-Y, wherein $X_1$ is E or a conservative substitution of E, $X_2$ is D, G, H, S, T, P, V, N, I, or Y, $X_3$ is P, T, N, E, L, A, D, or S, $X_4$ is Y, K, R, M, or P, $X_5$ is F, D, S, T, E, W, M, Y, L, Q, K, G, A, or I, $X_6$ is S, E, G, or R, $X_7$ is N, E, Q, G, H, or M, $X_8$ is L, H, S, or Y, and $X_9$ is Y or W (SEQ ID NO: 27);

(d) the LCDR1 comprises the amino acid sequence R-A-S-Q-S-V-$X_1$-Y-$X_2$-G-$X_3$-N-Y-L-$X_4$, wherein $X_1$ is S, D, or E, $X_2$ is D, E, or Q, $X_3$ is D or E, and $X_4$ is N or A (SEQ ID NO: 28);

(e) the LCDR2 comprises the amino acid sequence $X_1$-A-S-$X_2$-$X_3$-$X_4$-T, wherein $X_1$ is A or D, $X_2$ is D or N, $X_3$ is L or R, and $X_4$ is E or A (SEQ ID NO: 29); and (f) the LCDR3 comprises the amino acid sequence $X_1$-$X_2$-S-$X_3$-$X_4$-$X_5$-L-$X_6$-T, wherein $X_1$ is Q, H, or N, $X_2$ is L or Q, $X_3$ is N or S, $X_4$ is E, Q, or N, $X_5$ is D or W, and $X_6$ is L or S (SEQ ID NO: 30).

In some aspects, the invention provides an anti-CSF1R antibody or an antigen-binding portion thereof, wherein the antibody comprises a heavy chain variable (VH) region and a light chain variable (VL) region, wherein (a) the VH region amino acid sequence comprises HCDR1 of GYTFSSYYMI (SEQ ID NO: 31), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYQGENYLA (SEQ ID NO: 34), LCDR2 of DASNRAT (SEQ ID NO: 35), and LCDR3 of QLSNQDLLT (SEQ ID NO: 36);

(b) the VH region amino acid sequence comprises HCDR1 of GYTFSSYYMI (SEQ ID NO: 31), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(c) the VH region amino acid sequence comprises HCDR1 of GYTFSSYYMI (SEQ ID NO: 31), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLA (SEQ ID NO:40), LCDR2 of AASNRAT (SEQ ID NO:38), and LCDR3 of QLSNQDLLT (SEQ ID NO: 36);

(d) the VH region amino acid sequence comprises HCDR1 of GYTFTSYYMI (SEQ ID NO:41), HCDR2 of MGDINPYNGGTTYAQKFQG (SEQ ID NO: 42), and HCDR3 of EGPYFSNLYVMDY (SEQ ID NO: 33); and the VL region amino acid sequence comprises LCDR1 of RASQSVSYEGENYLA (SEQ ID NO:40), LCDR2 of AASNLAT (SEQ ID NO:43), and LCDR3 of QLSNEDLLT (SEQ ID NO: 39);

(e) the VH region amino acid sequence comprises HCDR1 of GYTFTSYYMI (SEQ ID NO:41), HCDR2 of MGDINPYNGGANFAQKFQG (SEQ ID NO:44), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(f) the VH region amino acid sequence comprises HCDR1 of GYTFTSYYMI (SEQ ID NO:41), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(g) the VH region amino acid sequence comprises HCDR1 of GYTFSSYYMI (SEQ ID NO: 31), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVEYQGDNYLN (SEQ ID NO:45), LCDR2 of AASNRAT (SEQ ID NO:38), and LCDR3 of QLSNEDLLT (SEQ ID NO: 39);

(h) the VH region amino acid sequence comprises HCDR1 of GYTFTSYYII (SEQ ID NO:46), HCDR2 of MGDINPYNGGATYAQKFQG (SEQ ID NO:47), and HCDR3 of EPPYFSNLYVMDY (SEQ ID NO:48); and the VL region amino acid sequence comprises LCDR1 of RASQSVEYEGDNYLN (SEQ ID NO:49), LCDR2 of AASNRAT (SEQ ID NO:38), and LCDR3 of QLSNQDLLT (SEQ ID NO: 36);

(i) the VH region amino acid sequence comprises HCDR1 of GYTFSSNYMI (SEQ ID NO:50), HCDR2 of MGDINPYNGGATYNQKFQG (SEQ ID NO:51), and HCDR3 of EPPYFSNLYVMDY (SEQ ID NO:48); and the VL region amino acid sequence comprises LCDR1 of RASQSVEYEGENYLN (SEQ ID NO:52), LCDR2 of AASNRAT (SEQ ID NO:38), and LCDR3 of QLSNQDLLT (SEQ ID NO: 36);

(j) the VH region amino acid sequence comprises HCDR1 of GYTFSSYYMI (SEQ ID NO: 31), HCDR2 of MGDINPYNGGTTYAQKFQG (SEQ ID NO: 42), and HCDR3 of EGPYFSNLYVMDY (SEQ ID NO: 33); and the VL region amino acid sequence comprises LCDR1 of RASQSVEYQGENYLN (SEQ ID NO:53), LCDR2 of AASNRAT (SEQ ID NO:38), and LCDR3 of QLSNQDLLT (SEQ ID NO: 36);

(k) the VH region amino acid sequence comprises HCDR1 of GYTFTSNYII (SEQ ID NO:54), HCDR2 of MGDINPYNGGTNYAQKFQG (SEQ ID NO:55), and HCDR3 of EGPYFSNLYVMDY (SEQ ID NO: 33); and the VL region amino acid sequence comprises LCDR1 of RASQSVEYQGENYLN (SEQ ID NO:53), LCDR2 of AASNRAT (SEQ ID NO:38), and LCDR3 of QLSSEDLLT (SEQ ID NO:56);

(l) the VH region amino acid sequence comprises HCDR1 of GYTFSSNYMI (SEQ ID NO:50), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(m) the VH region amino acid sequence comprises HCDR1 of GYTFSSAYMI (SEQ ID NO:57), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(n) the VH region amino acid sequence comprises HCDR1 of GYTFSSSYMI (SEQ ID NO:58), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(o) the VH region amino acid sequence comprises HCDR1 of GYTFSSHYMI (SEQ ID NO:59), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(p) the VH region amino acid sequence comprises HCDR1 of GYTFSSNYMI (SEQ ID NO:50), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39);

(q) the VH region amino acid sequence comprises HCDR1 of GYTFSSAYMI (SEQ ID NO:57), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39);

(r) the VH region amino acid sequence comprises HCDR1 of GYTFSSSYMI (SEQ ID NO:58), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39); or (s) the VH region amino acid sequence comprises HCDR1 of GYTFSSHYMI (SEQ ID NO:59), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39).

Further provided herein is an anti-CSF1R antibody or an antigen-binding portion thereof, wherein the antibody comprises a heavy chain variable (VH) region and a light chain variable (VL) region, wherein the VH region amino acid sequence comprises SEQ ID NO:1, SEQ ID NO:2, SEQ ID NO:3; SEQ ID NO:4; SEQ ID NO:5; SEQ ID NO:6; SEQ ID NO:7; or SEQ ID NO:8; and the VL region amino acid sequence comprises SEQ ID NO:9; SEQ ID NO:10; SEQ ID NO:11 or SEQ ID NO:12.

Additionally provided herein is an anti-CSF1R antibody or an antigen-binding portion thereof, wherein the antibody comprises a heavy chain variable (VH) region and a light chain variable (VL) region, wherein (a) the VH region amino acid sequence comprises SEQ ID NO:1, and the VL region amino acid sequence comprises SEQ ID NO:9;

(b) the VH region amino acid sequence comprises SEQ ID NO:1, and the VL region amino acid sequence comprises SEQ ID NO:10;

(c) the VH region amino acid sequence comprises SEQ ID NO:1, and the VL region amino acid sequence comprises SEQ ID NO:11;

(d) the VH region amino acid sequence comprises SEQ ID NO:1, and the VL region amino acid sequence comprises SEQ ID NO:12;

(e) the VH region amino acid sequence comprises SEQ ID NO:2, and the VL region amino acid sequence comprises SEQ ID NO:9;

(f) the VH region amino acid sequence comprises SEQ ID NO:2, and the VL region amino acid sequence comprises SEQ ID NO:10;

(g) the VH region amino acid sequence comprises SEQ ID NO:2, and the VL region amino acid sequence comprises SEQ ID NO:11;

(h) the VH region amino acid sequence comprises SEQ ID NO:2, and the VL region amino acid sequence comprises SEQ ID NO:12;

(i) the VH region amino acid sequence comprises SEQ ID NO:3, and the VL region amino acid sequence comprises SEQ ID NO:9;

(j) the VH region amino acid sequence comprises SEQ ID NO:3, and the VL region amino acid sequence comprises SEQ ID NO:10;

(k) the VH region amino acid sequence comprises SEQ ID NO:3, and the VL region amino acid sequence comprises SEQ ID NO:11;

(l) the VH region amino acid sequence comprises SEQ ID NO:3, and the VL region amino acid sequence comprises SEQ ID NO:12;

(m) the VH region amino acid sequence comprises SEQ ID NO:4, and the VL region amino acid sequence comprises SEQ ID NO:9;

(n) the VH region amino acid sequence comprises SEQ ID NO:4, and the VL region amino acid sequence comprises SEQ ID NO:10;

(o) the VH region amino acid sequence comprises SEQ ID NO:4, and the VL region amino acid sequence comprises SEQ ID NO:11;

(p) the VH region amino acid sequence comprises SEQ ID NO:4, and the VL region amino acid sequence comprises SEQ ID NO:12;

(q) the VH region amino acid sequence comprises SEQ ID NO:5, and the VL region amino acid sequence comprises SEQ ID NO:9;

(r) the VH region amino acid sequence comprises SEQ ID NO:5, and the VL region amino acid sequence comprises SEQ ID NO:10;

(s) the VH region amino acid sequence comprises SEQ ID NO:5, and the VL region amino acid sequence comprises SEQ ID NO:11;

(t) the VH region amino acid sequence comprises SEQ ID NO:5, and the VL region amino acid sequence comprises SEQ ID NO:12;

(u) the VH region amino acid sequence comprises SEQ ID NO:6, and the VL region amino acid sequence comprises SEQ ID NO:9;

(v) the VH region amino acid sequence comprises SEQ ID NO:6, and the VL region amino acid sequence comprises SEQ ID NO:10;
(w) the VH region amino acid sequence comprises SEQ ID NO:6, and the VL region amino acid sequence comprises SEQ ID NO:11;
(x) the VH region amino acid sequence comprises SEQ ID NO:6, and the VL region amino acid sequence comprises SEQ ID NO:12;
(y) the VH region amino acid sequence comprises SEQ ID NO:7, and the VL region amino acid sequence comprises SEQ ID NO:9;
(z) the VH region amino acid sequence comprises SEQ ID NO:7, and the VL region amino acid sequence comprises SEQ ID NO:10;
(aa) the VH region amino acid sequence comprises SEQ ID NO:7, and the VL region amino acid sequence comprises SEQ ID NO:11;
(bb) the VH region amino acid sequence comprises SEQ ID NO:7, and the VL region amino acid sequence comprises SEQ ID NO:12;
(cc) the VH region amino acid sequence comprises SEQ ID NO:8, and the VL region amino acid sequence comprises SEQ ID NO:9;
(dd) the VH region amino acid sequence comprises SEQ ID NO:8, and the VL region amino acid sequence comprises SEQ ID NO:10;
(ee) the VH region amino acid sequence comprises SEQ ID NO:8, and the VL region amino acid sequence comprises SEQ ID NO:11; or
(ff) the VH region amino acid sequence comprises SEQ ID NO:8, and the VL region amino acid sequence comprises SEQ ID NO:12.

Also provided according to the invention is an immunoconjugate comprising the antibody molecule or antigen-binding portion thereof as defined herein linked, fused or conjugated to a therapeutic agent.

In another aspect the invention provides a nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-CSF1R antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

Further provided herein is an antibody molecule or antigen-binding portion thereof as defined herein, or the immunoconjugate as defined herein, or the nucleic acid molecule as defined herein, or the vector as defined herein, or the pharmaceutical composition as defined herein, for use as a medicament. Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an infectious disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The infectious disease may be selected in all aspects from the group consisting of: viral, bacterial, fungal or parasitic.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an infectious disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an infectious disease.

The invention also provides a method for treating or preventing an infectious disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The invention also provides a method of producing an antibody molecule which specifically binds to human CSF1R and optionally also to cynomolgus and monkey CSF1R, or an antigen-binding portion thereof, comprising the steps of:

(1) grafting anti-CSF1R CDRs from a non-human source into a human v-domain framework to produce a humanized anti-CSF1R antibody molecule or antigen-binding portion thereof;

(2) generating a library of clones of the humanized anti-CSF1R antibody molecule or antigen-binding portion thereof comprising one or more mutations in the CDRs;

(3) screening the library for binding to human CSF1R and optionally also to cynomolgus and monkey CSF1R;

(4) selecting clones from the screening step (3) having binding specificity to human CSF1R and optionally also to cynomolgus and rhesus monkey CSF1R; and (5) producing an antibody molecule which specifically binds to human CSF1R and optionally also to cynomolgus and rhesus monkey CSF1R, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

BRIEF DESCRIPTION OF THE FIGURES

FIG. 1. Direct binding ELISA of library-derived anti-CSF1R Fabs against human and cyno CSF1R-Fc proteins. Clones were derived from multiple phage selection branches where phage populations were selected on biotinylated human, or cynomolgus monkey CSF1R proteins in each round. Standard selections are numbered R2-R4. 'Hammer-Hug' rounds are numbered R2-H and R3-H. After each round of selection, library-derived clones (black circles) were screened as periplasmically-expressed Fab proteins, against both human (h) and cyno (c) CSF1R. Mean±SD values in each round are represented in black bars.

FIG. 2A-FIG. 2B. Analysis of CDR residue tolerance for mutation to germline. A plot of murine amino acid retention frequencies in the CDRs of the ELISA-positive population of 598 unique scFv clones is shown for $V_L$ (SEQ ID NOs: 22, 23 and 24) (FIG. 2A) and $V_H$ (SEQ ID NOs: 16, 17 and 18) (FIG. 2B) domains, respectively. Only those residues targeted for human/murine residue mutagenesis are plotted, other than in the HCDR3. CDR residues noted in parentheses on the X-axes were identical to those found in the human germlines used for grafting (IGKV3-11 and IGHV1-69). In both plots the dashed line in grey at 75% represents the cut-off for tolerance of murine residue replacement by human germline.

FIG. 3A-FIG. 3B. Direct titration ELISA for library-derived and designer IgG4(S228P) clones binding to human and cyno CSF1R-Fc proteins. mu0301, hu0301, library-derived and designer clones in human IgG4(S228P) format were titrated (in nM) in a direct binding ELISA against human (FIG. 3A) and cyno (FIG. 3B) CSF1R-Fc proteins.

FIG. 4. Epitope competition analysis of IgG4 proteins in Alphascreen. Anti-CSF1R IgG4(S228P) clones were applied in an epitope competition assay using Alphascreen technology. In this assay, library-derived (A) and designer (B) IgGs were analysed for their relative affinities and retention of the parental mu0301 epitope by competing for mu0301 IgG4(S228P) binding to human CSF1R protein, in solution. All clones analysed showed strong, concentration-dependent neutralisation of mu0301 binding to CSF1R.

FIG. 5A-FIG. 5B. Flow cytometric binding to human and rhesus CSF1R+ HEK-293 cells. mu0301, hu0301, lead library-derived and designer IgGs were examined for specific binding on HEK-293 cells expressing human (FIG. 5A) and rhesus (FIG. 5B) CSF1R. Concentration-dependent binding was observed against human CSF1R for all clones, with binding curves that overlap or improve over the hu0301 clone.

FIG. 6A-FIG. 6B. Direct titration ELISA for designer, deimmunized IgG4(S228P) clones binding to human and cyno CSF1R-Fc proteins. mu0301, hu0301, isotype and designer clones in human IgG4(S228P) format were titrated (in nM) in a direct binding ELISA against human (FIG. 6A) and cyno (FIG. 6B) CSF1R-Fc proteins.

FIG. 7. Flow cytometric binding to human CSF1R+ HEK-293 cells. mu0301, hu0301, isotype and designer clones in human IgG4(S228P) format were examined for specific binding on HEK-293 cells expressing human CSF1R. Concentration-dependent binding was observed against human CSF1R for all clones, with binding curves that overlap with the hu0301 clone.

FIG. 8. Development risk ELISAs. mu0301, hu0301, isotype and designer clones in human IgG4(S228P) format were examined for nonspecific binding to the negatively charged biomolecules insulin and double-stranded DNA (dsDNA). All lead clones demonstrated binding scores of 1.0, significantly lower than either of the negative control IgG1 Ustekinumab and Bevacizumab analogs. Strong off-target binding to human insulin or dsDNA, as observed for Bococizumab and Briakinumab analogues, has been shown to be a high-risk indicator of poor pharmacokinetics of therapeutic antibodies.

FIG. 9A-FIG. 9C. Effect of anti-CSF1R antibodies on primary human monocyte proliferation. hu0301, isotype and lead clones in human IgG4(S228P) format were examined for the potency of inhibition of human monocyte proliferation (under MCSF stimulation), using monocyte populations from 3 separate human donors. All clones examined were found to have fully overlapping curves across all 3 donors, indicating highly similar biological potency.

FIG. 10. Differential Scanning calorimetry (DSC) of IgGs. DSC assay data for the following antibodies in IgG4 (S228P) form: (mAb-1) hu0301, (mAb-2) MH5, (mAb-3) 30E06, (mAb-4) MH12, and (mAb-5) MH16.

FIG. 11A-FIG. 11E. Reverse Phase Chromatography analyses of tryptic peptides from IgGs before and after forced oxidation. Reverse phase chromatograms for antibodies in IgG4(S228P) form: hu0301 (FIG. 11A) exhibited 8 significant peptide changes post-oxidation. MH5 (FIG. 11B) exhibited 3, 30E06 (FIG. 11C) exhibited 4, MH12 (FIG. 11D) exhibited 4 and MH16 (FIG. 11E) exhibited 5. In each panel chromatograms before (—$H_2O_2$, upper) and after oxidation (+$H_2O_2$, lower) are shown. Arrows in each panel indicate peaks representing modified peptides (gained, reduced or lost after oxidation).

FIG. 12. HIC chromatograms of IgGs. A panel of clinical monoclonal antibodies (Adalimumab, Brentuximab, Cetuximab, Golimumab and Trastuzumab) and antibodies in IgG4 (S228P) form: (mAb-1) hu0301, (mAb-2) MH5, (mAb-3) 30E06, (mAb-4) MH12, and (mAb-5) MH16, were analysed by HIC. All antibodies eluted between 3.5 and 10.5 minutes (left to right).

DETAILED DESCRIPTION OF THE INVENTION

According to a first aspect of the invention, there is provided an antibody molecule which specifically binds to human CSF1R and optionally also to cynomolgus monkey CSF1R, or an antigen-binding portion thereof, wherein the antibody molecule or antigen-binding portion comprises a heavy chain variable region with:

an HCDR1 having amino acids in sequence in the following order: G-Y/G-T-F-T/S-D/S-N/A/S/H/Y-Y/A-M/I-I/S (SEQ ID NO:13);

an HCDR2 having amino acids in sequence in the following order: M or a conservative substitution of M-G-D/G-I-N/I-P-Y/I-N/F-G-G/T-T/A-T/N-F/Y-N/A-Q-K-F-Q/K-G (SEQ ID NO:14); and an HCDR3 having amino acids in sequence in the following order: E or a conservative substitution of E (such as D)-D/G/H/S/T/P/V/N/I/Y-P/T/N/E/L/A/D/S-Y/K/R/M/P-F/D/S/T/E/W/M/Y/L/Q/K/G/A/I-S/E/G/R-N/E/Q/G/H/M-L/H/S/Y-Y/W-V-M-D-Y (SEQ ID NO:15).

In some aspects an anti-CSF1R antibody or antigen-binding portion provided herein specifically binds to a CSF1R protein comprising or consisting of SEQ ID NO:365 or 366. In some aspects an anti-CSF1R antibody or antigen-binding portion provided herein specifically binds to a CSF1R protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:365 or 366.

In aspects of the invention, the HCDR1 of the antibody molecule or antigen-binding portion may exclude the sequences GYTFTDNYMI (SEQ ID NO:16; 0301 murine/humanized antibody HCDR1 disclosed in WO2011/140249A2), DINPYNGGTTFNQKFKG (SEQ ID NO:17; 0301 murine/humanized antibody HCDR2 disclosed in WO2011/140249A2), and/or the HCDR3 of the antibody molecule or antigen-binding portion may exclude the sequence ESPYFSNLYVMDY (SEQ ID NO:18; 0301 murine/humanized antibody HCDR3 disclosed in WO2011/140249A2).

The antibody molecule or antigen-binding portion may further comprise a light chain variable region with:

an LCDR1 having amino acids in sequence in the following order: R-A-S-Q-S-V-S/D/E-Y-D/E/Q-G-D/E-N-Y-L-N/A (SEQ ID NO:19);

an LCDR2 having amino acids in sequence in the following order: A/D-A-S-N/D-L/R-E/A-T (SEQ ID NO:20); and an LCDR3 having amino acids in sequence in the following order: Q/H/N-L/Q-S-N/S-E/Q/N-D/W-L-L/S-T (SEQ ID NO:21).

In aspects of the invention, the LCDR1 of the antibody molecule or antigen-binding portion may exclude the sequence KASQSVDYDGDNYMN (SEQ ID NO:22; 0301 murine/humanized antibody LCDR1 disclosed in WO2011/140249A2), and/or the LCDR2 of the antibody molecule or antigen-binding portion may exclude the sequence AASNLES (SEQ ID NO:23; 0301 murine/humanized antibody LCDR2 disclosed in WO2011/140249A2) and/or the LCDR3 of the antibody molecule or antigen-binding portion may exclude the sequence HLSNEDLST (SEQ ID NO:24; 0301 murine/humanized antibody LCDR3 disclosed in WO2011/140249A2).

In some aspects, disclosed herein is an anti-CSF1R antibody or an antigen-binding portion thereof, wherein the antibody comprises a heavy chain variable (VH) region comprising HCDR1, HCDR2, and HCDR3 and a light chain variable (VL) region comprising LCDR1, LCDR2, and LCDR3, wherein (a) the HCDR1 comprises the amino acid sequence G-$X_1$-T-F-$X_2$-$X_3$-$X_4$-$X_5$-$X_6$-$X_7$, wherein $X_1$ is Y or G, $X_2$ is T or S, $X_3$ is D or S, $X_4$ is N, A, S, H or Y, $X_5$ is Y or A, $X_6$ is M or I, and $X_7$ is I or S (SEQ ID NO: 25);

(b) the HCDR2 comprises the amino acid sequence $X_1$-G-$X_2$-I-$X_3$-P-$X_4$-$X_5$-G-$X_6$-$X_7$-$X_8$-$X_9$-$X_{10}$-Q-K-F-$X_{11}$-G, wherein $X_1$ is M or a conservative substitution of M, $X_2$ is D or G, $X_3$ is N or I, $X_4$ is Y or I, $X_5$ is N or F, $X_6$ is G or T, $X_7$ is T or A, $X_8$ is T or N, $X_9$ is F or Y, $X_{10}$ is N or A, and $X_{11}$ is Q or K (SEQ ID NO: 26);

(c) the HCDR3 comprises the amino acid sequence $X_1$-$X_2$-$X_3$-$X_4$-$X_5$-$X_6$-$X_7$-$X_8$-$X_9$-V-M-D-Y, wherein $X_1$ is E or a conservative substitution of E (for example, D), $X_2$ is D, G, H, S, T, P, V, N, I, or Y, $X_3$ is P, T, N, E, L, A, D, or S, $X_4$ is Y, K, R, M, or P, $X_5$ is F, D, S, T, E, W, M, Y, L, Q, K, G, A, or I, $X_6$ is S, E, G, or R, $X_7$ is N, E, Q, G, H, or M, $X_8$ is L, H, S, or Y, and $X_9$ is Y or W (SEQ ID NO: 27;

(d) the LCDR1 comprises the amino acid sequence R-A-S-Q-S-V-$X_1$-Y-$X_2$-G-$X_3$-N-Y-L-$X_4$, wherein $X_1$ is S, D, or E, $X_2$ is D, E, or Q, $X_3$ is D or E, and $X_4$ is N or A (SEQ ID NO: 28);

(e) the LCDR2 comprises the amino acid sequence $X_1$-A-S-$X_2$-$X_3$-$X_4$-T, wherein $X_1$ is A or D, $X_2$ is D or N, $X_3$ is L or R, and $X_4$ is E or A (SEQ ID NO: 29); and (f) the LCDR3 comprises the amino acid sequence $X_1$-$X_2$-S-$X_3$-$X_4$-$X_5$-L-$X_6$-T, wherein $X_1$ is Q, H, or N, $X_2$ is L or Q, $X_3$ is N or S, $X_4$ is E, Q, or N, $X_5$ is D or W, and $X_6$ is L or S (SEQ ID NO: 30).

In some aspects, disclosed herein is an anti-CSF1R antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:25, the HCDR2 is SEQ ID NO:26, the HCDR3 is SEQ ID NO:27, the LCDR1 is SEQ ID NO:28, the LCDR2 is SEQ ID NO:29 and the LCDR3 is SEQ ID NO:30, wherein the heavy chain FR1, FR2, FR3 and FR4 amino acid sequences are the heavy chain FR1, FR2, FR3 and FR4 amino acid sequences in SEQ ID NO: 105 (see Table 2) and wherein the light chain FR1, FR2, FR3 and FR4 amino acid sequences are the light chain FR1, FR2, FR3 and FR4 amino acid sequences in SEQ ID NO: 108 (see Table 2).

As elaborated herein, the present inventors have succeeded for the first time in generating a number of optimized anti-CSF1R antibody molecules using CDR sequences derived from the murine anti-CSF1R antibody 0301 disclosed in WO2011/140249A2. In embodiments of the present invention, these antibody molecules have been selected to have highly similar binding specificity and affinity to both human CSF1R as well as cynomolgus and rhesus monkey CSF1R (to facilitate maximally accurate primate toxicology and pk studies). Further refining of the optimized antibody molecules as described herein has provided improved binding to the human and cynomolgus monkey orthologues of CSF1R, improved potency in neutralisation of CSF1R signalling, improved variable domain stability, high expression yields, and/or reduced immunogenicity potential.

In some aspects, optimized anti-CSF1R antibody molecules of the present invention do not necessarily have the maximum number of human germline substitutions at corresponding murine CDR or other (such as framework) amino acid positions. As elaborated in the experimental section below, we have found that "maximally humanized"

antibody molecules are not necessary "maximally optimized" in terms of anti-CSF1R binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to CSF1R. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-Y/G-T-F-T/S-D/S-N/A/S/H/Y-Y/A-M/I-I (SEQ ID NO:61); the HCDR2 may have the amino acid sequence: M-G-D-I-N/I-P-Y-N/F-G-G/T-T/A-T/N-F/Y-N/A-Q-K-F-Q-G (SEQ ID NO:62); and the HCDR3 may have the amino acid sequence: E/D-D/G/H/S/T/P/V/N/1/Y-P/T/N/E/L/A/D/S-Y/K/R/M/P-F/D/S/T/E/W/M/Y/L/Q/K/G/A/I-S/E/G/R-N/E/Q/G/H/M-L/H/S/Y-Y/W-V-M-D-Y (SEQ ID NO:63).

For example, the HCDR1 may have the amino acid sequence: G-Y-T-F-T/S-S-N/A/S/H/Y-Y-M/I-I/S (SEQ ID NO:64); the HCDR2 may have the amino acid sequence: M-G-D-I-N-P-Y-N-G-G/T-T/A-T/N-Y-N/A-Q-K-F-Q-G (SEQ ID NO:65); and the HCDR3 may have the amino acid sequence: E-G/P/D-P-Y-F-S-N-L-Y-V-M-D-Y (SEQ ID NO:66).

In the antibody molecule or antigen-binding portion thereof, the LCDR1 may have the amino acid sequence: R-A-S-Q-S-V-S/D/E-Y-D/E/Q-G-D/E-N-Y-L-N/A (SEQ ID NO:19); the LCDR2 may have the amino acid sequence A/D-A-S-D/N-L/R-E/A-T (SEQ ID NO:67); and the LCDR3 may have the amino acid sequence: Q/H/N-L/Q-S-N/S-E/Q/N-D-L-L-T (SEQ ID NO:68).

For example, the LCDR1 may have the amino acid sequence: R-A-S-Q-S-V-S/E-Y-E/Q-G-D/E-N-Y-L-N/A (SEQ ID NO:69); the LCDR2 may have the amino acid sequence A/D-A-S-D/N-L/R-A-T (SEQ ID NO:70); and the LCDR3 may have the amino acid sequence: Q-L-S-N-E/Q-D-L-L-T (SEQ ID NO:71).

In specific embodiments of the invention, the antibody molecule or antigen-binding portion may comprise:

(A) the amino acid sequences

GYTFSSYYMI, (HCDR1; SEQ ID NO: 31)

MGDINPYNGGANYAQKFQG, (HCDR2; SEQ ID NO: 32)

EGPYFSNLYVMDY, (HCDR3; SEQ ID NO: 33)

RASQSVSYQGENYLA, (LCDR1; SEQ ID NO: 34)

DASNRAT (LCDR2; SEQ ID NO: 35)
and

QLSNQDLLT [Clone MH4]; (LCDR3; SEQ ID NO: 36)
or (B) the amino acid sequences

GYTFSSYYMI, (HCDR1; SEQ ID NO: 31)

MGDINPYNGGANYAQKFQG, (HCDR2; SEQ ID NO: 32)

EGPYFSNLYVMDY, (HCDR3; SEQ ID NO: 33)

RASQSVSYEGENYLN, (LCDR1; SEQ ID NO: 37)

AASNRAT (LCDR2; SEQ ID NO: 38)
and

QLSNEDLLT [Clone MH5]; (LCDR3; SEQ ID NO: 39)

(C) the amino acid sequences

GYTFSSYYMI, (HCDR1; SEQ ID NO: 31)

MGDINPYNGGANYAQKFQG, (HCDR2; SEQ ID NO: 32)

EGPYFSNLYVMDY, (HCDR3; SEQ ID NO: 33)

RASQSVSYEGENYLA, (LCDR1; SEQ ID NO: 40)

AASNRAT (LCDR2; SEQ ID NO: 38)
and

QLSNQDLLT [Clone MH6]; (LCDR3; SEQ ID NO: 36)

(D) the amino acid sequences

GYTFTSYYMI, (HCDR1; SEQ ID NO: 41)

MGDINPYNGGTTYAQKFQG, (HCDR2; SEQ ID NO: 42)

EGPYFSNLYVMDY, (HCDR3; SEQ ID NO: 33)

RASQSVSYEGENYLA, (LCDR1; SEQ ID NO: 40)

AASNLAT (LCDR2; SEQ ID NO: 43)
and

QLSNEDLLT [Clone 30E6]; (LCDR3; SEQ ID NO: 39)

(E) the amino acid sequences

GYTFTSYYMI, (HCDR1; SEQ ID NO: 41)

MGDINPYNGGANFAQKFQG, (HCDR2; SEQ ID NO: 44)

EGPYFSNLYVMDY, (HCDR3; SEQ ID NO: 33)

RASQSVSYEGENYLN, (LCDR1; SEQ ID NO: 37)

AASNRAT (LCDR2; SEQ ID NO: 38)
and

QLSNEDLLT [Clone 29D10]; (LCDR3; SEQ ID NO: 39)

(F) the amino acid sequences

GYTFTSYYMI, (HCDR1; SEQ ID NO: 41)

MGDINPYNGGANYAQKFQG, (HCDR2; SEQ ID NO: 32)

EGPYFSNLYVMDY, (HCDR3; SEQ ID NO: 33)

RASQSVSYEGENYLN, (LCDR1; SEQ ID NO: 37)

AASNRAT (LCDR2; SEQ ID NO: 38)
and

QLSNEDLLT [Clone 29H09]; (LCDR3; SEQ ID NO: 39)

(G) the amino acid sequences

GYTFSSYYMI, (HCDR1; SEQ ID NO: 31)

MGDINPYNGGANYAQKFQG, (HCDR2; SEQ ID NO: 32)

EGPYFSNLYVMDY, (HCDR3; SEQ ID NO: 33)

RASQSVEYQGDNYLN, (LCDR1; SEQ ID NO: 45)

AASNRAT (LCDR2; SEQ ID NO: 38)
and

QLSNEDLLT [Clone 26B07]; (LCDR3; SEQ ID NO: 39)

(H) the amino acid sequences

GYTFTSYYII, (HCDR1; SEQ ID NO: 46)

MGDINPYNGGATYAQKFQG, (HCDR2; SEQ ID NO: 47)

EPPYFSNLYVMDY, (HCDR3; SEQ ID NO: 48)

RASQSVEYEGDNYLN, (LCDR1; SEQ ID NO: 49)

AASNRAT (LCDR2; SEQ ID NO: 38)
and

QLSNQDLLT [Clone 29B07]; (LCDR3; SEQ ID NO: 36)

(I) the amino acid sequences

GYTFSSNYMI, (HCDR1; SEQ ID NO: 50)

MGDINPYNGGATYNQKFQG, (HCDR2; SEQ ID NO: 51)

EPPYFSNLYVMDY, (HCDR3; SEQ ID NO: 48)

RASQSVEYEGENYLN, (LCDR1; SEQ ID NO: 52)

AASNRAT (LCDR2; SEQ ID NO: 38)
and

QLSNQDLLT [Clone 29A03]; (LCDR3; SEQ ID NO: 36)

(J) the amino acid sequences

GYTFSSYYMI, (HCDR1; SEQ ID NO: 31)

MGDINPYNGGTTYAQKFQG, (HCDR2; SEQ ID NO: 42)

EGPYFSNLYVMDY, (HCDR3; SEQ ID NO: 33)

RASQSVEYQGENYLN, (LCDR1; SEQ ID NO: 53)

AASNRAT (LCDR2; SEQ ID NO: 38)
and

QLSNQDLLT [Clone 30D02]; (LCDR3; SEQ ID NO: 36)

(K) the amino acid sequences

GYTFTSNYII, (HCDR1; SEQ ID NO: 54)

MGDINPYNGGTNYAQKFQG, (HCDR2; SEQ ID NO: 55)

EGPYFSNLYVMDY, (HCDR3; SEQ ID NO: 33)

RASQSVEYQGENYLN, (LCDR1; SEQ ID NO: 53)

AASNRAT (LCDR2; SEQ ID NO: 38)
and

QLSSEDLLT [Clone 30G02]; (LCDR3; SEQ ID NO: 56)

(L) the amino acid sequences

GYTFSSNYMI, (HCDR1; SEQ ID NO: 50)

MGDINPYNGGANYAQKFQG, (HCDR2; SEQ ID NO: 32)

EGPYFSNLYVMDY, (HCDR3; SEQ ID NO: 33)

RASQSVSYEGENYLN, (LCDR1; SEQ ID NO: 37)

AASNRAT (LCDR2; SEQ ID NO: 38)
and

-continued (LCDR3; SEQ ID NO: 39)
QLSNEDLLT [Clone MH10, MH11, MH13, MH26, MH27, MH29];

(M) the amino acid sequences (HCDR1; SEQ ID NO: 57)
GYTFSSAYMI, (HCDR2; SEQ ID NO: 32)
MGDINPYNGGANYAQKFQG, (HCDR3; SEQ ID NO: 33)
EGPYFSNLYVMDY, (LCDR1; SEQ ID NO: 37)
RASQSVSYEGENYLN, (LCDR2; SEQ ID NO: 38)
AASNRAT
and (LCDR3; SEQ ID NO: 39)
QLSNEDLLT [Clone MH14, MH15, MH17, MH30, MH31, MH33];

(N) the amino acid sequences (HCDR1; SEQ ID NO: 58)
GYTFSSSYMI, (HCDR2; SEQ ID NO: 32)
MGDINPYNGGANYAQKFQG, (HCDR3; SEQ ID NO: 33)
EGPYFSNLYVMDY, (LCDR1; SEQ ID NO: 37)
RASQSVSYEGENYLN, (LCDR2; SEQ ID NO: 38)
AASNRAT
and (LCDR3; SEQ ID NO: 39)
QLSNEDLLT [Clone MH18, MH19, MH21, MH34, MH35, MH37];

(O) the amino acid sequences (HCDR1; SEQ ID NO: 59)
GYTFSSHYMI, (HCDR2; SEQ ID NO: 32)
MGDINPYNGGANYAQKFQG, (HCDR3; SEQ ID NO: 33)
EGPYFSNLYVMDY, (LCDR1; SEQ ID NO: 37)
RASQSVSYEGENYLN, (LCDR2; SEQ ID NO: 38)
AASNRAT
and (LCDR3; SEQ ID NO: 39)
QLSNEDLLT [Clone MH22, MH23, MH25, MH38, MH39, MH41];

(P) the amino acid sequences (HCDR1; SEQ ID NO: 50)
GYTFSSNYMI, (HCDR2; SEQ ID NO: 32)
MGDINPYNGGANYAQKFQG, (HCDR3; SEQ ID NO: 33)
EGPYFSNLYVMDY, (LCDR1; SEQ ID NO: 37)
RASQSVSYEGENYLN, (LCDR2; SEQ ID NO: 60)
AASDRAT
and (LCDR3; SEQ ID NO: 39)
QLSNEDLLT [Clone MH12, MH28];

(Q) the amino acid sequences (HCDR1; SEQ ID NO: 57)
GYTFSSAYMI, (HCDR2; SEQ ID NO: 32)
MGDINPYNGGANYAQKFQG, (HCDR3; SEQ ID NO: 33)
EGPYFSNLYVMDY, (LCDR1; SEQ ID NO: 37)
RASQSVSYEGENYLN, (LCDR2; SEQ ID NO: 60)
AASDRAT
and (LCDR3; SEQ ID NO: 39)
QLSNEDLLT [Clone MH16, MH32];

(R) the amino acid sequences (HCDR1; SEQ ID NO: 58)
GYTFSSSYMI, (HCDR2; SEQ ID NO: 32)
MGDINPYNGGANYAQKFQG, (HCDR3; SEQ ID NO: 33)
EGPYFSNLYVMDY, (LCDR1; SEQ ID NO: 37)
RASQSVSYEGENYLN, (LCDR2; SEQ ID NO: 60)
AASDRAT
and (LCDR3; SEQ ID NO: 39)
QLSNEDLLT [Clone MH20, MH36];
or (S) the amino acid sequences (HCDR1; SEQ ID NO: 59)
GYTFSSHYMI, (HCDR2; SEQ ID NO: 32)
MGDINPYNGGANYAQKFQG, (HCDR3; SEQ ID NO: 33)
EGPYFSNLYVMDY, (LCDR1; SEQ ID NO: 37)
RASQSVSYEGENYLN, (LCDR2; SEQ ID NO: 60)
AASDRAT
and (LCDR3; SEQ ID NO: 39)
QLSNEDLLT [Clone MH24, MH40].

In some aspects, the invention provides an anti-CSF1R antibody or an antigen-binding portion thereof, wherein the antibody comprises a heavy chain variable (VH) region and a light chain variable (VL) region, wherein
(a) the VH region amino acid sequence comprises HCDR1 of GYTFSSYYMI (SEQ ID NO: 31), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYQGENYLA (SEQ ID NO: 34), LCDR2 of DASNRAT (SEQ ID NO: 35), and LCDR3 of QLSNQDLLT (SEQ ID NO: 36);

(b) the VH region amino acid sequence comprises HCDR1 of GYTFSSYYMI (SEQ ID NO: 31), HCDR2 of MGDINPYNGGANYAQKFQG (SEQ ID NO: 32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(c) the VH region amino acid sequence comprises HCDR1 of GYTFSSYYMI (SEQ ID NO: 31), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLA (SEQ ID NO:40), LCDR2 of AASNRAT (SEQ ID NO:38), and LCDR3 of QLSNQDLLT (SEQ ID NO: 36);

(d) the VH region amino acid sequence comprises HCDR1 of GYTFTSYYMI (SEQ ID NO:41), HCDR2 of MGDINPYNGGTTYAQKFQG (SEQ ID NO: 42), and HCDR3 of EGPYFSNLYVMDY (SEQ ID NO: 33); and the VL region amino acid sequence comprises LCDR1 of RASQSVSYEGENYLA (SEQ ID NO:40), LCDR2 of AASNLAT (SEQ ID NO:43), and LCDR3 of QLSNEDLLT (SEQ ID NO: 39);

(e) the VH region amino acid sequence comprises HCDR1 of GYTFTSYYMI (SEQ ID NO:41), HCDR2 of MGDINPYNGGANFAQKFQG (SEQ ID NO:44), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(f) the VH region amino acid sequence comprises HCDR1 of GYTFTSYYMI (SEQ ID NO:41), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(g) the VH region amino acid sequence comprises HCDR1 of GYTFSSYYMI (SEQ ID NO: 31), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVEYQGDNYLN (SEQ ID NO:45), LCDR2 of AASNRAT (SEQ ID NO:38), and LCDR3 of QLSNEDLLT (SEQ ID NO: 39);

(h) the VH region amino acid sequence comprises HCDR1 of GYTFTSYYII (SEQ ID NO:46), HCDR2 of MGDINPYNGGATYAQKFQG (SEQ ID NO:47), and HCDR3 of EPPYFSNLYVMDY (SEQ ID NO:48); and the VL region amino acid sequence comprises LCDR1 of RASQSVEYEGDNYLN (SEQ ID NO:49), LCDR2 of AASNRAT (SEQ ID NO:38), and LCDR3 of QLSNQDLLT (SEQ ID NO: 36);

(i) the VH region amino acid sequence comprises HCDR1 of GYTFSSNYMI (SEQ ID NO:50), HCDR2 of MGDINPYNGGATYNQKFQG (SEQ ID NO:51), and HCDR3 of EPPYFSNLYVMDY (SEQ ID NO:48); and the VL region amino acid sequence comprises LCDR1 of RASQSVEYEGENYLN (SEQ ID NO:52), LCDR2 of AASNRAT (SEQ ID NO:38), and LCDR3 of QLSNQDLLT (SEQ ID NO: 36);

(j) the VH region amino acid sequence comprises HCDR1 of GYTFSSYYMI (SEQ ID NO: 31), HCDR2 of MGDINPYNGGTTYAQKFQG (SEQ ID NO: 42), and HCDR3 of EGPYFSNLYVMDY (SEQ ID NO: 33); and the VL region amino acid sequence comprises LCDR1 of RASQSVEYQGENYLN (SEQ ID NO:53), LCDR2 of AASNRAT (SEQ ID NO:38), and LCDR3 of QLSNQDLLT (SEQ ID NO: 36);

(k) the VH region amino acid sequence comprises HCDR1 of GYTFTSNYII (SEQ ID NO:54), HCDR2 of MGDINPYNGGTNYAQKFQG (SEQ ID NO:55), and HCDR3 of EGPYFSNLYVMDY (SEQ ID NO: 33); and the VL region amino acid sequence comprises LCDR1 of RASQSVEYQGENYLN (SEQ ID NO:53), LCDR2 of AASNRAT (SEQ ID NO:38), and LCDR3 of QLSSEDLLT (SEQ ID NO:56);

(l) the VH region amino acid sequence comprises HCDR1 of GYTFSSNYMI (SEQ ID NO:50), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(m) the VH region amino acid sequence comprises HCDR1 of GYTFSSAYMI (SEQ ID NO:57), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(n) the VH region amino acid sequence comprises HCDR1 of GYTFSSSYMI (SEQ ID NO:58), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(o) the VH region amino acid sequence comprises HCDR1 of GYTFSSHYMI (SEQ ID NO:59), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(p) the VH region amino acid sequence comprises HCDR1 of GYTFSSNYMI (SEQ ID NO:50), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39);

(q) the VH region amino acid sequence comprises HCDR1 of GYTFSSAYMI (SEQ ID NO:57), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39);

(r) the VH region amino acid sequence comprises HCDR1 of GYTFSSSYMI (SEQ ID NO:58), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39); or (s) the VH region amino acid sequence comprises HCDR1 of GYTFSSHYMI (SEQ ID NO:59), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO:39).

In some embodiments, an anti-CSF1R antibody or antigen-binding portion thereof comprises the six CDRs of any one of clones 29D10, 29B07, 30C11, 26B07, 29A03, 29E11, 30G02, 30E06, 29H09, 30D02, MH1, MH2, MH3, MH4, MH5, MH6, MH7, MH8 or MH9 (see Table 4) and framework regions (FRs) comprising 1, 2, 3, 4, 5, 6, 7, 8, 9, 10, 11, 12, 13, 14, 15, 20, 22, 25, 27, 30, 33 or 35 immunogenicity-reducing mutations compared to sequences of human germline v-domain FRs. The immunogenicity-reducing mutations may be present in the VH framework regions, the VL framework regions, or both the VH and the VL framework regions. For example, an immunogenicity-reducing mutation may be present in the VH FR1, VH FR2, VH FR3, VH FR4, VL FR1, VL FR2, VL FR3, VL FR4, or any combination of these FRs. In some embodiments, the immunogenicity-reducing mutation is an amino acid substitution, deletion or insertion.

In some aspects, disclosed herein is anti-CSF1R antibody or an antigen-binding portion thereof, wherein the antibody comprises a heavy chain variable (VH) region and a light chain variable (VL) region, wherein the VH region comprises any one of the VH region amino acid sequences in Table 11 or 16 and the VL region comprises any one of the VL region amino acid sequences in Table 11 or 16.

In some embodiments, provided herein is an anti-CSF1R antibody or an antigen-binding portion thereof, wherein the antibody comprises a heavy chain variable (VH) region and a light chain variable (VL) region, wherein the VH region amino acid sequence comprises SEQ ID NO:1, SEQ ID NO:2, SEQ ID NO:3; SEQ ID NO:4; SEQ ID NO:5; SEQ ID NO:6; SEQ ID NO:7; or SEQ ID NO:8. Further provided herein is an anti-CSF1R antibody or an antigen-binding portion thereof, wherein the antibody comprises a heavy chain variable (VH) region and a light chain variable (VL) region, wherein the VL region amino acid sequence comprises SEQ ID NO:9; SEQ ID NO:10; SEQ ID NO:11 or SEQ ID NO:12. Also provided herein is an anti-CSF1R antibody or an antigen-binding portion thereof, wherein the antibody comprises a heavy chain variable (VH) region and a light chain variable (VL) region, wherein the VH region amino acid sequence comprises SEQ ID NO:1, SEQ ID NO:2, SEQ ID NO:3; SEQ ID NO:4; SEQ ID NO:5; SEQ ID NO:6; SEQ ID NO:7; or SEQ ID NO:8; and the VL region amino acid sequence comprises SEQ ID NO:9; SEQ ID NO:10; SEQ ID NO:11 or SEQ ID NO:12.

In some embodiments, provided herein is an anti-CSF1R antibody or an antigen-binding portion thereof, wherein the antibody comprises a heavy chain variable (VH) region and a light chain variable (VL) region, wherein (a) the VH region amino acid sequence comprises SEQ ID NO:1, and the VL region amino acid sequence comprises SEQ ID NO:9;

(b) the VH region amino acid sequence comprises SEQ ID NO:1, and the VL region amino acid sequence comprises SEQ ID NO:10;

(c) the VH region amino acid sequence comprises SEQ ID NO:1, and the VL region amino acid sequence comprises SEQ ID NO:11;

(d) the VH region amino acid sequence comprises SEQ ID NO:1, and the VL region amino acid sequence comprises SEQ ID NO:12;

(e) the VH region amino acid sequence comprises SEQ ID NO:2, and the VL region amino acid sequence comprises SEQ ID NO:9;

(f) the VH region amino acid sequence comprises SEQ ID NO:2, and the VL region amino acid sequence comprises SEQ ID NO:10;

(g) the VH region amino acid sequence comprises SEQ ID NO:2, and the VL region amino acid sequence comprises SEQ ID NO:11;

(h) the VH region amino acid sequence comprises SEQ ID NO:2, and the VL region amino acid sequence comprises SEQ ID NO:12;

(i) the VH region amino acid sequence comprises SEQ ID NO:3, and the VL region amino acid sequence comprises SEQ ID NO:9;

(j) the VH region amino acid sequence comprises SEQ ID NO:3, and the VL region amino acid sequence comprises SEQ ID NO:10;

(k) the VH region amino acid sequence comprises SEQ ID NO:3, and the VL region amino acid sequence comprises SEQ ID NO:11;

(l) the VH region amino acid sequence comprises SEQ ID NO:3, and the VL region amino acid sequence comprises SEQ ID NO:12;

(m) the VH region amino acid sequence comprises SEQ ID NO:4, and the VL region amino acid sequence comprises SEQ ID NO:9;

(n) the VH region amino acid sequence comprises SEQ ID NO:4, and the VL region amino acid sequence comprises SEQ ID NO:10;

(o) the VH region amino acid sequence comprises SEQ ID NO:4, and the VL region amino acid sequence comprises SEQ ID NO:11;

(p) the VH region amino acid sequence comprises SEQ ID NO:4, and the VL region amino acid sequence comprises SEQ ID NO:12;

(q) the VH region amino acid sequence comprises SEQ ID NO:5, and the VL region amino acid sequence comprises SEQ ID NO:9;

(r) the VH region amino acid sequence comprises SEQ ID NO:5, and the VL region amino acid sequence comprises SEQ ID NO:10;

(s) the VH region amino acid sequence comprises SEQ ID NO:5, and the VL region amino acid sequence comprises SEQ ID NO:11;

(t) the VH region amino acid sequence comprises SEQ ID NO:5, and the VL region amino acid sequence comprises SEQ ID NO:12;

(u) the VH region amino acid sequence comprises SEQ ID NO:6, and the VL region amino acid sequence comprises SEQ ID NO:9;

(v) the VH region amino acid sequence comprises SEQ ID NO:6, and the VL region amino acid sequence comprises SEQ ID NO:10;

(w) the VH region amino acid sequence comprises SEQ ID NO:6, and the VL region amino acid sequence comprises SEQ ID NO:11;

(x) the VH region amino acid sequence comprises SEQ ID NO:6, and the VL region amino acid sequence comprises SEQ ID NO:12;

(y) the VH region amino acid sequence comprises SEQ ID NO:7, and the VL region amino acid sequence comprises SEQ ID NO:9;
(z) the VH region amino acid sequence comprises SEQ ID NO:7, and the VL region amino acid sequence comprises SEQ ID NO:10;
(aa) the VH region amino acid sequence comprises SEQ ID NO:7, and the VL region amino acid sequence comprises SEQ ID NO:11;
(bb) the VH region amino acid sequence comprises SEQ ID NO:7, and the VL region amino acid sequence comprises SEQ ID NO:12;
(cc) the VH region amino acid sequence comprises SEQ ID NO:8, and the VL region amino acid sequence comprises SEQ ID NO:9;
(dd) the VH region amino acid sequence comprises SEQ ID NO:8, and the VL region amino acid sequence comprises SEQ ID NO:10;
(ee) the VH region amino acid sequence comprises SEQ ID NO:8, and the VL region amino acid sequence comprises SEQ ID NO:11; or
(ff) the VH region amino acid sequence comprises SEQ ID NO:8, and the VL region amino acid sequence comprises SEQ ID NO:12.

In some aspects, disclosed herein is an anti-CSF1R antibody or an antigen-binding portion thereof, wherein the antibody comprises a heavy chain variable (VH) region and a light chain variable (VL) region, wherein
(a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:352 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:351;
(b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:354 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:353;
(c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:356 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:355; or
(d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:358 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:357. In some aspects, the CDR amino acid sequences of an anti-CSF1R antibody are 100% identical to the CDR amino acid sequences in the recited sequences while the FR amino acid sequences are less than 100% identical to the FR amino acid sequences in the recited sequences.

In some aspects, the antibody or antigen-binding portion as defined herein may be isolated.

The antibody molecule or antigen-binding portion as defined herein may cross-compete for binding to CSF1R with an antibody or antigen-binding portion thereof comprising the sets of CDRs disclosed herein. In some embodiments, the invention provides an anti-CSF1R antibody or an antigen-binding portion thereof, wherein the antibody or antigen-binding portion cross-competes for binding to CSF1R with an antibody or antigen-binding portion whose sequences are provided herein; and (a) comprises fully germline human framework amino acid sequences; (b) binds specifically to human CSF1R, cynomolgus CSF1R, and rhesus CSF1R; (c) binds to monomeric cynomolgus CSF1R with a KD lower than 0.66 nM and to human CSF1R with a KD lower than 0.21 nM; and/or (d) binds to a functionally identical epitope on cynomolgus CSF1R and rhesus CSF1R. In some embodiments, the invention provides an anti-CSF1R antibody or an antigen-binding portion thereof, wherein the antibody or antigen-binding portion cross-competes for binding to CSF1R with an antibody or antigen-binding portion whose sequences are provided herein; and (a) comprises fully germline human framework amino acid sequences; (b) comprises the IGHV1-69*01 allele germline framework regions in the VH domain; (c) does not contain an isomerisation risk motif in the LCDR1 sequence; (d) binds specifically to human CSF1R, cynomolgus CSF1R, and rhesus CSF1R; (e) binds to human CSF1R with a KD that is within 3-fold of said antibody's or antigen-binding portion's KD for binding to cynomolgus CSF1R; (f) does not comprise a human T cell epitope sequence in the Framework 3/LCDR3 region of the VL domain; and/or (g) does not comprise a human T cell epitope sequence in the HCDR-2/Framework 3 region of the VH domain; and/or (h) does not comprise a human T cell epitope sequence in the HCDR1/Framework 2 region of the VH domain; and/or (i) does not comprise a human T cell epitope sequence in the HCDR3/Framework 4 region of the VH domain; and/or (j) does not comprise a human T cell epitope sequence in the Framework 2/LCDR2 region of the VL domain; and/or (k) exhibits minimal or no binding to insulin (e.g., human insulin) and/or double-stranded DNA (dsDNA); and/or (l) exhibits reduced susceptibility to oxidative damage compared to antibody hu0301, when in IgG4(S228P) antibody format; and/or (m) exhibits improved thermal stability in the Fab domain compared to antibody hu0301, when in IgG4(S228P) antibody format; and/or (n) exhibits reduced hydrophobic species heterogeneity compared to antibody hu0301, when in IgG4(S228P) antibody format.

In some embodiments, an anti-CSF1R antibody or an antigen-binding portion of the invention binds to monomeric cynomolgus CSF1R with a KD lower than 2 nM and to human CSF1R with a KD lower than 2 nM. In some embodiments, an anti-CSF1R antibody or an antigen-binding portion of the invention binds to monomeric cynomolgus CSF1R with a KD lower than 1 nM and to human CSF1R with a KD lower than 1 nM.

In some embodiments, a KD value of an antibody or antigen-binding portion may be determined by Biacore analysis. In some embodiments, an EC50 value of an antibody or antigen-binding portion may be determined by flow cytometric staining of CSF1R expressing cells (e.g., HEK cells).

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-CSF1R antibodies of the invention to the target CSF1R (e.g., human CSF1R). The extent to which an antibody or portion thereof is able to interfere with the binding of another to the target, and therefore whether it can be said to cross-block or cross-compete according to the invention, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The anti-CSF1R antibody molecule or antigen-binding portion as defined herein may be thermally stable. In some cases, an antibody molecule or antigen-binding portion may have substantially the same thermal stability as murine anti-CSF1R antibody 0301 or hu0301 (humanized). In some cases, an antibody molecule or antigen-binding portion may be more thermally stable than murine anti-CSF1R antibody 0301 or hu0301 (humanized). In some cases, an antibody molecule or antigen-binding portion may be less thermally stable than murine anti-CSF1R antibody 0301 or hu0301 (humanized). In some examples, an antibody molecule or antigen-binding portion may have a Tm from about 76° C. to about 78° C. and may be in an IgG4(S228P) format. In some aspects, an antibody molecule or antigen-binding portion may have a Tm from about 76.6° C. to about 77.7° C. and may be in an IgG4(S228P) format. The melting temperature of an antibody molecule or antigen-binding portion thereof may be analysed by a differential scanning calorimetry (DSC) assay.

The anti-CSF1R antibody molecule or antigen-binding portion as defined herein may be resistant to oxidation (e.g., resistant to oxidation of exposed amino acid residues). In some cases, an antibody molecule or antigen-binding portion may undergo reduced oxidation of exposed amino acid residues compared to murine anti-CSF1R antibody 0301 or hu0301 (humanized), or an anti-CSF1R antibody comprising the variable domain sequences of antibody hu0301 (humanized). Oxidation resistance of an antibody molecule or antigen-binding portion thereof may be analysed by adding an oxidative reagent (e.g., $H_2O_2$) to the antibody molecule or antigen-binding portion and analysing changes induced by oxidation by Reverse Phase (RP) Chromatography methods.

The anti-CSF1R antibody molecule or antigen-binding portion as defined herein may exhibit lower heterogeneity of hydrophobic species. In some cases, an antibody molecule or antigen-binding portion may exhibit reduced heterogeneity of hydrophobic species compared to murine anti-CSF1R antibody 0301 or hu0301 (humanized), or an anti-CSF1R antibody comprising the variable domain sequences of antibody hu0301 (humanized). The hydrophobic species heterogeneity of an antibody molecule or antigen-binding portion thereof may be analysed by Hydrophobic Interaction Chromatography (HIC) methods.

In some embodiments, an anti-CSFR1 antibody molecule or antigen-binding portion provided herein does not bind or minimally binds to insulin and/or dsDNA. In some embodiments, the insulin is human insulin. In some embodiments, an anti-CSFR1 antibody molecule or antigen-binding portion provided herein exhibits no binding to insulin and/or dsDNA above background binding. In some embodiments, an anti-CSFR1 antibody molecule or antigen-binding portion exhibits reduced binding to insulin and/or dsDNA compared to the binding exhibited by Bococizumab, Briakinumab, Ustekinumab or Bevacizumab, or any combination of these antibodies. In some embodiments, binding to insulin or dsDNA may be determined by ELISA.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the 0301 murine LCDR1 (as defined herein, i.e. the amino acid sequence KASQSVDYDGDNYMN; SEQ ID NO:22) has been identified to have a putative isomerization site at residues 9 and 10 (DG). Removal of this site at equivalent positions in an LCDR1 of the invention, for example by conservative or non-conservative substitution of the D (such as to E, Q, H), is envisaged (as for example in clone 30E06 and other clones in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region amino acid sequences.

The antibody molecule or antigen-binding portion thereof may comprise an IGHV1-69 human germline scaffold into which the corresponding HCDR sequences have been inserted. The antibody molecule or antigen-binding portion thereof may comprise a VH region that comprises an IGHV1-69 human germline scaffold amino acid sequence into which a set of corresponding HCDR1, HCDR2 and HCDR3 amino acid sequences have been inserted. In some embodiments, the antibody molecule or antigen-binding portion of the invention comprises the IGHV1-69*01 allele germline framework regions in the VH domain.

The antibody molecule or antigen-binding portion thereof may comprise an IGKV3-11 human germline scaffold into which the corresponding LCDR sequences have been inserted. The antibody molecule or antigen-binding portion thereof may comprise a VL region that comprises an IGKV3-11 human germline scaffold amino acid sequence into which a set of corresponding LCDR1, LCDR2 and LCDR3 amino acid sequences have been inserted.

The antibody molecule or antigen-binding portion thereof may comprise an IGHV1-69 human germline scaffold into which the corresponding HCDR sequences have been inserted and an IGKV3-11 human germline scaffold into which the corresponding LCDR sequences have been inserted. The antibody molecule or antigen-binding portion thereof may comprise a VH region that comprises an IGHV1-69 human germline scaffold amino acid sequence into which a set of corresponding HCDR1, HCDR2 and HCDR3 amino acid sequences have been inserted and a VL region that comprises an IGKV3-11 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4 (with all six CDR sequences being from the same clone).

In some aspects, the antibody molecule or antigen-binding portion thereof may comprise an immunoglobulin constant region. In some embodiments, the immunoglobulin constant region is IgG1, IgG2, IgG3, IgG4, IgA1 or IgA2. In additional embodiments, the immunoglobulin constant region is IgG1, IgG2, IgG3, IgG4, IgA1 or IgA2. The antibody molecule or antigen-binding portion thereof may comprise an immunologically inert constant region. In some aspects, an anti-CSFR1 antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-CSFR1 antibody may comprise an immunoglobulin constant region comprising any one of the amino acid sequences in Table 17. The Fc region sequences in Table 17 begin at the CH1 domain. In some aspects, an anti-CSFR1 antibody may comprise an immunoglobulin constant region comprising an amino acid sequence of an Fc region of human IgG4, human IgG4(S228P), human IgG1, human IgG1-3M or human IgG1-4M. For example, the human IgG4(S228P) Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some aspects, a position of an amino acid residue in a constant region of an immunoglobulin molecule is numbered according to EU nomenclature (Ward et al., 1995 *Therap. Immunol.* 2:77-94). In some aspects, an immunoglobulin constant region may comprise an RDELT (SEQ ID NO:72) motif or an REEM (SEQ ID NO:73) motif (underlined in Table 17). The REEM (SEQ ID NO:73) allotype is found in a smaller human population than the RDELT (SEQ ID NO:72) allotype. In some aspects, an anti-CSFR1 antibody may comprise an immunoglobulin constant region comprising any one of SEQ ID NOS:359-364. In some aspects, an anti-CSFR1 antibody may comprise the six CDR amino acid sequences of any one of the clones in Table 4 and any one of the Fc region amino acid sequences in Table 17. In some aspects, an anti-CSFR1 antibody may comprise an immunoglobulin heavy chain constant region comprising any one of the Fc region amino acid sequences in Table 17 and an immunoglobulin light chain constant region that is a kappa light chain constant region or a lambda light chain constant region.

In some aspects, disclosed herein is an anti-CSF1R antibody or an antigen-binding portion thereof, wherein the antibody comprises a heavy chain variable (VH) region and a light chain variable (VL) region and a heavy chain constant region, wherein (a) the VH region amino acid sequence comprises HCDR1 of GYTFSSYYMI (SEQ ID NO: 31), HCDR2 of MGDINPYNGGANYAQKFQG (SEQ ID NO: 32) and HCDR3 of EGPYFSNLYVMDY (SEQ ID NO: 33); the VL region amino acid sequence comprises LCDR1 of RASQSVSYEGENYLN (SEQ ID NO: 37), LCDR2 of AASNRAT (SEQ ID NO:38) and LCDR3 of QLSNEDLLT (SEQ ID NO: 39); and the heavy chain constant region comprises any one of SEQ ID NOS: 359-364;

(b) the VH region amino acid sequence comprises HCDR1 of GYTFSSNYMI (SEQ ID NO:50), HCDR2 of MGDINPYNGGANYAQKFQG (SEQ ID NO: 32), HCDR3 of EGPYFSNLYVMDY (SEQ ID NO: 33); the VL region amino acid sequence comprises LCDR1 of RASQSVSYEGENYLN (SEQ ID NO: 37), LCDR2 of AASDRAT (SEQ ID NO:60) and LCDR3 of QLSNEDLLT (SEQ ID NO: 39); and the heavy chain constant region comprises any one of SEQ ID NOS: 359-364;

(c) the VH region amino acid sequence comprises HCDR1 of GYTFSSAYMI (SEQ ID NO:57), HCDR2 of MGDINPYNGGANYAQKFQG (SEQ ID NO:32) and HCDR3 of EGPYFSNLYVMDY (HCDR3; SEQ ID NO: 33); the VL region amino acid sequence comprises LCDR1 of RASQSVSYEGENYLN (SEQ ID NO:37), LCDR2 of AASDRAT (SEQ ID NO:60) and LCDR3 of QLSNEDLLT (SEQ ID NO:39); and the heavy chain constant region comprises any one of SEQ ID NOS:359-364; or (d) the VH region amino acid sequence comprises HCDR1 of GYTFTSYYMI (SEQ ID NO:41), HCDR2 of MGDINPYNGGTTYAQKFQG (SEQ ID NO:42) and HCDR3 of EGPYFSNLYVMDY (SEQ ID NO:33); the VL region amino acid sequence comprises LCDR1 of RASQSVSYEGENYLA (SEQ ID NO:40), LCDR2 of AASNLAT (SEQ ID NO:43) and LCDR3 of QLSNEDLLT (SEQ ID NO:39); and the heavy chain constant region comprises any one of SEQ ID NOS: 359-364.

In some aspects, disclosed herein is an anti-CSF1R antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:352; the VL region amino acid sequence comprises or consists of SEQ ID NO:351;

and the heavy chain constant region comprises a wild-type human IgG4 constant region, a human IgG4 constant region comprising the amino acid substitution S228P, a wild-type human IgG1 constant region or a human IgG1 constant region comprising the amino acid substitutions L234A, L235A and G237A;
- (b) the VH region amino acid sequence comprises or consists of SEQ ID NO:354; the VL region amino acid sequence comprises or consists of SEQ ID NO:353; and the heavy chain constant region comprises a wild-type human IgG4 constant region, a human IgG4 constant region comprising the amino acid substitution S228P, a wild-type human IgG1 constant region or a human IgG1 constant region comprising the amino acid substitutions L234A, L235A and G237A;
- (c) the VH region amino acid sequence comprises or consists of SEQ ID NO:356; the VL region amino acid sequence comprises or consists of SEQ ID NO:355; and the heavy chain constant region comprises a wild-type human IgG4 constant region, a human IgG4 constant region comprising the amino acid substitution S228P, a wild-type human IgG1 constant region or a human IgG1 constant region comprising the amino acid substitutions L234A, L235A and G237A; or
- (d) the VH region amino acid sequence comprises or consists of SEQ ID NO:358; the VL region amino acid sequence comprises or consists of SEQ ID NO:357; and the heavy chain constant region comprises a wild-type human IgG4 constant region, a human IgG4 constant region comprising the amino acid substitution S228P, a wild-type human IgG1 constant region or a human IgG1 constant region comprising the amino acid substitutions L234A, L235A and G237A.

In some aspects, disclosed herein is an anti-CSF1R antibody or an antigen-binding portion thereof, wherein the antibody comprises a heavy chain variable (VH) region and a light chain variable (VL) region and a heavy chain constant region, wherein
- (a) the VH region amino acid sequence comprises or consists of SEQ ID NO:352; the VL region amino acid sequence comprises or consists of SEQ ID NO:351; and the heavy chain constant region comprises any one of SEQ ID NOS:359-364;
- (b) the VH region amino acid sequence comprises or consists of SEQ ID NO:354; the VL region amino acid sequence comprises or consists of SEQ ID NO:353; and the heavy chain constant region comprises any one of SEQ ID NOS:359-364;
- (c) the VH region amino acid sequence comprises or consists of SEQ ID NO:356; the VL region amino acid sequence comprises or consists of SEQ ID NO:355; and the heavy chain constant region comprises any one of SEQ ID NOS:359-364; or
- (d) the VH region amino acid sequence comprises or consists of SEQ ID NO:358; the VL region amino acid sequence comprises or consists of SEQ ID NO:357; and the heavy chain constant region comprises any one of SEQ ID NOS:359-364.

In some aspects, an anti-CSFR1 antibody may be immune effector null. In some aspects, an anti-CSFR1 antibody or an antigen-binding portion thereof does not induce immune effector function and, optionally, suppresses immune effector function. In some aspects, an anti-CSFR1 antibody may lack measurable binding to human FcγRI, FcγRIIa, FcγRIIIa and FcγRIIIb receptors but maintain binding to human FcγRIIb receptor and optionally maintain binding to human FcRn receptor. FcγRI, FcγRIIa, FcγRIIIa and FcγRIIIb are examples of activating receptors. FcγRIIb is an example of an inhibitory receptor. FcRn is an example of a recycling receptor. In some aspects, binding affinity of an anti-CSFR1 antibody or an antigen-binding portion thereof for human Fc receptors may be measured by BIACORE® analysis. In some aspects, Homogeneous Time Resolved Fluorescence (HTRF) can be used to study binding of an anti-CSFR1 antibody to human Fc receptors. In one example of HTRF, human IgG1 (wild type) is labelled, as is the full suite of Fc gamma receptors and then antibodies with engineered Fc fragments are used in titration competition. In some aspects, CSFR1-positive cells may be mixed with human white blood cells and anti-CSFR1 antibodies, and cell killing by CDC, ADCC and/or ADCP may be measured. In some aspects, an anti-CSFR1 antibody comprising an amino acid sequence of an Fc region of human IgG1-3M (see Table 17) is effector null. In some aspects, an anti-CSFR1 antibody comprising an amino acid sequence of an Fc region of human IgG1-3M (see Table 17) is not effector null.

The antibody molecule or antigen-binding portion thereof may be a Fab fragment, a F(ab)$_2$ fragment, an Fv fragment, a tetrameric antibody, a tetravalent antibody, a multispecific antibody (for example, a bivalent antibody), a domain-specific antibody, a single domain antibody, a monoclonal antibody or a fusion protein. In one embodiment, an antibody may be a bispecific antibody that binds specifically to a first antigen and a second antigen, wherein the first antigen is CSF1R and the second antigen is not CSF1R. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the anti-folates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, downregulate self-antigen expression, or mask MHC antigens.

Also provided is a nucleic acid molecule encoding the antibody molecule or antigen-binding portion thereof of the invention as defined herein. A nucleic acid molecule may encode (a) the VH region amino acid sequence; (b) the VL region amino acid sequence; or (c) both the VH and the VL region amino acid sequences of an anti-CSF1R antibody or an antigen-binding portion thereof described herein. In some aspects, the nucleic acid molecule as defined herein may be isolated.

Further provided is a vector comprising the nucleic acid molecule of the invention as defined herein. The vector may be an expression vector.

Also provided is a host cell comprising the nucleic acid molecule or the vector of the invention as defined herein. The host cell may be a recombinant host cell.

In a further aspect there is provided a method of producing an anti-CSF1R antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

The cancer may for example be selected from the group consisting of: pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues. In one embodiment, the cancer is acute myeloid leukaemia.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

The invention further provides a method for depleting immunosuppressive CSF1R+ cells in the tumour microenvironment that inhibit the anti-tumour activity of T cells in a subject in need thereof, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent. In some embodiments, a second therapeutic agent is a checkpoint inhibitor molecule. For example, a checkpoint inhibitor molecule may be an anti-PD1 antibody.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an infectious or immune disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein. In one embodiment, the immune disease is pigmented villonodular synovitis. In some embodiments, the infectious disease is viral, bacterial, fungal or parasitic.

In one embodiment, the invention provides an anti-CSF1R antibody or an antigen-binding portion thereof comprising the amino acid sequences disclosed herein for use in therapy.

The pharmaceutical composition of the invention may comprise a pharmaceutically acceptable excipient, carrier, or diluent. A pharmaceutically acceptable excipient may be a compound or a combination of compounds entering into a pharmaceutical composition which does not provoke secondary reactions and which allows, for example, facilitation of the administration of the anti-CSF1R antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-CSF1R antibody molecule.

In some embodiments, the anti-CSF1R antibody molecule may be provided in a lyophilised form for reconstitution prior to administration. For example, lyophilised antibody molecules may be re-constituted in sterile water and mixed with saline prior to administration to an individual.

The anti-CSF1R antibody molecules will usually be administered in the form of a pharmaceutical composition, which may comprise at least one component in addition to the antibody molecule. Thus pharmaceutical compositions may comprise, in addition to the anti-CSF1R antibody molecule, a pharmaceutically acceptable excipient, carrier, buffer, stabilizer or other materials well known to those skilled in the art. Such materials should be non-toxic and should not interfere with the efficacy of the anti-CSF1R antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-CSF1R antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-CSF1R antibody molecule may be administered alone or in combination with other treatments, either simultaneously or sequentially dependent upon the condition to be treated.

An anti-CSF1R antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-CSF1R antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-CSF1R antibody molecules as described herein may be administered as sub-cutaneous injections. Sub-cutaneous injections may be administered using an auto-injector, for example for long term prophylaxis/treatment.

In some preferred embodiments, the therapeutic effect of the anti-CSF1R antibody molecule may persist for several half-lives, depending on the dose. For example, the therapeutic effect of a single dose of the anti-CSF1R antibody molecule may persist in an individual for 1 month or more, 2 months or more, 3 months or more, 4 months or more, 5 months or more, or 6 months or more.

The invention also provides a method of producing an antibody molecule which specifically binds to human CSF1R and optionally also to cynomolgus and rhesus monkey CSF1R, or an antigen-binding portion thereof, comprising the steps of:

(1) grafting anti-CSF1R CDRs from a non-human source into a human v-domain framework to produce a humanized anti-CSF1R antibody molecule or antigen-binding portion thereof;

(2) generating a library of clones of the humanized anti-CSF1R antibody molecule or antigen-binding portion thereof comprising one or more mutations in the CDRs;

(3) screening the library for binding to human CSF1R and optionally also to cynomolgus and rhesus monkey CSF1R;

(4) selecting clones from the screening step (3) having binding specificity to human CSF1R and optionally also to cynomolgus and rhesus monkey CSF1R; and (5) producing an antibody molecule which specifically binds to human CSF1R and optionally also to cynomolgus and rhesus monkey CSF1R, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "CSF1R" refers to Colony Stimulating Factor 1 Receptor and variants thereof that retain at least part of the biological activity of CSF1R. As used herein, CSF1R includes all species of native sequence CSF1R, including human, rat, mouse and chicken. The term "CSF1R" is used to include variants, isoforms and species homologs of human CSF1R. Antibodies of the invention may cross-react with CSF1R from species other than human, in particular CSF1R from cynomolgus monkey (*Macaca fascicularis*) and rhesus monkey (*Macaca mulatta*). In certain embodiments, the antibodies may be completely specific for human CSF1R and may not exhibit non-human cross-reactivity.

As used herein, an "antagonist" as used in the context of the antibody of the invention or an "anti-CSF1R antagonist antibody" (interchangeably termed "anti-CSF1R antibody") refers to an antibody which is able to bind to CSF1R and inhibit CSF1R biological activity and/or downstream pathway(s) mediated by CSF1R signalling. An anti-CSF1R antagonist antibody encompasses antibodies that can block, antagonize, suppress or reduce (including significantly) CSF1R biological activity, including downstream pathways mediated by CSF1R signalling, such as receptor binding and/or elicitation of a cellular response to CSF1R. For the purposes of the present invention, it will be explicitly understood that the term "anti-CSF1R antagonist antibody" encompass all the terms, titles, and functional states and characteristics whereby CSF1R itself, and CSF1R biological activity (including but not limited to its ability to modulate the activity of mononuclear cells), or the consequences of the activity or biological activity, are substantially nullified, decreased, or neutralized in any meaningful degree.

CSF1R "specifically binds" "specifically interacts", "preferentially binds", "binds" or "interacts" with CSF1R if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to CSF1R. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the 0301 murine anti-CSF1R antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value 0 in the following BLOSUM 62 substitution matrix (see Henikoff & Henikoff, 1992, PNAS 89: 10915-10919):

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to CSF1R and is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation (1) is not associated with naturally associated components

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -2 | -1 | 1 | 5 | -2 | -2 | 0 |
| W | -2 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4. |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 µM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen CSF1R to inhibit 50% of activity measured in a CSF1R activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to CSF1R.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neoadjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-CSF1R Therapeutic Antibodies

Introduction

In this example, we successfully generate a panel of agonistic, optimized anti-CSF1R antibodies. These anti-CSF1R antibodies are well expressed, biophysically stable, highly soluble and of maximized identity to preferred human germlines.

Materials and Methods

CSF1R Library Generation and Selection

The CSF1R Fab repertoire was assembled by mass oligo synthesis and PCR. The amplified Fab repertoire was then cloned via restriction-ligation into a phagemid vector, transformed into *E. coli* TG-1 cells, and the phage repertoire rescued essentially as previously described in detail (Finlay et al., 2011, Methods Mol Biol 681: 383-401).

Phage selections were performed by coating streptavidin magnetic microbeads with biotinylated CSF1R target protein (either human or cyno), washing the beads thrice with PBS and resuspending in PBS pH7.4 plus 5% skim milk protein. These beads were coated at 100 nM target protein in round 1 of selection, followed by reduced antigen concentrations in three successive rounds. In each round, phage were eluted using trypsin before re-infection into TG1 cells.

Periplasmic Extracts Production (Small-Scale)

Production of soluble Fabs in individual *E. coli* clones was performed. *E. coli* TG1 cells in logarhythmic growth phase were induced with isopropyl 1-thio-β-D-galactopyranoside. Periplasmic extracts containing soluble Fab were generated by a freeze/thaw cycle: BacteriaL cell pellets were frozen at −20° C. for overnight and then thawed at room temperature and resuspended in PBS pH 7.4. The supernatants containing the soluble Fab were collected after shaking at room temperature and centrifugation.

IgG Expression and Purification

Mammalian codon-optimized synthetic genes encoding the heavy and light chain variable domains of the lead panel anti-CSF1R antibodies plus the mu0301 and hu0301 were cloned into mammalian expression vectors comprising human IgG4-S228P (human IgG4 containing the S228P mutation in the hinge region that stabilises the hinge) and human Cκ domains, respectively. Co-transfection of heavy and light chain containing vector in mammalian expression system was performed, followed by protein A-based purification of the IgG, quantification and QC on denaturing and non-denaturing SDS-PAGE.

Direct Binding ELISA for Fab and IgG

Binding and cross-reactivity of the lead panel to the recombinant proteins was initially assessed by binding ELISA. The human CSF1R human Fc tagged recombinant protein and the cynomolgus monkey CSF1R human Fc tagged recombinant protein were coated to the surface of MaxiSorp™ flat-bottom 96 well plate at 1 μg/ml. The purified IgG samples were titrated in two fold serial dilutions starting from 500 nM to 0.008 nM and allowed to bind to the coated antigens. The Fabs were detected using mouse anti-c-myc antibody followed by donkey anti-mouse IgG conjugated to horseradish peroxidase. The IgGs were detected using the mouse anti-human IgG conjugated to horseradish peroxidase. Binding signals were visualized with 3,3′,5,5′-Tetramethylbenzidine Substrate Solution (TMB) and the absorbance measured at 450 nm.

Alphascreen Epitope Competition Assay for IgG Antibodies

The AlphaScreen assay (Perkin Elmer) was performed in a 25 μl final volume in 384-well white microtiter plates (Greiner). The reaction buffer contained 1×PBS pH 7.3 (Oxoid, Cat. nr. BR0014G) and 0.05% (v/v) Tween® 20 (Sigma, Cat. nr. P9416). Purified IgG samples were titrated in three fold serial dilutions starting at 500 nM final concentration and incubated with biotinylated human CSF1R for 20 minutes at room temperature. The mu0301 IgG at and the anti-human IgG Acceptor beads were added and the mix was incubated for 1 hour at room temperature, followed by addition of the Streptavidin Donor beads at 20 μg/ml (final concentration) and incubation for 30 minutes at room temperature. The emission of light was measured in the EnVision multilabel plate reader (Perkin Elmer) and analysed using the EnVision manager software. Values were reported as Counts Per Second (CPS) and corrected for crosstalk. The EC50 values were calculated using the MFI values in GraphPad Prism software (GraphPad Software, La Jolla, Calif.).

Biacore Analyses of IgG Affinity for Monomeric Human and Cyno CSF1R in Solution

Affinity (KD) of purified IgGs was determined via SPR with antigen in-solution on a Biacore 3000 (GE). A mouse anti-human antibody (CH1 specific) was immobilized on a CM5 Sensor Chip to a level of 2000 RU in acetate buffer at pH 4.5 using amine coupling following the Wizard instructions for two channels. One channel was used for background signal correction. The standard running buffer HBS-EP pH 7.4 was used. Regeneration was performed with a single injection of 10 μl of 10 mM Glycine at pH 1.5 at 20 μl/minute. IgG samples were injected for 2 minutes at 50 nM at 30 μl/min followed by and off-rate of 60 seconds. The monomeric ectodomain protein (human CSF1R or cynomolgus monkey CSF1R) was injected in two fold serial dilutions from 100 nM down to 3.1 nM, for 2 minutes at 30 μl/min followed by an off-rate of 300 seconds. The obtained sensorgrams were analysed using the Biacore 3000 evaluation (BIAevaluation) software. The KD was calculated by simultaneous fitting of the association and dissociation phases to a 1:1 Langmuir binding model.

Flow Cytometry of IgGs

Purified IgGs were tested in FACs for binding to human and cyno CSF1R expressed on HEK-293 cells. The IgG samples were titrated in three-fold serial dilutions starting at 500 nM to 0.98 nM. Binding of IgGs was detected with a mouse anti-human IgG conjugated to FITC. Results were analyzed by examining the Mean Fluorescence Intensity (MFI) of 10000 cells per sample in the BL-1 channel detector of a flow cytometer (Attune™ NxT Acoustic Focusing Cytometer, Invitrogen/ThermoFisher Scientific).

Antibody v-Domain T Cell Epitope Content: In Silico Analyses

In silico technologies (Abzena, Ltd.), which are based on identifying the location of T cell epitopes in therapeutic antibodies and proteins, were used for assessing potential immunogenicity in antibody v-domains. iTope™ was used to analyse the VL and VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

In addition, the sequences were analysed using TCED™ (T Cell Epitope Database™) search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

Primary Human Monocyte Proliferation Assay

Primary human CD14+ monocytes were freshly isolated from the peripheral blood of 3 healthy human donors. Monocyte samples were treated with 2400 IU/ml M-CSF in the presence or absence of titrated anti-CSF1R IgG4-5228P clones. After 5 days, the cell survival/proliferation was quantified using CCK-8 reagent. Plates were read at intervals from 1 to 3 hours after addition of CCK-8 and the time point at which vehicle treated wells had an OD450 nm of 2 to 2.5 was used for analysis.

Differential Scanning Calorimetry (DSC) Analysis

The Tm of test articles was analysed using a MicroCal PEAQ-DSC (Malvern Instruments, Malvern, UK) running version 1.22 software. The samples were heated at a rate of 200° C./hour over a range of 20-110° C. Thermal data was normalised based on protein concentration. The Tm of the protein was determined from the heating scan data.

Forced Oxidation Analyses

For forced oxidation analysis of digested IgGs: test articles were treated with 0.5% H2O2 at room temperature for 2 hours. Native and oxidised IgG4(S228P) samples were digested with trypsin using the SMART Digest™ kit (ThermoFisher Scientific, Hemel Hempstead, UK) by following the manufacturer's protocol. The resulting tryptic peptides were immediately analysed by Reverse Phase chromatography. Chromatographic separation was performed using an Acquity UPLC CSH C18 Column, 130 Å, 1.7 µm, 2.1 mm×150 mm (Waters, Elstree, UK) connected to a Dionex Ultimate 3000RS HPLC system (ThermoFisher Scientific, Hemel Hempstead, UK). The method consisted of a linear gradient from 95% buffer A (0.1% FA in $H_2O$) to 15% buffer B (0.085% FA in 75% acetonitrile) over 4 minutes, followed by a linear gradient from 15% buffer B to 60% buffer B over 22 minutes. The flow rate was 0.2 mL/minute and the temperature was maintained at 40° C. throughout the analysis. Detection was carried out by UV absorption at 280 nm.

Hydrophobic Interaction Chromatography (HIC) Analyses

Chromatographic separation was performed using a TSKgel Butyl-NPR 4.6 mm×35 mm HIC column (TOSOH Bioscience Ltd., Reading, UK) connected to a Dionex Ultimate 3000RS HPLC system (ThermoFisher Scientific, Hemel Hempstead, UK). The method consisted of a linear gradient from 60% Buffer A (100 mM sodium phosphate pH 7.0, 2 M ammonium sulphate) to 90% Buffer B (100 mM sodium phosphate pH 7.0) over 9 minutes. The flow rate was 1.2 mL/minute. Detection was carried out by UV absorption at 280 nm.

Results and Discussion

CDR Grafting onto Preferred Human Germline v-Genes

The CDRs of an antagonistic murine anti-CSF1R IgG '0301' (mu0301; see WO2011/140249A2 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV1-69 and IGKV3-11, which are known to have good solubility and drug development qualities, and are used at high frequency in the expressed human antibody repertoire. The IGHV1-69 germline gene is known to have a significant number of allelic variants in the human population. Human immune repertoire sequencing studies have shown the allele IGHV1-69*01 to be the most commonly expressed and, as such, it was chosen as the specific allele on which to base the CDR grafts and library design.

Those scaffolds and grafted CDR definitions are outlined in Table 2. The heavy and light chain sequences for murine anti-CSF1R antibody are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGHV1-69/IGKV3-11 germline graft was therefore taken forward as the template for CDR mutagenesis and selection of improved clones.

Library Generation and Screening

The CDR-grafted IGHV1-69/IGKV3-11 v-domain sequences were combined into a Fab phage display format and a mutagenesis library cassette was generated by oligo synthesis and assembly. Mutagenesis libraries were synthesised to not only sample human germline and murine residues in the CDRs, but also to sample mutations (e.g. D/E/Q) that could facilitate the potential removal of amino acids in the LCDR1 which are not found in the human germline IGKV3-11 (motif 'YDGDN' (SEQ ID NO: 74)), that contain the high risk putative isomerisation motif 'DG'. This additional mutagenesis meant that two separate Fab libraries were initially constructed that sampled mutational diversity in either the heavy or light chain v-domain sequences in combination with the cognate paired grafted v-domain. Both VH and VL libraries were separately ligated into a phage display vector and transformed into E. coli via electroporation to generate $1.06 \times 10^9$ and $8.73 \times 10^8$ independent clones, respectively. Library build quality was verified by sequencing 96 clones per library. This sequencing data showed that the positions encoding either the murine or human germline residue at each position of variance had been effectively sampled at a frequency of approximately 50%, or 33% in positions where 3 amino acids had been sampled. Libraries were rescued using helper phage M13 and selections performed on biotinylated human and cynomolgus monkey CSF1R-Fc proteins in multiple separate branches. After an initial round of selection, the two pools of mutated VH and VL domains were recombined into a secondary library and three further rounds of standard selection performed, plus two 'hammer-hug' rounds.

Post-selection screening (FIG. 1) and DNA sequencing revealed the presence of 598 human and cyno CSF1R-binding Fab clones that exhibited strong binding to human and cyno CSF1R in ELISA. Amongst these 598 clones, the framework sequences remained fully germline while mutations were observed in all CDRs (Table 3). Lead clones were ranked based on level of CDR germ-lining versus ELISA signals for binding to both human and cyno CSF1R-Fc. The v-domains of the 10 top clones from this ranking were then sub-cloned into IgG expression vectors for further testing as below (Table 4).

Figure 2A:
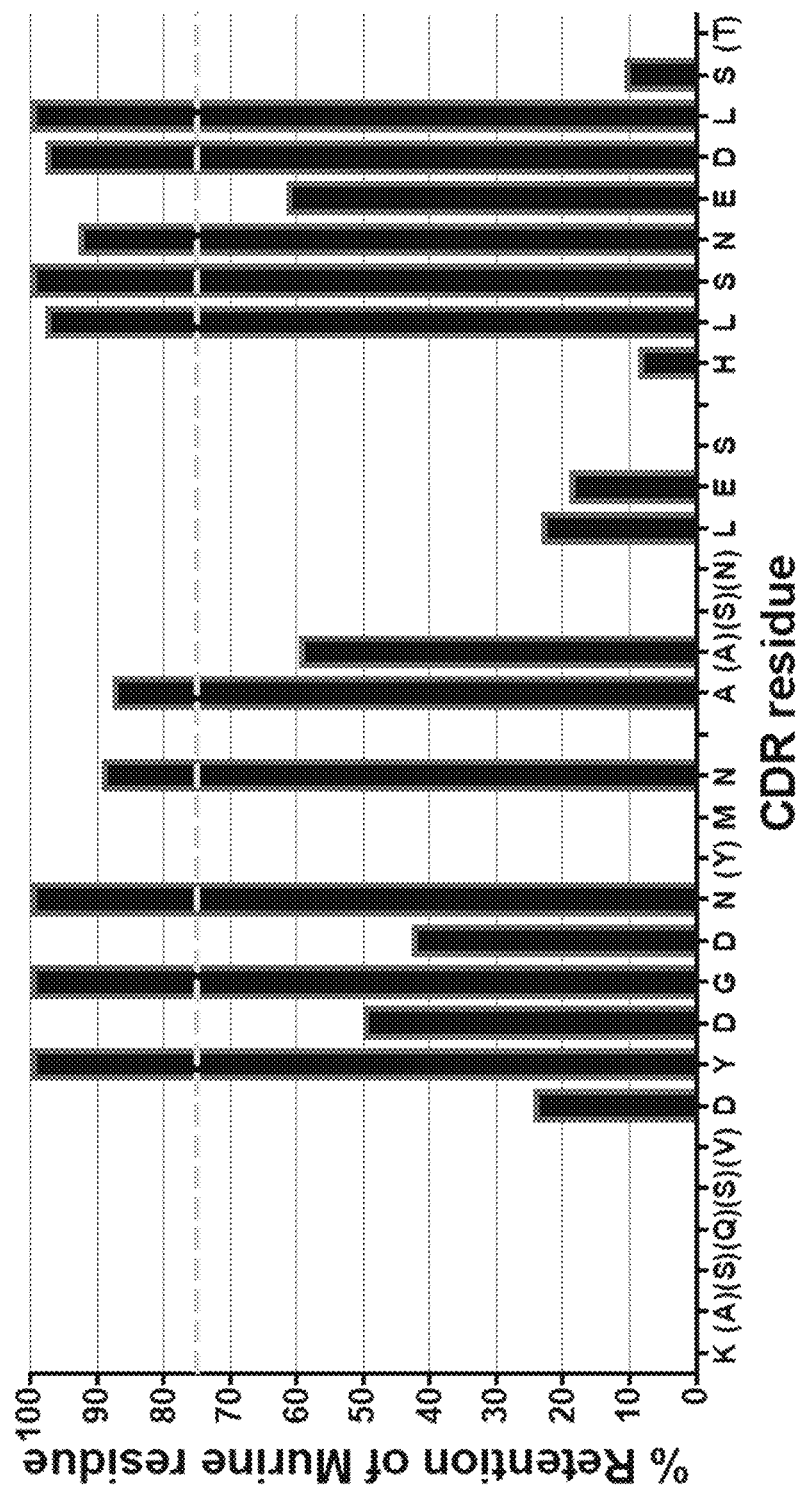
Figure 2B:
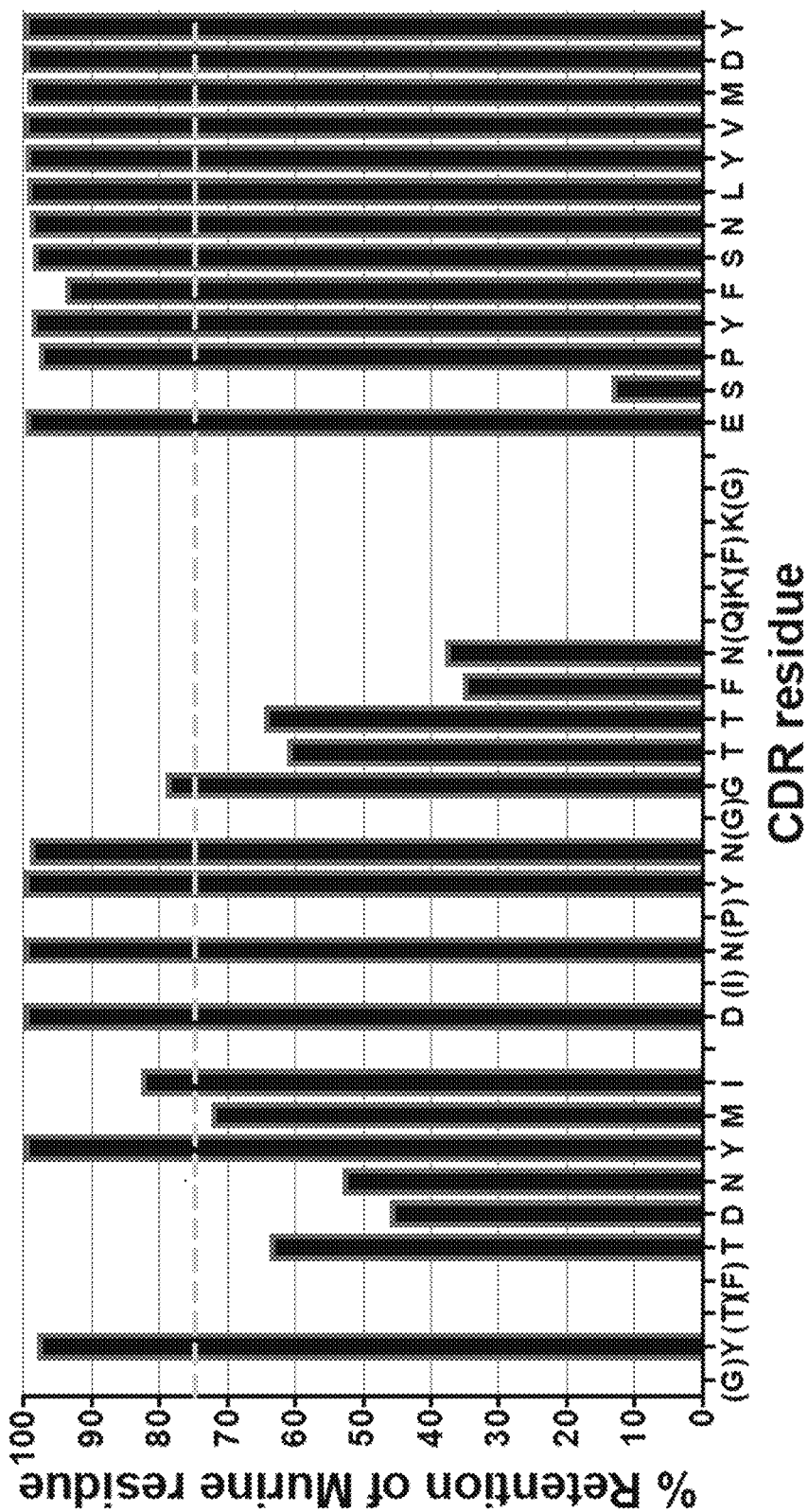

While germ-lining mutations were observed in all CDRs for the lead clones derived directly from library selections, it remained possible that sequence analyses might allow further clones to be designed to have maximal humanization. The 598 sequence-unique hits with binding signals against human and cyno protein were therefore used to analyse the retention frequency for murine amino acids in the CDRs of this functionally characterized population. Positional amino acid retention frequency was expressed as a percentage found in the $V_L$ and $V_H$ domains (FIGS. 2A&B, respectively). Murine residues with RF<75% were regarded as positions that are possibly not essential to the target-binding paratope and are likely to be open to germ-lining, in a series of combinatorial designs (Table 4). In the $V_L$ domain, only 10 of 22 murine CDR residues derived from the 0301 sequence were retained with frequencies >75% (FIG. 2A). In the $V_H$ domain (excluding the CDR-H3), only 8 of 17 murine residues in the CDR-H1 and H2 exhibited retention frequency above 75% (FIG. 2B). Importantly, the DG amino acid motif at positions 9 and 10 in the LCDR1 of hu0301 is a high risk for isomerization and resulting structural instability. The data in FIG. 2A and the sequence diversity shown in Table 3 demonstrated clearly that this motif could likely be replaced with sequences of higher chemical stability, such as EG, QG.

Designs containing only those murine residues with RF>75% were given the prefix "MH" (MH=Maximally Humanized). In total, 9 designer $V_H$ and 3 designer $V_L$ domains were generated (MH1-MH9, Table 4). The MH clones were generated by gene synthesis and (along with the 10 library-derived clones outlined above and positive controls mu0301 and hu0301), cloned into human expression vectors for production in IgG4(S228P) format. All IgGs were readily expressed and purified from transient transfections of mammalian cells.

Lead IgG Specificity and Potency Characteristics

Figure 3A:
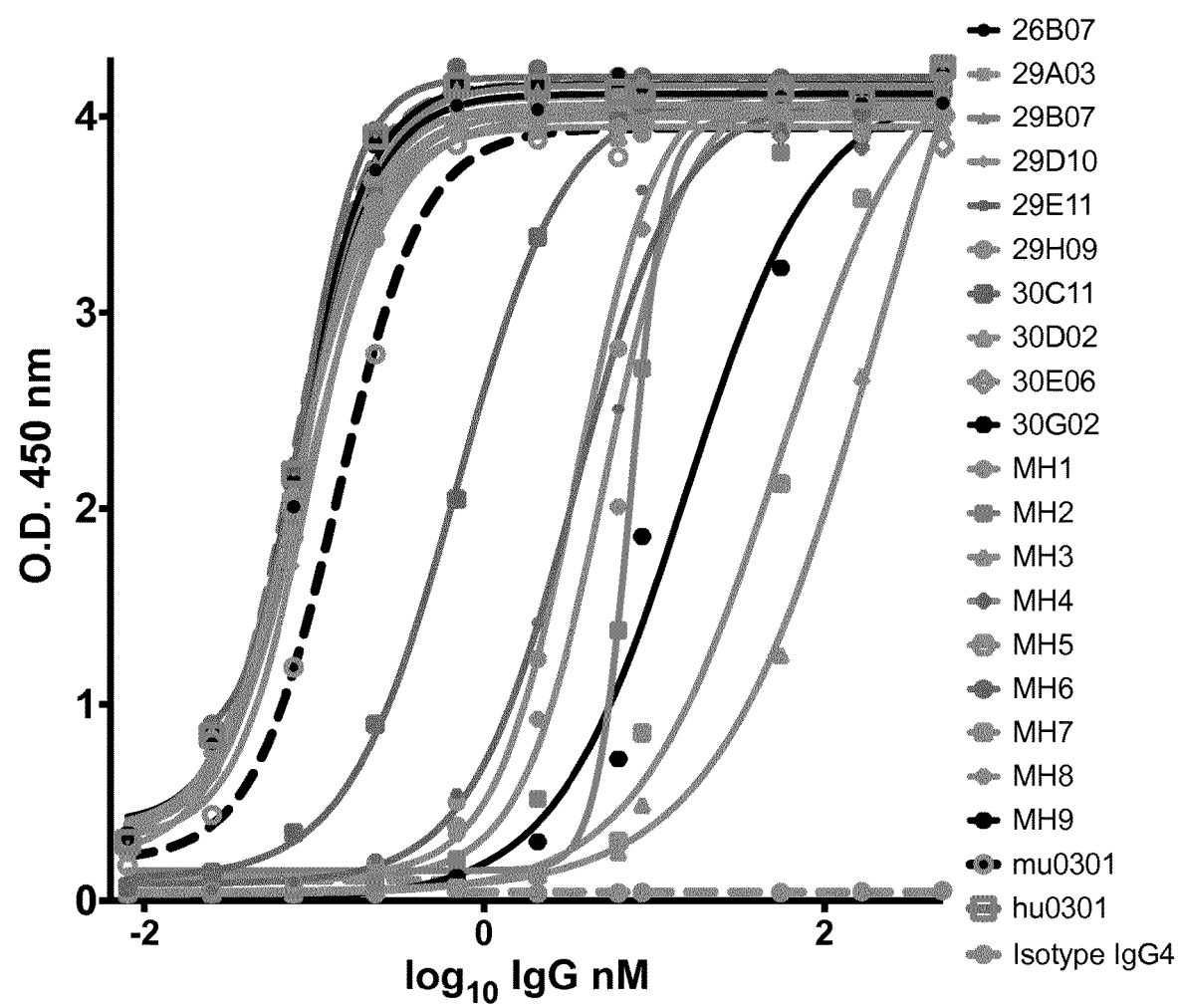
Figure 3B:
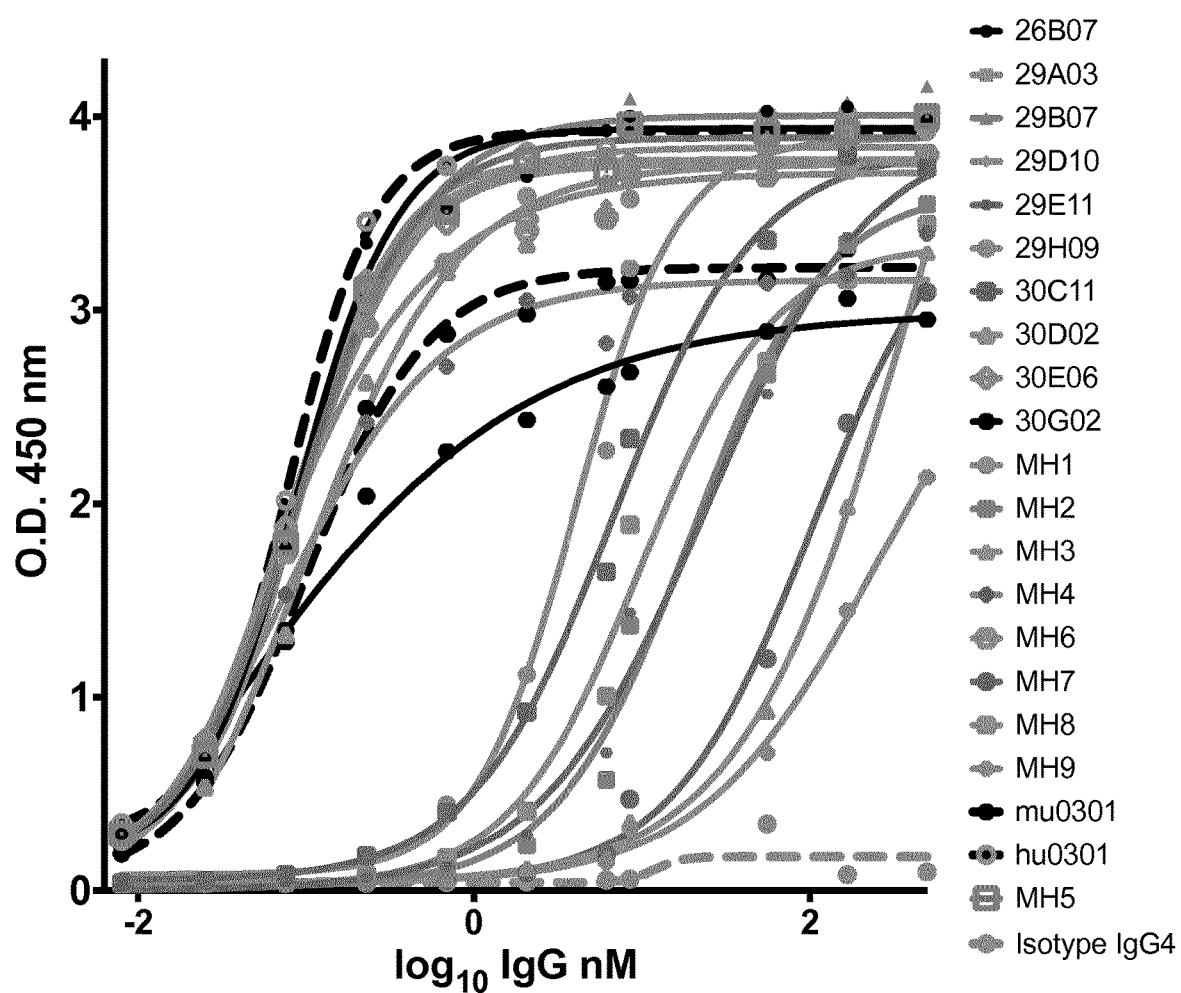
Figure 4:
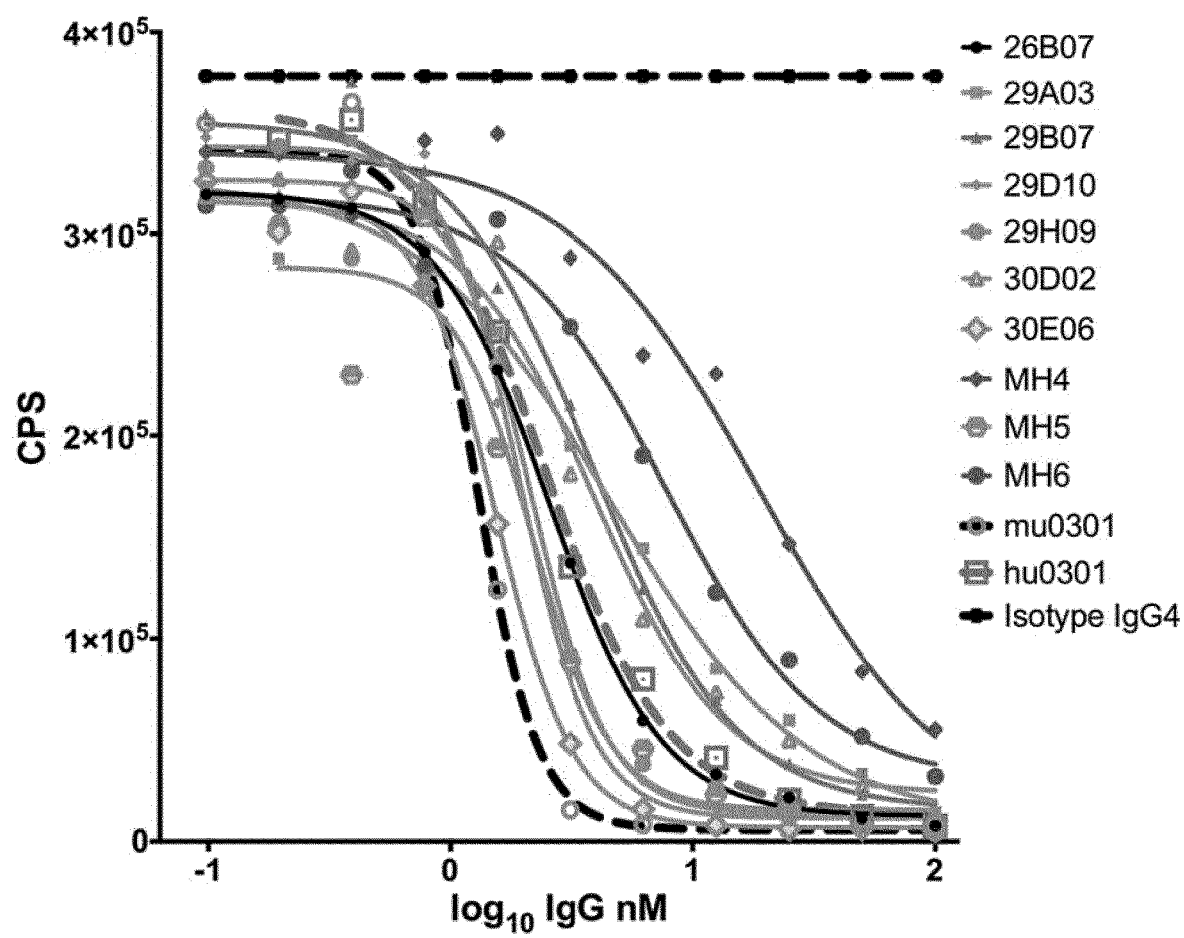
Figure 5A:
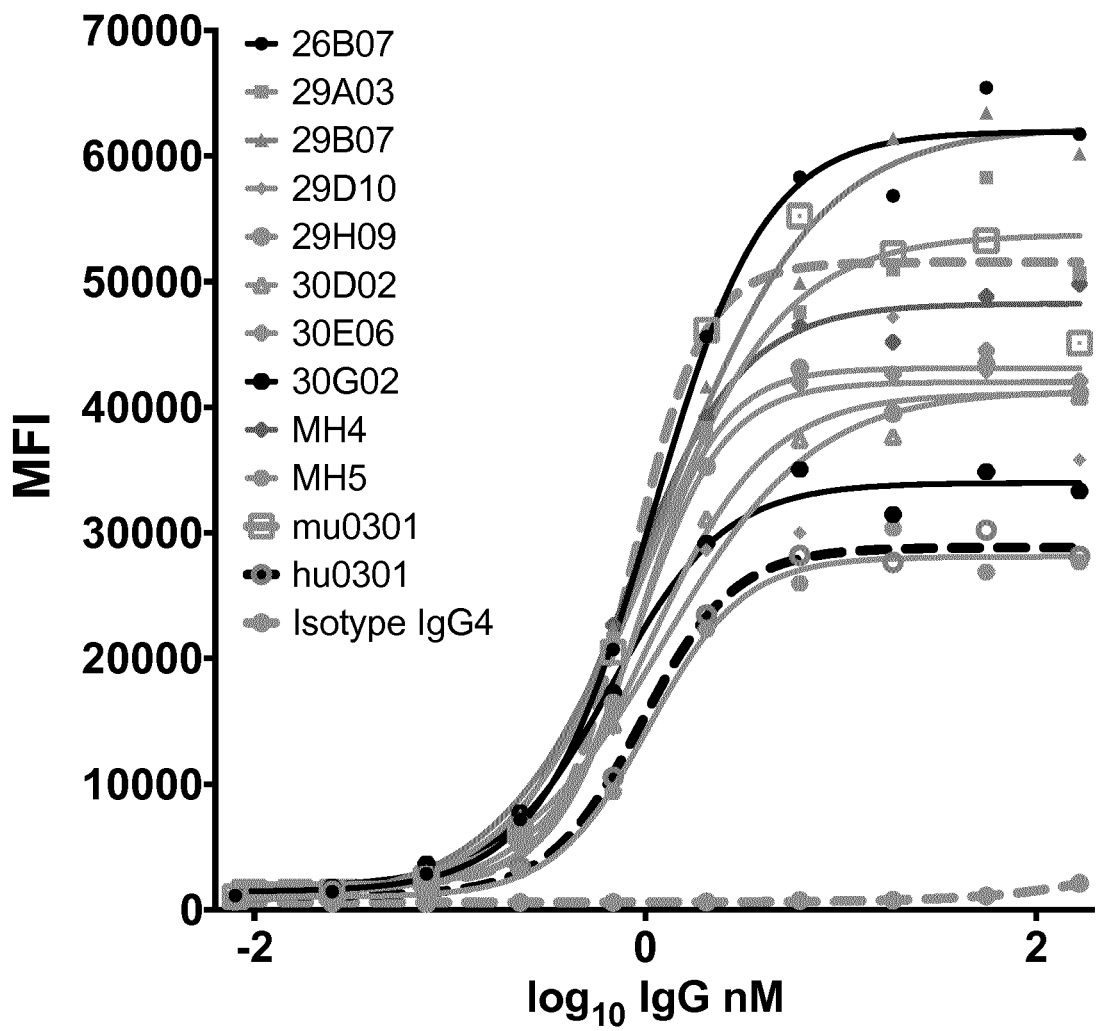
Figure 5B:
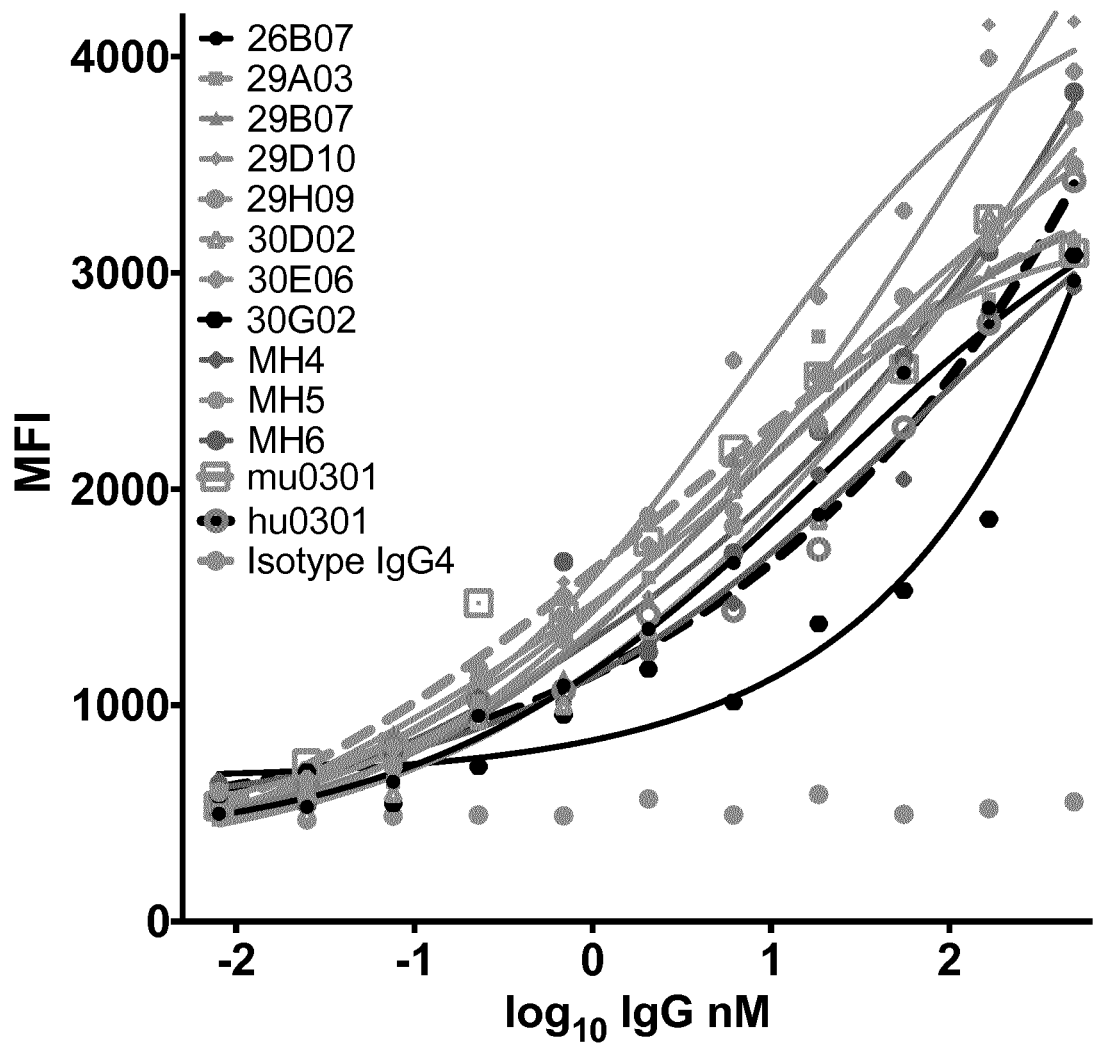
Figure 6A:
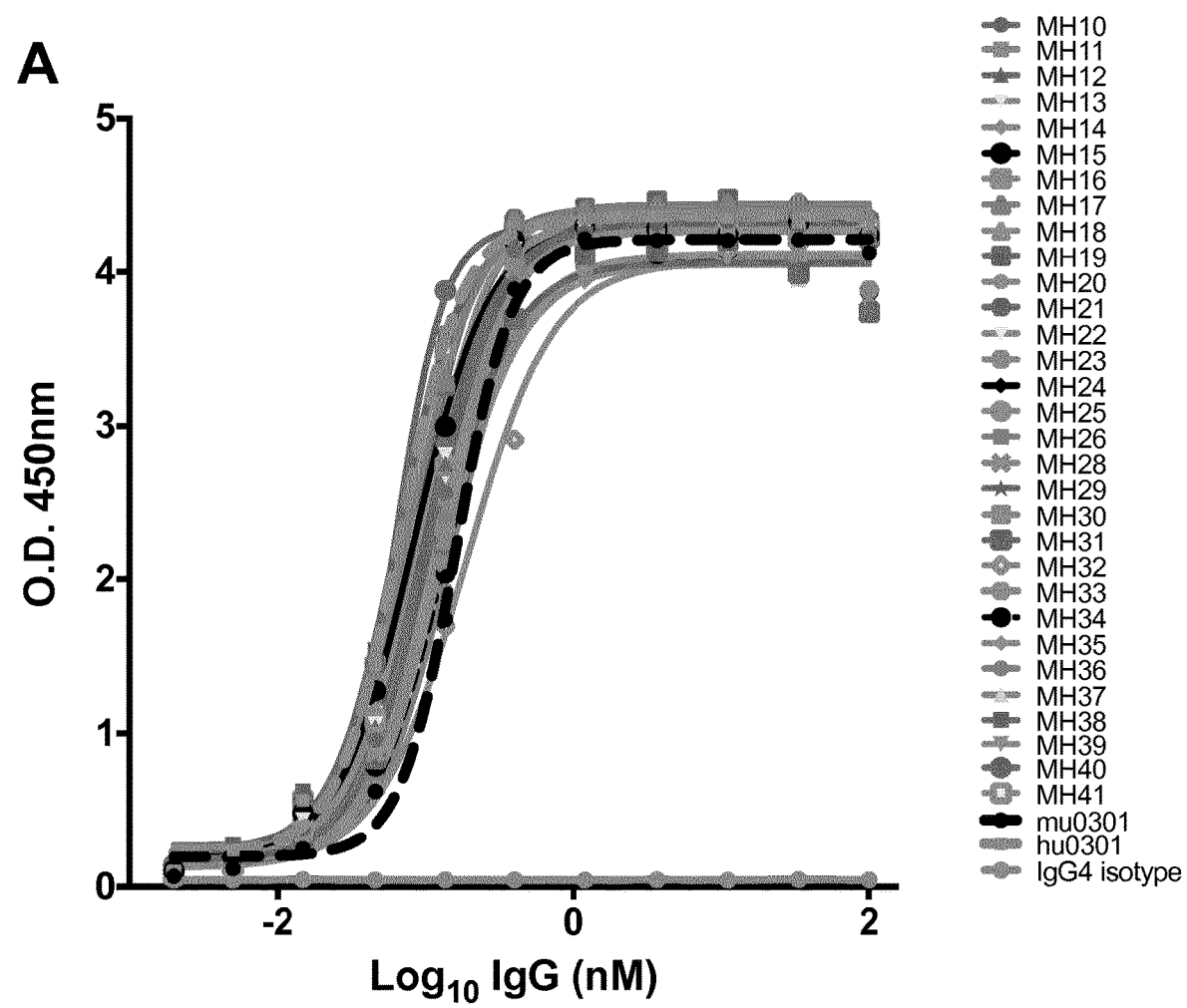
Figure 6B:
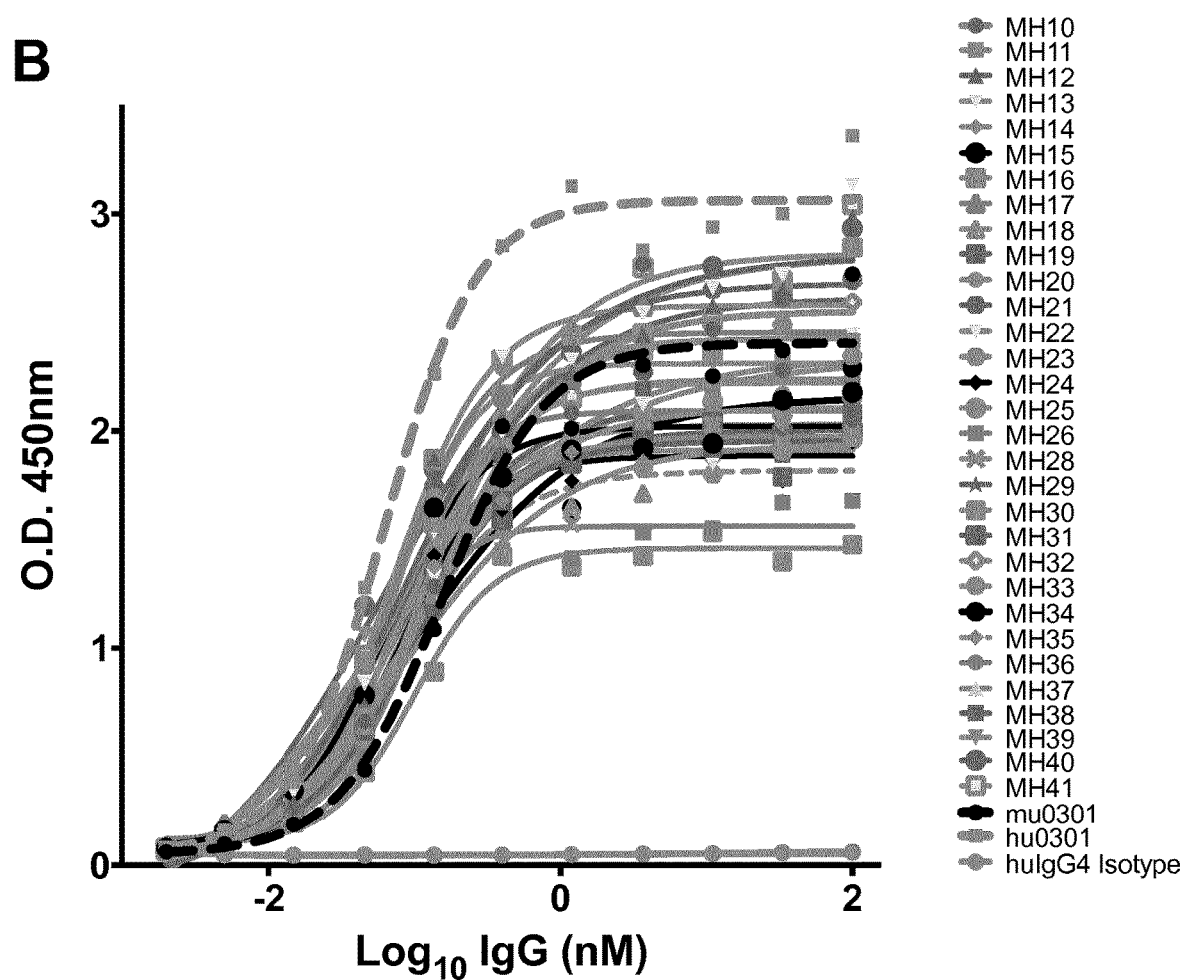
Figure 7:
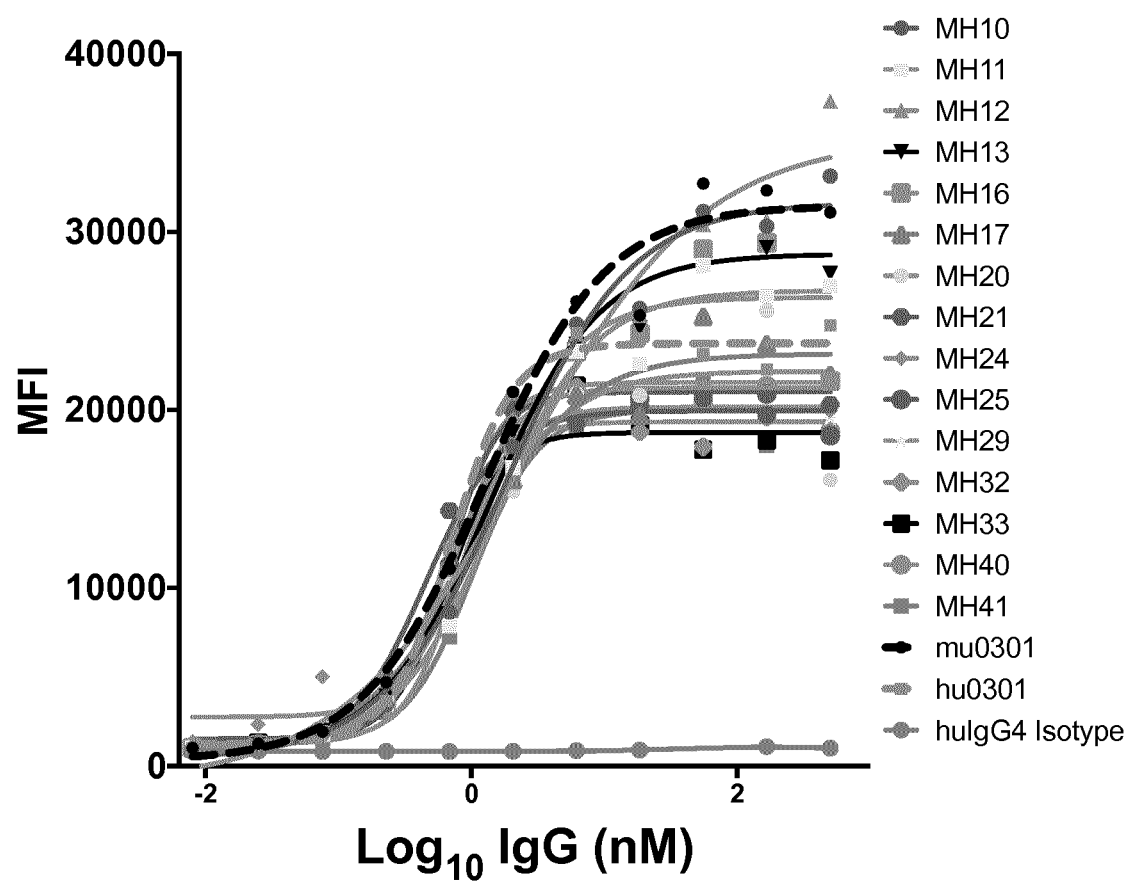
Figure 8:
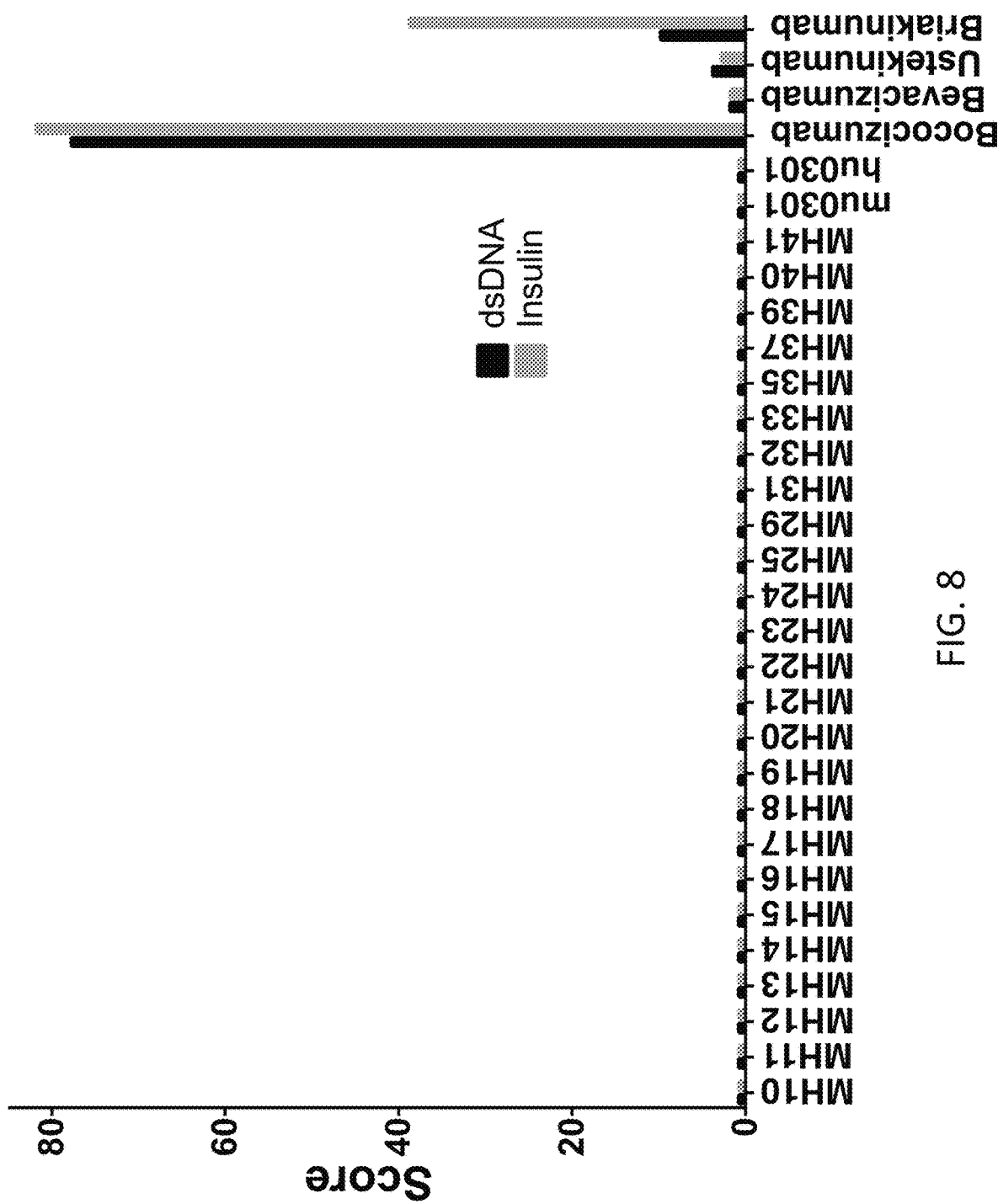
Figure 9A:
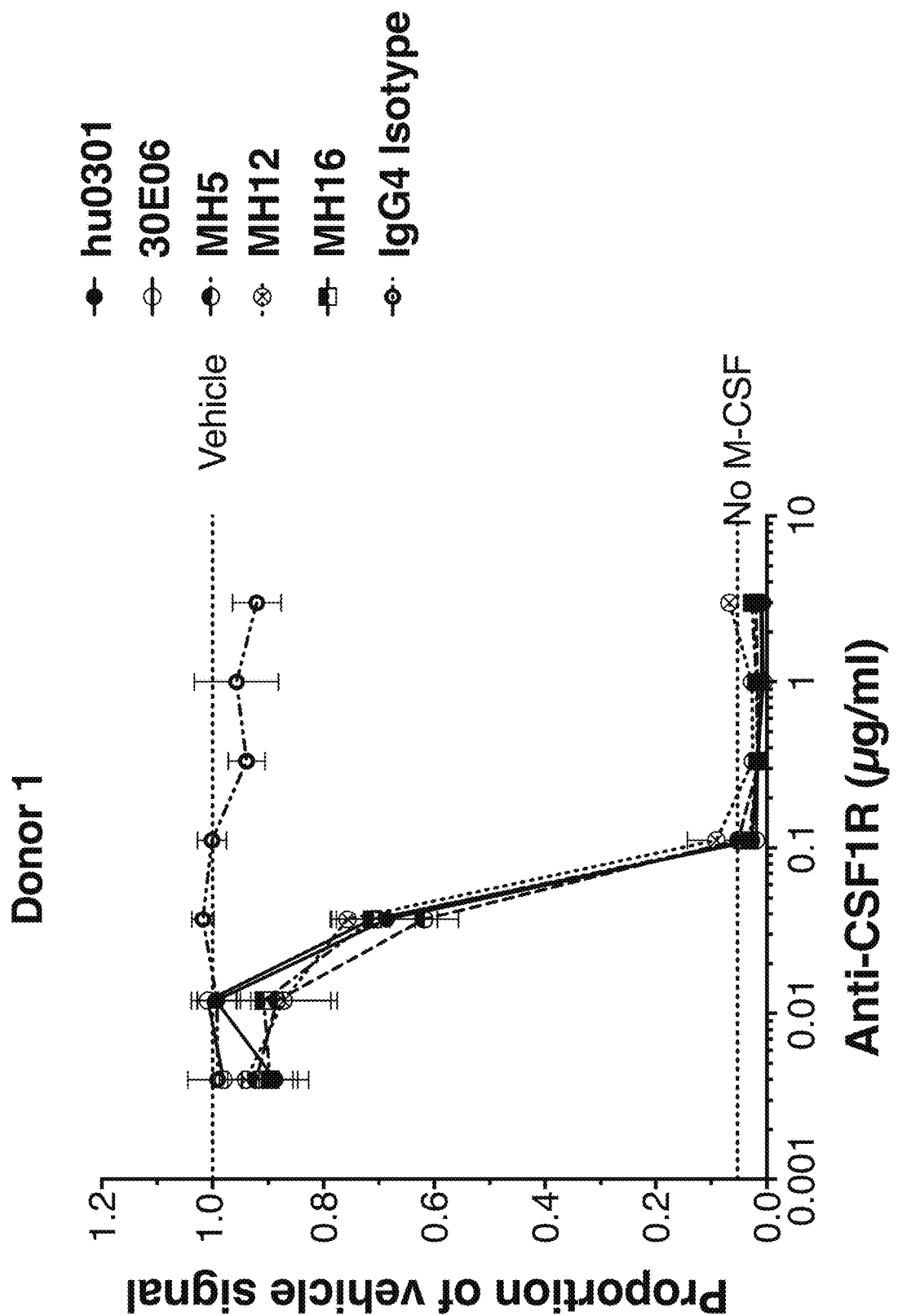
Figure 9B:
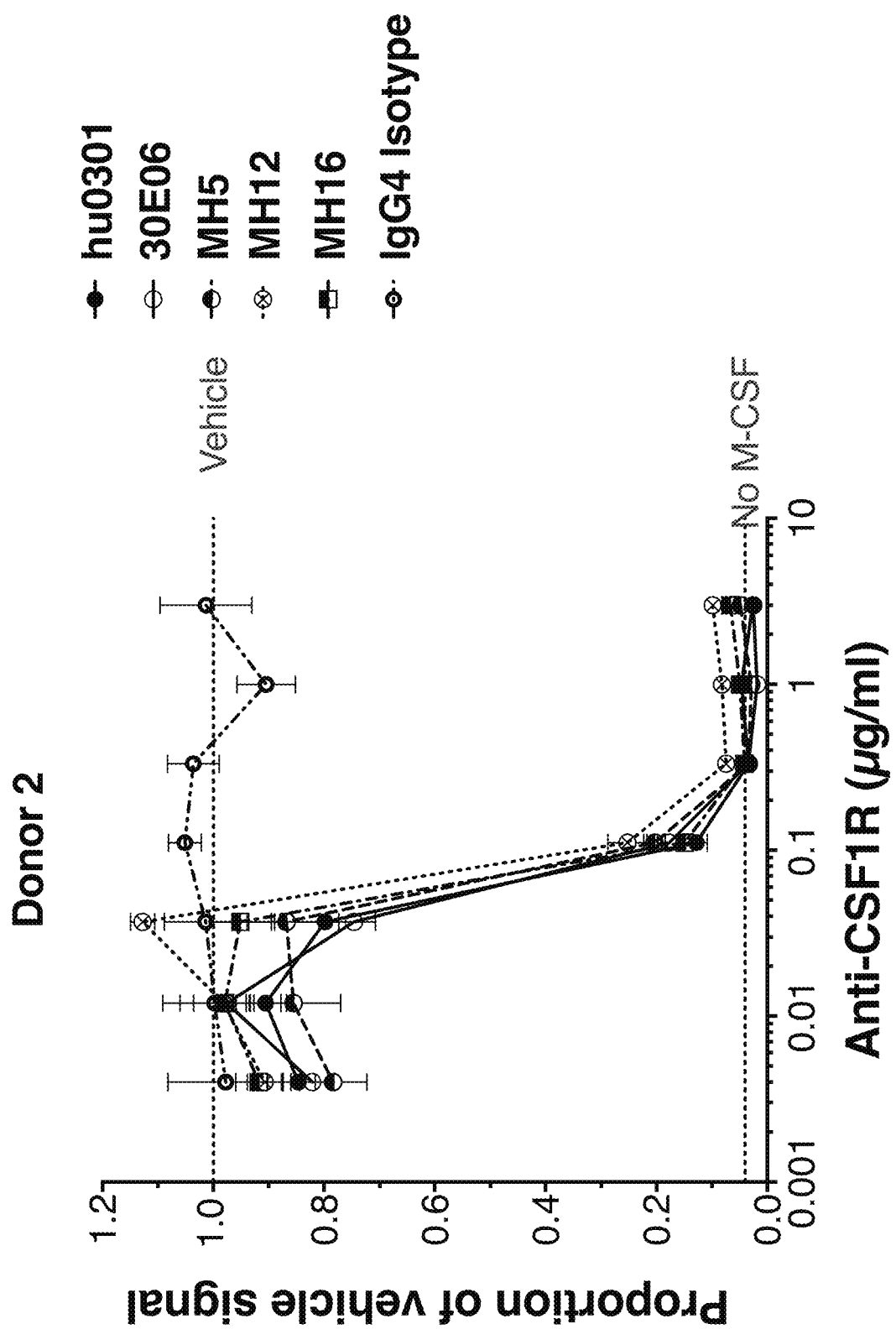
Figure 9C:
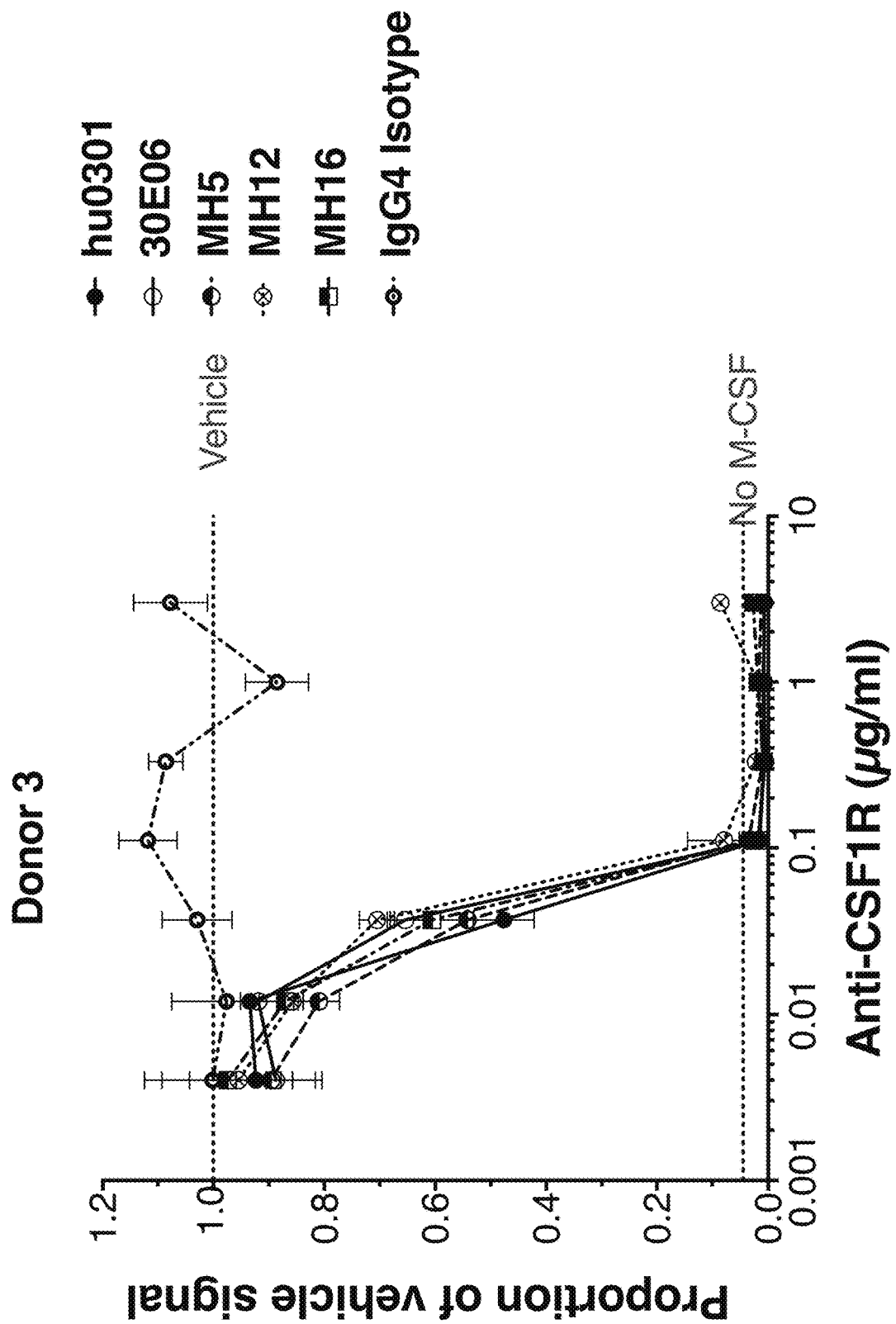

The purified IgGs described above were then tested for binding to human and cyno CSF1R-Fc in direct titration ELISA format. This analysis demonstrated that several library-derived clones had human and cyno CSF1R binding profiles overlapping with, or improved over, mu0301 (FIGS. 3A&B). Notable exceptions were clones MH1-3, MH7-9, 30C11 and 29E11, all of which exhibited poor binding to both orthologs of CSF1R, demonstrating that the CDR mutations found in these designer and library-derived clones are disruptive to binding when used in combination. As the ELISA EC50 values for directly-binding IgGs are strongly influenced by avidity, rather than true 1:1 binding affinity, we then proceeded to perform higher-sensitivity, solution-phase epitope competition and Biacore binding affinity determinations, as outlined below.

An Alphascreen assay was established to allow the testing of IgGs for epitope competition with mu0301 binding to biotinylated monomeric human CSF1R. In this assay, the top-performing library-derived and designer IgGs were more effectively differentiated via IC50 values (Table 5). While the majority of clones exhibited equivalent or improved competition for the 0301 epitope over hu0301 (FIG. 4), two further designer clones (MH4 and MH6) exhibited significantly reduced epitope competition (>2-fold lower than hu0301).

Biacore analyses of binding affinity were performed for all IgGs to solution-phase, monomeric human and cyno CSF1R proteins (Table 6). These analyses showed that library-derived clones which gave the highest IC50 values the Alphascreen assay also showed highest affinity binding to human and cyno CSF1R. Importantly, library-derived clones 30E06, 29H09 and 29D10 all exhibited unexpectedly improved binding affinities for both human and cyno CSF1R in comparison to hu0301. Importantly, these improvements in affinity partially normalised the human/cyno affinities for these clones to <3-fold (all KD values <0.42 nM), as opposed to hu0301, which exhibited an >3-fold differential (human KD—0.21 nM, cyno KD—0.66 nM). Affinity differentials of less than 3-fold between human and cyno target orthologs are highly beneficial in pre-clinical drug development analyses as they allow more accurate design and interpretation of e.g. monkey safety, PK and PD modelling experiments. In addition, comparison of the affinities of clones MH4, MH5 AND MH6, which shared an identical heavy chain sequence, highlighted the influence of selected light chain residues on maintaining target binding affinity, including: LCDR1 position 9 (D/E/Q), LCDR2 position 1 (D/A), and LCDR3 position 5 (E/Q). The use of the residue Q in the LCDR3 reduced the binding affinity for human CSF1R from 0.22 nM (clone MH5) to 0.88 nM (MH6), despite the retention frequency for the parental residue E being only 60% in the analysis shown in FIG. 2A. The use of the residues Q in the LCDR1, D in the LCDR2 and Q in the LCDR3 reduced the binding affinity for human CSF1R from 0.22 nM (clone MH5) to 1.9 nM (MH4). These findings highlighted the difficulty in deciding 'a priori' which CDR residues may or may not be converted to human germline identity, when attempting to maximise the humanization level of individual clones.

Flow Cytometric Analyses of Lead IgG Binding Specificity at the Cell Membrane

Antibodies to CSF1R were analysed for concentration-dependent binding at the cell surface via flow cytometry. Initial analyses were performed on HEK-293 cells transiently-transfected with human or rhesus CSF1R. These analyses showed that lead library-derived and designer clones exhibit strong concentration-dependent binding to membrane-presented human CSF1R with binding curves overlapping with, or improved over, the hu0301 IgG (FIG. 5A). Analyses performed on rhesus CSF1R-transfected cells further confirmed that several key library-derived and designer leads also exhibited highly similar binding curves that overlapped with, or improved over, the hu0301 IgG (FIG. 5B). No binding signals were observed for any clone on untransfected HEK-293 cells.

Antibody v-Domain T Cell Epitope Analyses

In silico technologies (Abzena, Ltd.), which are based on identifying the location of T cell epitopes in therapeutic antibodies and proteins, were used for assessing the immunogenicity of both the hu0301 and lead antibody v-domains. Analysis of the v-domain sequences was performed with overlapping 9mer peptides (with each overlapping the last peptide by 8 residues) which were tested against each of the 34 MHC class II allotypes. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score >0.6), such peptides were defined as 'high affinity' MHC class II binding peptides which are considered a high risk for containing CD4+ T cell epitopes. Low affinity MHC class II binding peptides bind a high number of alleles (>50%) with a binding score >0.55 (but without a majority >0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+(previously identified epitope in TCED™ database), and Germline Epitope ('GE'—human germline peptide sequence with high MHC Class II binding affinity). Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

Figure 10:
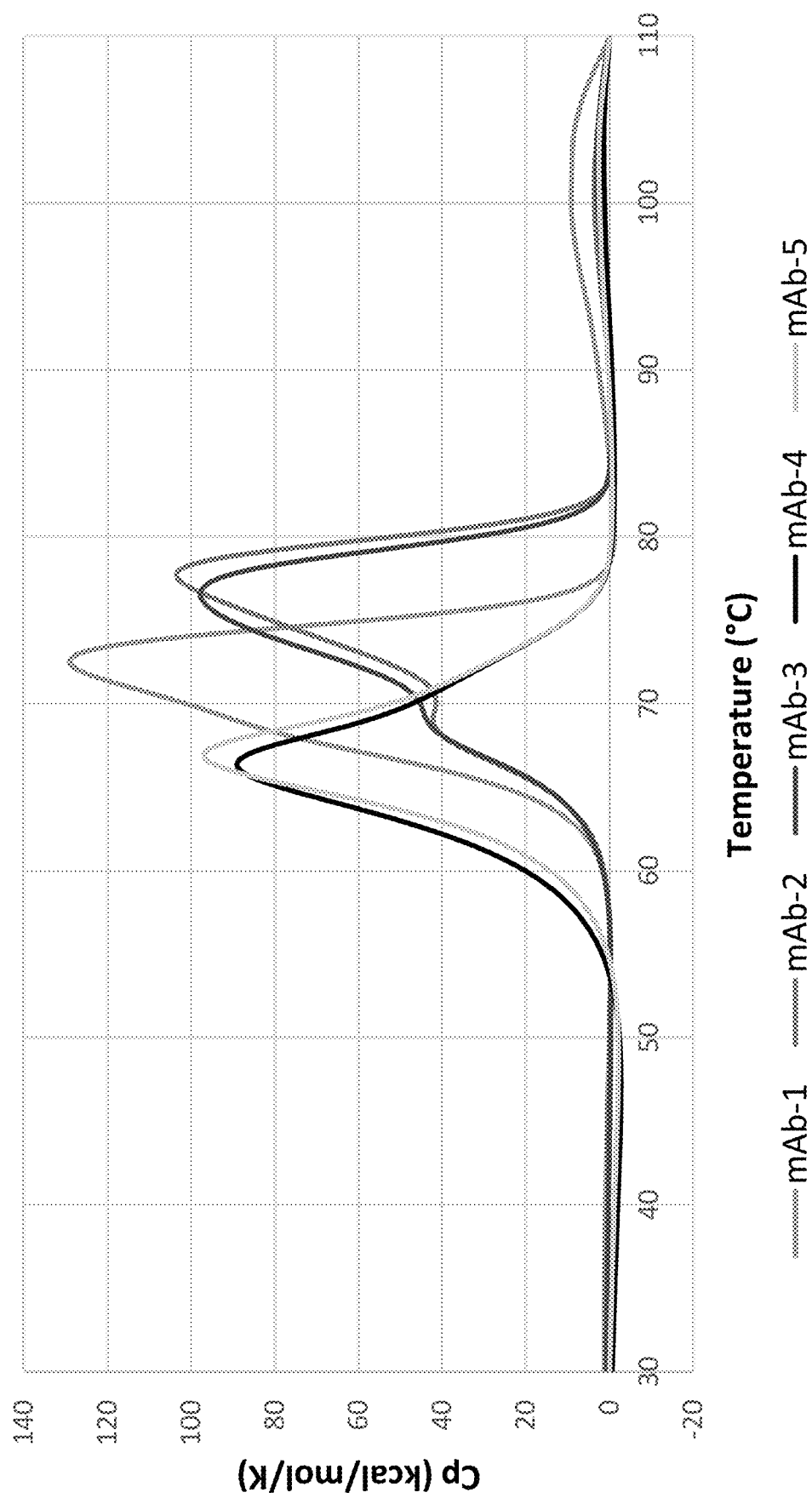

As shown in Table 7, key lead v-domains exhibited significant beneficial changes in peptide epitope content in comparison to hu0301. As the v-domain engineering process undertaken here had successfully selected for antibodies that maintained anti-CSF1R potency despite germlining many of the murine CDR residues included in the v-domains of hu0301 (Table 2), multiple epitopes found in the heavy and light chain v-domains of hu0301 could be ablated in library-derived and designer leads (Table 7). GE epitope content was also found to be increased (from 8 to ≥9 in all leads), and TCED+ epitope content was reduced or eliminated in all leads other than clone 30E06 (Table 7). Importantly, multiple foreign epitopes were eliminated by germlining mutations found in the CDRs of lead clones. For example, a TCED+ and LAF peptide 'FAVYYCHLS' (SEQ ID NO:75) found in the Framework 3/LCDR-3 of hu0301 was eliminated in all lead clones by the non-conservative, germlining mutation H>Q at position 7. Similarly, for all clones other than 30E06, the TCED+ and LAF peptide 'IYAASNLES' (SEQ ID NO:76) which spans the Framework 2/LCDR-2 sequence was ablated by the germlining mutation L>R at position 7. Surprisingly, the stabilising mutations found in the LCDR-1 of all lead clones (replacing aspartic acid residues, which are mutations away from the IGKV1-16 germline), were not found to encode any GE, HAF or LAF epitopes in that region. The mutation and reselection process had therefore successfully identified non-germline, non-murine residues in the LCDR-1 that minimised development risk, maintained potency and did not raise immunogenicity risk. In the VH region of hu0301, the peptide sequence 'FKGRVTITA' (SEQ ID NO:77) (spanning the HCDR-2 and Framework 3 regions) was found to be a LAF. The germlining mutation K>Q at position 2, found in all leads (Table 4), eliminated this risk and converted the peptide sequence into a GE.

As the library selection and screening process had identified multiple novel CDR sequences (Table 3) and the analyses of these sequences had allowed the definition of regions of mutagenic tolerance in the CDRs (FIG. 2A, 2B), we hypothesised that in silico exploratory mutagenesis of the CDR regions of the key lead clone MH5 could potentially identify novel derivatives of that clone which might retain its high functionality and further lower its immunogenicity risk. In the VH domain of clone MH5, a HAF epitope was found to be encoded by a 9-mer peptide beginning at position Y32 (Kabat numbering scheme) in the HCDR1. As this position was known to be highly tolerant of mutation (FIG. 2B), and in silico mutagenesis at this position demonstrated that the HAF could potentially be ablated (Table 8), it was chosen as a position to be sampled experimentally (Table 11). Also in the VH domain of clone MH5, LAF and HAF epitopes were found to be encoded at positions F99 and L100B respectively (Kabat numbering scheme), in the HCDR3/FW4 regions. As position F99 was not previously found to be tolerant of mutation (FIG. 2B), and in silico mutagenesis at position Q105 demonstrated that the higher-risk HAF at position L100B could potentially be ablated (Table 9), only Q105 was chosen as a position to be sampled experimentally (Table 11). Finally, In the VL domain of clone MH5, HAF epitopes were found to be encoded by 9-mer peptides beginning at position L46 and L47 (Kabat numbering scheme) in the FW2/LCDR2 region. As nothing was known about the tolerance of either of these positions to mutation, in silico mutagenesis at these positions and across both full 9-mers was undertaken. This analysis demonstrated that the HAF epitopes could potentially be ablated (Table 10), with positions L46, L47 and N53 being chosen as positions to be sampled experimentally (Table 11).

Deimmunized MH5 Derivatives—IgG Specificity and Potency Characteristics

The designer, MH5-derived, deimmunization mutant VH and VL domains designs described in Table 11 were gene synthesised, cloned in human IgG4-S228P expression vector format and combined for expression and purification in the matrix outlined in Table 12. These IgGs had minimised predicted T cell epitope content, as outlined in Table 13. Purified IgGs described above were then tested for binding to human and cyno CSF1R-Fc in direct titration ELISA format (FIG. 6A, 6B). This analysis demonstrated that all clones had retained human and cyno CSF1R binding profiles, but a subset of clones demonstrated reduced binding to cyno CSF1R (FIG. 6A, 6B). Antibodies that demonstrated fully retained binding to both orthologs of CSF1R were analysed for concentration-dependent binding at the cell surface via flow cytometry on HEK-293 cells transiently-transfected with human CSF1R. All clones analysed exhibited strong concentration-dependent binding to membrane-presented human CSF1R with binding curves overlapping with mu0301 and hu0301 IgGs (FIG. 7). No binding signals were observed for any clone on untransfected HEK-293 cells. Additionally, despite the significant additional mutagenesis in all clones, no binding above background was observed in 'PK-risk indicator' ELISA assays on human insulin and dsDNA, which examine the potential for polyreactivity (FIG. 8). All clones showed signals not only below the positive control antibodies Bococizumab and Briakinumab, but also below the negative control antibodies Ustekinumab and Bevacizumab.

Biacore analyses of binding affinity were performed for all high-performing IgGs to solution-phase, monomeric human and cyno CSF1R proteins (Table 13). These analyses showed that heavily deimmunized clones which performed best in ELISA and FACS analyses also showed highest affinity binding to human and cyno CSF1R. Importantly, multiple clones (such as MH12, MH13, MH24 and MH16) maintained affinity values within 2-fold of hu0301 for both human and cyno CSF1R and retained human/cyno differentials of <3-fold. Additionally, maximally deimmunized clones MH29, MH32 and MH40 still maintained affinities in the sub-nM range for both orthologs of CSF1R, proving that high potency, low immunogenicity and improved developability characteristics could be fully optimised in single clones (Table 14). The observation that some clones showed significantly reduced affinities (into the nM range) also highlighted the difficulty in deciding 'a priori' which CDR residues may or may not be mutated to human germline or non-germline identity, when attempting to maximise the deimmunisation level of individual clones.

Lead clones 30E06, MH5, MH12 and MH16 were further examined for biological potency in a human ex-vivo monocyte assay of cell proliferation driven by MCSF-CSF1R signalling (FIG. 9). In this assay, all clones were tested using monocytes derived from 3 separate human donors. In all donor analyses, clones hu0301, 30E06, MH5, MH12 and MH16 showed fully overlapping curves for blockade of MCSF-driven cell proliferation, indicating that full biological activity was retained in each example lead clone.

IgG Developability Analyses

Differential Scanning calorimetry (DSC) is used to measure thermal stability of proteins, as an indicator of overall molecular structural stability. This method was applied to clones hu0301, 30E06, MH5, MH12 and MH16, all in IgG4(S228P) format and formulated at 10 mg/ml concentration into a standard sample buffer (PBS, 100 mM L-Arginine). All IgGs tested were fully compatible with DSC analysis, presenting comparable sample homogeneity and cooperativity (FIG. 10). The measured thermal transition midpoints (Tm) for each antibody are indicated in Table 15. All five IgGs demonstrated Fab domain Tm values above 66° C., indicating that all samples had high integrity. Unexpectedly, however, Fab domain Tm values varied widely across lead IgGs, with clones MH5 and 30E06 demonstrating the highest stability in their Fab domains (Tm values 77.7° C. and 76.6° C., respectively). hu0301, in contrast, had a significantly lower stability Fab Tm value of 72.6° C. (Table 15). The significant increases in Fab stability for the MH5 and 30E06 lead antibodies over hu0301 were unexpected as the variable domain framework regions and antibody constant regions of all antibodies were near identical in sequence and all improvements were therefore mediated solely by differences in CDR sequences. In contrast, the heavily-deimmunized clones MH12 and MH16 exhibited significantly reduced thermal stability (Fab Tm 66.4 and 66.9, respectively). This finding illustrates the inability to define a priori which v-domain residues can be modified to remove t cell epitope risk, without increasing thermostability risk.

Figure 11A:
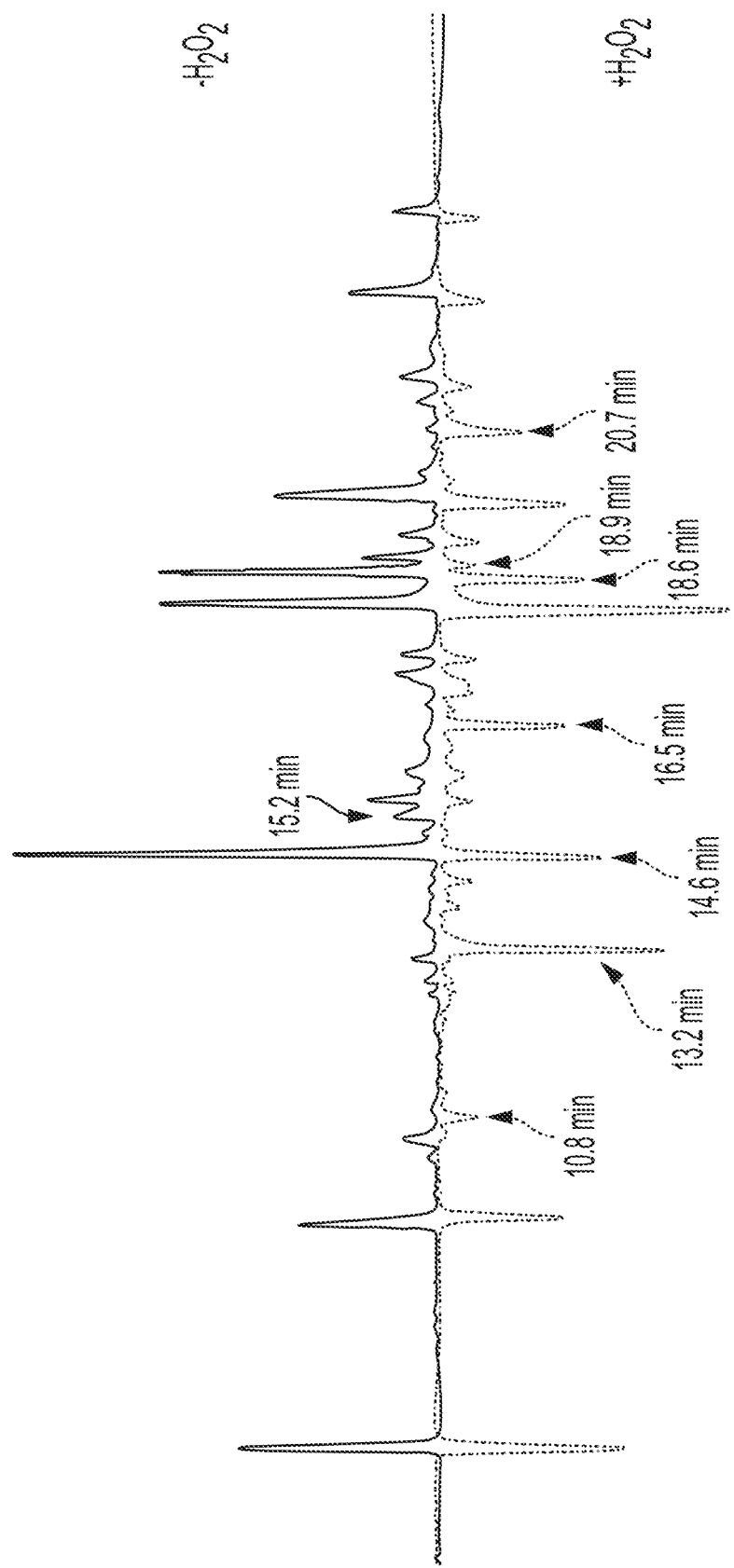
Figure 11B:
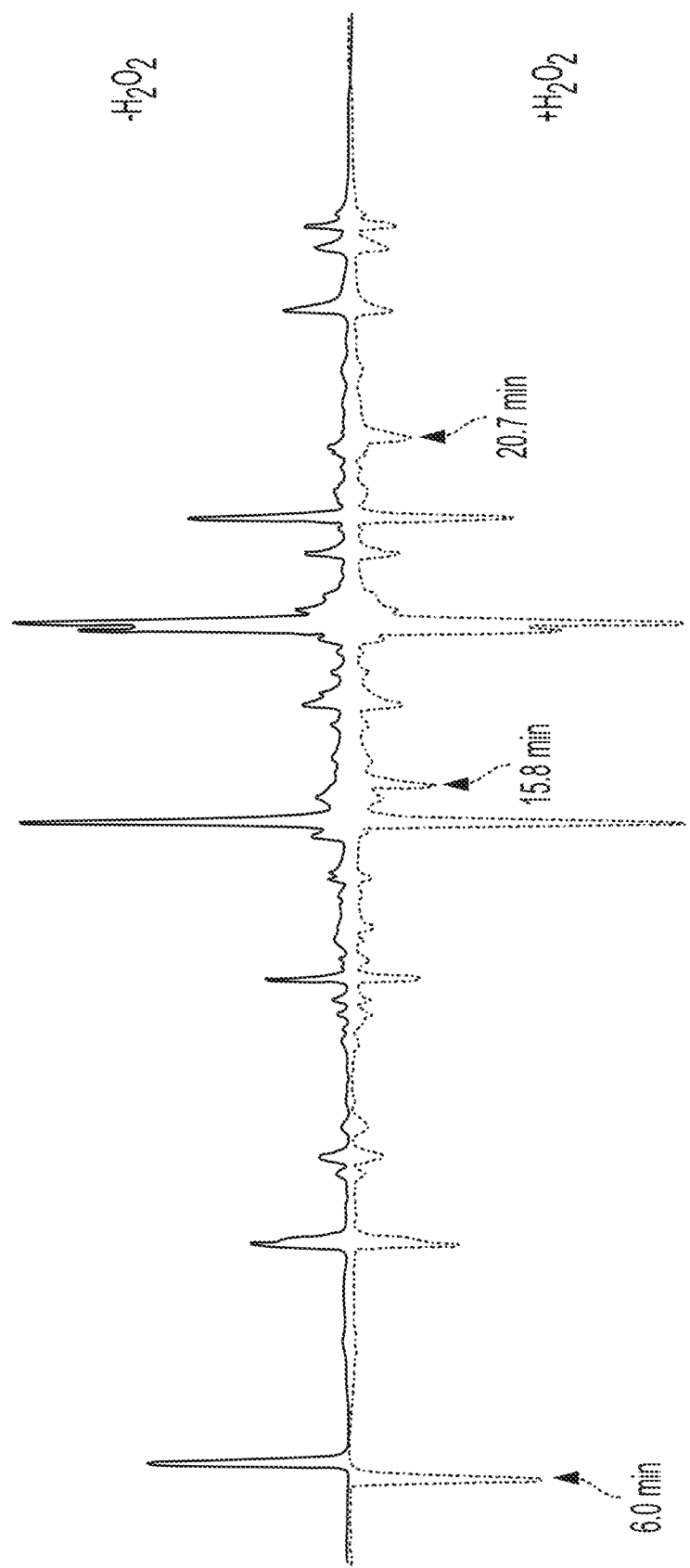
Figure 11C:
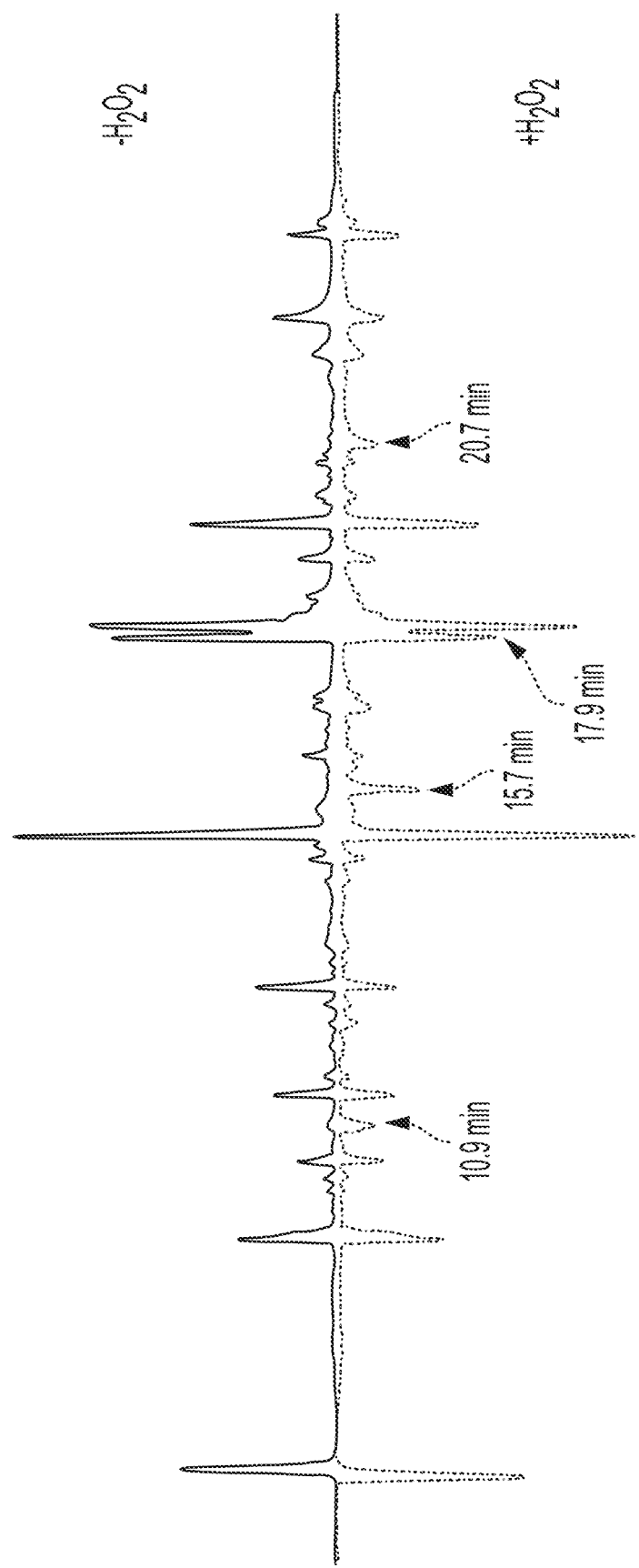
Figure 11D:
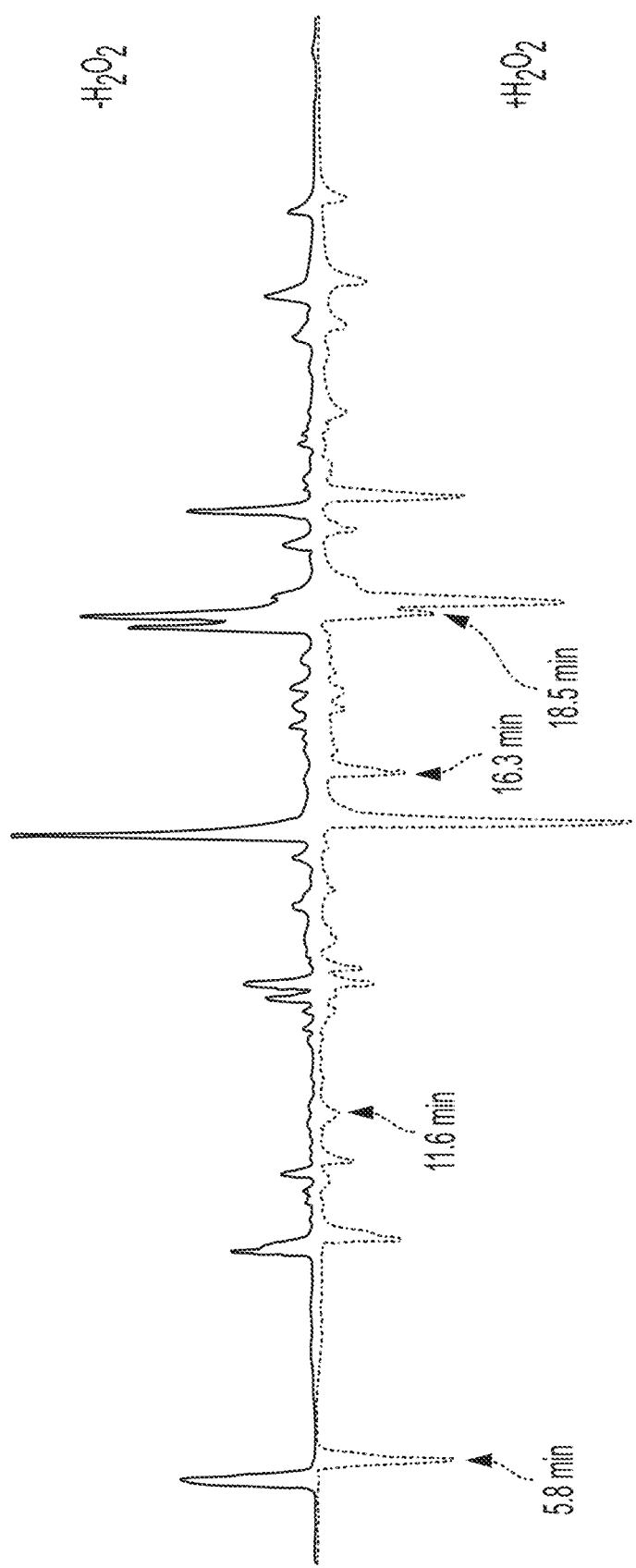
Figure 11E:
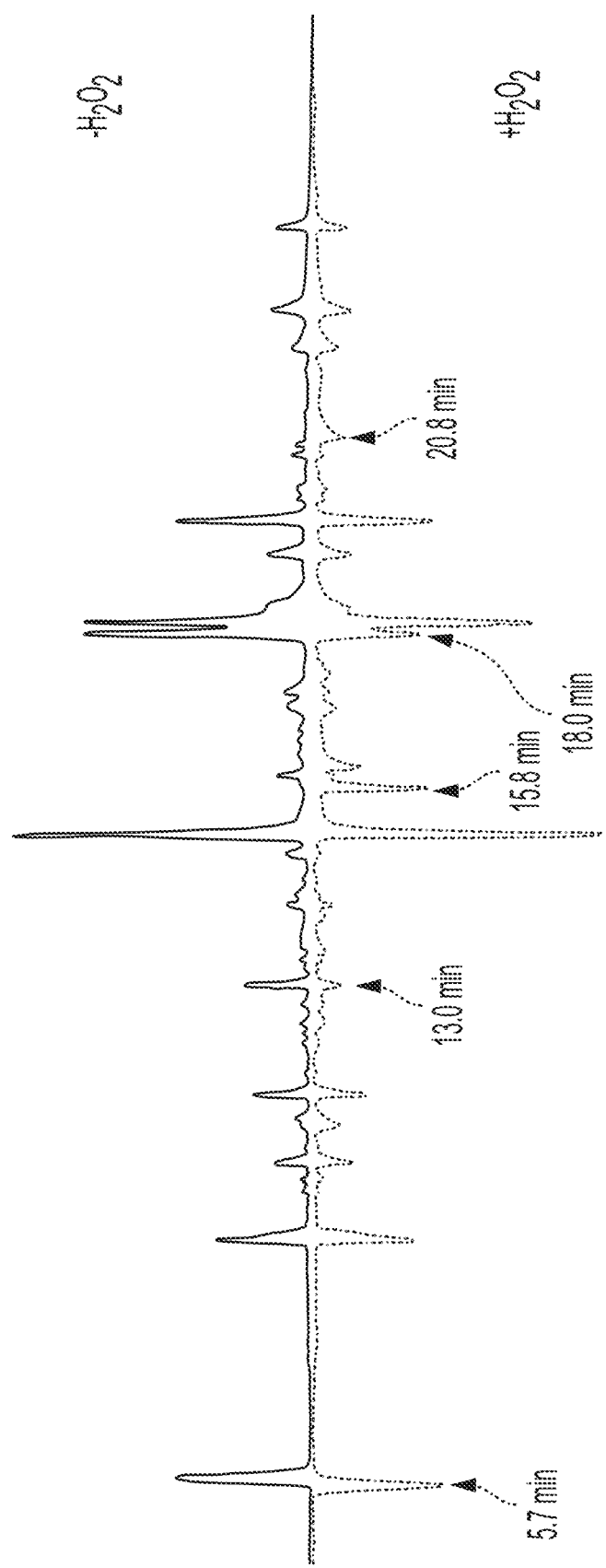

Oxidation of exposed amino acid residues, such as tryptophan and methionine, is a common degradation pathway for mAbs. Importantly, oxidation of critical side chains in the CDRs of antibodies can also potentially impact on their biological activity, by causing a reduction in target binding affinity. Oxidation is a process that usually happens over time in the storage of proteins, so the standard laboratory method of analysing oxidative risk in real time is to add an oxidative reagent to the protein. In this study, forced oxidation was applied to the IgGs by treating with 0.5% $H_2O_2$ in PBS, for 2 hours at room temperature. As oxidation can alter overall hydrophobicity of an antibody, for example by increasing the polarity of the oxidised form, potential changes induced by forced oxidation were analysed by Reverse Phase (RP) Chromatography of tryptic digest peptides. RP analysis of tryptic peptide fingerprints before and after $H_2O_2$ treatment showed that side chain oxidation changes were unexpectedly pronounced for clone hu0301. For hu0301, forced oxidation led to the modification of 8 peptides (FIG. 11A). In contrast, clones 30E06, MH5, MH12 and MH16 showed significantly fewer peptide modifications. For example, MH5 exhibited only 3 peptide modifications, all of which were minor (FIG. 11B). Clones 30E06, MH12 and MH16 exhibited 4, 4 and 5 modifications, respectively (FIG. 11C, D, E). The improvements in oxidation degradation potential observed in all of clones 30E06, MH5, MH12 and MH16, in comparison to hu0301, was unexpected as none of the lead clones had altered content of oxidation-sensitive residues in either their CDRs or v-gene framework regions in comparison to hu0301 (Tables 2, 4, 11). Indeed, as clones MH12 and MH16 were actually found to be less thermostable than hu0301 (FIG. 10), these improvements were not associated with improvements in total v-gene stability, but rather by unpredictable changes in the exposure of oxidation-sensitive side chains.

Figure 12:
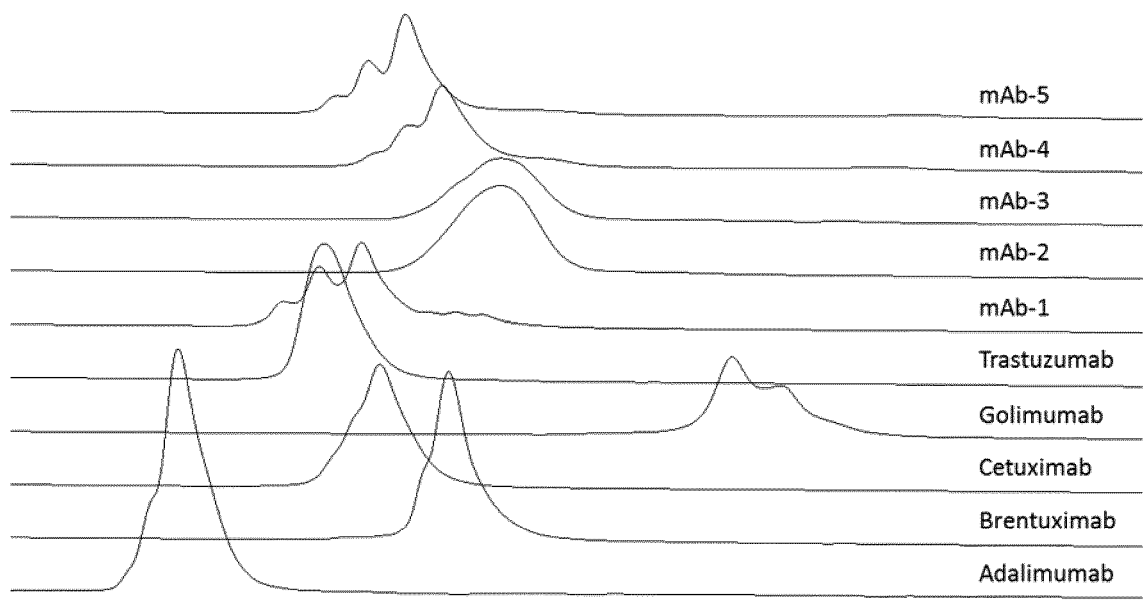

To examine the unique characteristics of the lead antibodies further, whole-IgG HIC chromatography analyses were performed. HIC chromatograms showed that all 5 lead clones eluted in the same overall range as a group of control antibodies marketed for clinical use (FIG. 12), but multiple peaks were observed for clones hu0301 (3 large and 3 small peaks, widely distributed), MH12 and MH16 (3 distinct peaks). In contrast, clones MH5 and 30E06 exhibited more uniform, single peaks (FIG. 12), indicating that the expressed proteins exhibit lower structural heterogeneity.

The combined analyses outlined herein demonstrated that, surprisingly, deep sampling of both germline and non-germline amino acids in multiple CDRs of these antibodies allowed the simultaneous optimisation of target binding specificity, immunogenicity risk, potency, biophysical stability and chemical stability risks in multiple final molecules.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

TABLE 1

Amino acid sequences murine anti-CSF1R CDRs as defined here ("Unified" scheme) in comparison to alternative definitions

| Scheme | HCDR1 | HCDR2 | HCDR3 | LCDR1 | LCDR2 | LCDR3 |
|---|---|---|---|---|---|---|
| Unified | GYTFTDNYMI (SEQ ID NO: 78) | IGDINPYNGGTTFNQKFKG (SEQ ID NO: 83) | ESPYFSNLYVMDY (SEQ ID NO: 90) | KASQSVDYDGDNYMN (SEQ ID NO: 94) | AASNLES (SEQ ID NO: 98) | HLSNEDLST (SEQ ID NO: 100) |
| Kabat | DNYMI (SEQ ID NO: 79) | DINPYNGGTTFNQKFKG (SEQ ID NO: 84) | ESPYFSNLYVMDY (SEQ ID NO: 90) | KASQSVDYDGDNYMN (SEQ ID NO: 94) | AASNLES (SEQ ID NO: 98) | HLSNEDLST (SEQ ID NO: 100) |
| Chotia | GYTFTDN (SEQ ID NO: 80) | NPYNGG (SEQ ID NO: 85) | ESPYFSNLYVMDY (SEQ ID NO: 90) | KASQSVDYDGDNYMN (SEQ ID NO: 94) | AASNLES (SEQ ID NO: 98) | HLSNEDLST (SEQ ID NO: 100) |

TABLE 1-continued

Amino acid sequences murine anti-CSF1R CDRs as defined here ("Unified" scheme) in comparison to alternative definitions

| Scheme | HCDR1 | HCDR2 | HCDR3 | LCDR1 | LCDR2 | LCDR3 |
| --- | --- | --- | --- | --- | --- | --- |
| IMGT | GYTFTDNYM (SEQ ID NO: 81) | INPYNGG (SEQ ID NO: 86) | ARESPYFSNLYVMDY (SEQ ID NO: 91) | QSVDYDGDNY (SEQ ID NO: 95) | AAS | HLSNEDLST (SEQ ID NO: 100) |
| AHo | GYTFTDNYMI (SEQ ID NO: 78) | INPYNGGTTFNQKFKG (SEQ ID NO: 87) | ESPYFSNLYVMD (SEQ ID NO: 92) | ASQSVDYDGDNY (SEQ ID NO: 96) | AASNLES (SEQ ID NO: 98) | SNEDLS (SEQ ID NO: 101) |
| AbM | GYTFTDNYMI (SEQ ID NO: 78) | DINPYNGGTT (SEQ ID NO: 88) | ESPYFSNLYVMDY (SEQ ID NO: 90) | KASQSVDYDGDNYMN (SEQ ID NO: 94) | AASNLES (SEQ ID NO: 98) | HLSNEDLST (SEQ ID NO: 100) |
| Contact | TDNYMI (SEQ ID NO: 82) | IGDINPYNGGTT (SEQ ID NO: 89) | ARESPYFSNLYVMDY (SEQ ID NO: 93) | DYDGDNYMNWY (SEQ ID NO: 97) | LLIYAASNLE (SEQ ID NO: 99) | HLSNEDLS (SEQ ID NO: 102) |

TABLE 2

Amino acid sequence of murine 0301 anti-CSF1R (mu0301), humanized (hu0301) and germline grafted v-domains.

| V DOMAIN | Human germline[1] | Amino acid sequence[2] |
|---|---|---|
| Mu0301-VH | n/a | EVQLQQSGPELVRPGASVKMSCKASGYTFTDNYMIWVKQSHGKSLEWIGDINPYNGGTTFNQKFKGKATLTVEKSSSTAYMQLNSLTSEDSAVYYCARESPYYFSNLYVMDYWGQGTSVTVSS (SEQ ID NO: 103) |
| Hu0301-VH | IGHV1-69[3] | QVQLVQSGAEVKKPGSSVKVSCKASGYTFTDNYMIWVRQAPGQGLEWMGDINPYNGGTTFNQKFKGRVTITADKSTSTAYMELSSLRSEDTAVYYCARESPYYFSNLYVMDYWGQGTLVTVSS (SEQ ID NO: 104) |
| VH-graft[4] | IGHV1-69 | QVQLVQSGAEVKKPGSSVKVSCKASGYTFTDNYMIWVRQAPGQGLEWMGDINPYNGGTTFNQKFQGRVTITADESTSTAYMELSSLRSEDTAVYYCARESPYYFSNLYVMDYWGQGTLVTVSS (SEQ ID NO: 105) |
| Mu0301-VL | n/a | NIVLTQSPASIAVSLGQRATISCKASQSVDYDGDNYMNWYQQKPGQPPKLLIYAASNLESGIPARFSGSGSGTDFTLNIHPVEEEDAATYYCHLSNEDLSTFGGGTKLEIK (SEQ ID NO: 106) |
| Hu0301-VL | IGKV3-11 | EIVLTQSPATLSLSPGERATLSCKASQSVDYDGDNYMNWYQQKPGQAPRLLIYAASNLESGIPARFSGSGSGTDFTLTISSLEPEDFAVYYCHLSNEDLSTFGGGTKVEIK (SEQ ID NO: 107) |
| VL-graft[4] | IGKV3-11 | EIVLTQSPATLSLSPGERATLSCRASQSVDYDGDNYMNWYQQKPGQAPRLLIYAASNLESGIPARFSGSGSGTDFTLTISSLEPEDFAVYYCHLSNEDLSTFGGGTKVEIK (SEQ ID NO: 108) |

[1]Human germline definitions used for grafting, based on IMGT system.
[2]CDR residues are in bold and underlined.
[3]Sequence contains a residue 'K' in the framework, bold, italicised, that indicates a non-IGHV1-69*01 allelic variant of IGHV1-69.
[4]Germline grafts used for library construction, including the IGHV1-69*01 VH germline which was used for grafting and library construction. As noted above, the "unified" CDR definitions used in this manuscript are an expanded definition in comparison to the classical Kabat definition. Each sequence above shows the framework regions (FRs) and the CDRs in the following order: FR1-CDR1-FR2-CDR2-FR3-CDR3-FR4.

TABLE 3

Unique CDRs from Fab clones shown to bind human and cyno CSF1R proteins.

| LCDR1 | LCDR2 | LCDR3 | HCDR1 | HCDR2 | HCDR3 |
|---|---|---|---|---|---|
| RASQSVSYDGENYLN (SEQ ID NO: 109) | AASNLET (SEQ ID NO: 138) | QLSNQDLLT (SEQ ID NO: 36) | GYTFSSYYMI (SEQ ID NO: 31) | MGDINPYNGGTTYAQKFQG (SEQ ID NO: 42) | EGPYFGNLYVMDY (SEQ ID NO: 227) |
| RASQSVEYEGDNYLN (SEQ ID NO: 49) | AASNRAT (SEQ ID NO: 38) | HLSNEDLLT (SEQ ID NO: 144) | GYTFTSYYMI (SEQ ID NO: 41) | MGDINPYNGTTTFAQKFQG (SEQ ID NO: 196) | ESDYFSNLYVMDY (SEQ ID NO: 228) |
| RASQSVEYEGDNYLN (SEQ ID NO: 110) | AASNLAT (SEQ ID NO: 43) | QLSNEDLLT (SEQ ID NO: 39) | GYTFSSNYMI (SEQ ID NO: 50) | MGDINPYNGGTTYNQKFQG (SEQ ID NO: 197) | EVPYFSNLYVMDY (SEQ ID NO: 229) |
| RASQSVEYDGENYLN (SEQ ID NO: 111) | AASNRET (SEQ ID NO: 139) | QLSNEWLLT (SEQ ID NO: 145) | GYTFTSNYMI (SEQ ID NO: 164) | MGDINPYNGTATYAQKFQG (SEQ ID NO: 198) | EGPYFSNLYVMDY (SEQ ID NO: 33) |
| RASQSVSYEGENYLA (SEQ ID NO: 40) | DASNRAT (SEQ ID NO: 35) | QLSSEDLLT (SEQ ID NO: 56) | GYTFTDYYMI (SEQ ID NO: 165) | MGDINPYNGGTTFAQKFQG (SEQ ID NO: 199) | EDPYFSNLYVMDY (SEQ ID NO: 230) |
| RASQSVEYQGDNYLA (SEQ ID NO: 112) | DASNLAT (SEQ ID NO: 140) | QLSNEDLST (SEQ ID NO: 146) | GYTFSDNYMI (SEQ ID NO: 166) | MGDINPYNGGTNFAQKFQG (SEQ ID NO: 200) | EPPYFSNLYVMDY (SEQ ID NO: 48) |
| RASQSVDYEGDNYLN (SEQ ID NO: 113) | DASNRET (SEQ ID NO: 141) | QLSSEWLLT (SEQ ID NO: 147) | GYTFSSNYII (SEQ ID NO: 167) | MGDINPYNGGANFAQKFQG (SEQ ID NO: 41) | ESPYTSNLYVMDY (SEQ ID NO: 231) |
| RASQSVSYEGENYLN (SEQ ID NO: 37) | DASNLET (SEQ ID NO: 142) | QLSNNDLLT (SEQ ID NO: 148) | GYTFTDNYII (SEQ ID NO: 168) | MGDINPYNGGANYAQKFQG (SEQ ID NO: 32) | EPPYFRNLYVMDY (SEQ ID NO: 232) |
| RASQSVEYQGDNYLN (SEQ ID NO: 45) | GASNRAT (SEQ ID NO: 143) | QLSSQDLLT (SEQ ID NO: 149) | GYTFSDNYII (SEQ ID NO: 169) | MGDINPYNGGTTFNQKFKG (SEQ ID NO: 201) | ESPYDSNLYVMDY (SEQ ID NO: 233) |
| RASQSVEYQGENYLN (SEQ ID NO: 53) | | HLSNQDLLT (SEQ ID NO: 150) | GGTFSSNYII (SEQ ID NO: 170) | MGDINPYNGGATFAQKFQG (SEQ ID NO: 202) | ETPYFSNLYVMDY (SEQ ID NO: 234) |
| RASQSVDYDGDNYLN (SEQ ID NO: 114) | | QQSNQDLLT (SEQ ID NO: 151) | GYTFSDYYMI (SEQ ID NO: 171) | MGDINPYNGTTTFNQKFQG (SEQ ID NO: 203) | EHPYFSNLYVMDY (SEQ ID NO: 235) |
| KASQSVDYDGDNYMN (SEQ ID NO: 22) | | QLSNEWLST (SEQ ID NO: 152) | GYTFSSYYII (SEQ ID NO: 172) | MGDINPYNGGATYAQKFQG (SEQ ID NO: 47) | ESPYASNLYVMDY (SEQ ID NO: 236) |
| RASQSVSYQGENYLN (SEQ ID NO: 115) | | QLSNQWLLT (SEQ ID NO: 153) | GYTFTDYYIS (SEQ ID NO: 173) | MGDINPYNGGANYNQKFQG (SEQ ID NO: 204) | ESPYISNLYVMDY (SEQ ID NO: 237) |
| RASQSVDYDGENYLN (SEQ ID NO: 116) | | NLSNEDLLT (SEQ ID NO: 154) | GGTFSDYYMI (SEQ ID NO: 174) | MGDINPYNGGTNYNQKFQG (SEQ ID NO: 205) | EHPYSSNLYVMDY (SEQ ID NO: 238) |
| RASQSVSYQGDNYLN (SEQ ID NO: 117) | | QLSNQDLST (SEQ ID NO: 155) | GYTFTSNYII (SEQ ID NO: 54) | MGDINPYNGGTNFNQKFQG (SEQ ID NO: 206) | ESAYFSNLYVMDY (SEQ ID NO: 239) |
| RASQSVDYEGDNYLN (SEQ ID NO: 118) | | HLSNNDLLT (SEQ ID NO: 156) | GYTFTSYYII (SEQ ID NO: 46) | MGDINPYNGGATYNQKFQG (SEQ ID NO: 51) | EGPYFRNLYVMDY (SEQ ID NO: 240) |
| RASQSVDYQGENYLN (SEQ ID NO: 119) | | HLSNQDLST (SEQ ID NO: 157) | GGTFTSYYMI (SEQ ID NO: 175) | MGDINPYNGTANYNQKFQG (SEQ ID NO: 207) | EGPYFENLYVMDY (SEQ ID NO: 241) |
| RASQSVEYDGDNYLN (SEQ ID NO: 120) | | QQSNEDLLT (SEQ ID NO: 158) | GYTFTSYYIS (SEQ ID NO: 176) | MGDINPYNGGTNYAQKFQG (SEQ ID NO: 55) | ESPYHSNLYVMDY (SEQ ID NO: 242) |
| RASQSVSYDGDNYLN (SEQ ID NO: 121) | | QLSSEDLST (SEQ ID NO: 159) | GYTFTSYYMS (SEQ ID NO: 177) | MGDINPYNGTANFNQKFQG (SEQ ID NO: 208) | ESPYRSNLYVMDY (SEQ ID NO: 243) |

TABLE 3-continued

Unique CDRs from Fab clones shown to bind human and cyno CSF1R proteins.

| LCDR1 | LCDR2 | LCDR3 | HCDR1 | HCDR2 | HCDR3 |
|---|---|---|---|---|---|
| RASQSVSYDGENYLA (SEQ ID NO: 122) | HQSNEDLLT (SEQ ID NO: 160) | GYTFSSNYIS (SEQ ID NO: 178) | MGDINPYFGGTTYAQKFQG (SEQ ID NO: 209) | | ESPYHSNLYVMDY (SEQ ID NO: 244) |
| RASQSVEYEGENYLN (SEQ ID NO: 52) | QLSSNDLLT (SEQ ID NO: 161) | GYTFSSNYMS (SEQ ID NO: 179) | MGDINPYNGGATFNQKFQG (SEQ ID NO: 210) | | EGPKFSNLYVMDY (SEQ ID NO: 245) |
| RASQSVEYDGDNYLA (SEQ ID NO: 123) | QLSNNDLST (SEQ ID NO: 162) | GGTFSDNYMI (SEQ ID NO: 180) | MGDINPYNGTANYAQKFQG (SEQ ID NO: 211) | | ESLYFSNLYVMDY (SEQ ID NO: 246) |
| RASQSVSYDGDNYLA (SEQ ID NO: 124) | QQSSEDLLT (SEQ ID NO: 163) | GYTFSSYYMS (SEQ ID NO: 181) | MGDINPYNGTATYNQKFQG (SEQ ID NO: 212) | | EHPYFSQLYVMDY (SEQ ID NO: 247) |
| RASQSVEYDGENYLA (SEQ ID NO: 125) | | GYTFTDYYII (SEQ ID NO: 182) | MGDINPYNGTTTYNQKFQG (SEQ ID NO: 213) | | ESPYQSNLYVMDY (SEQ ID NO: 248) |
| RASQSVEYQGENYLA (SEQ ID NO: 126) | | GYTFTDNYIS (SEQ ID NO: 183) | MGDINPYNGTANFAQKFQG (SEQ ID NO: 214) | | ESEYFSNLYVMDY (SEQ ID NO: 249) |
| RASQSVDYQGDNYLN (SEQ ID NO: 127) | | GYTFTDNYMS (SEQ ID NO: 184) | MGDINPYNGTTTYAQKFQG (SEQ ID NO: 215) | | ENPYFSNLYVMDY (SEQ ID NO: 250) |
| RASQSVSYQGENYLA (SEQ ID NO: 34) | | GYTFSSYYIS (SEQ ID NO: 185) | MGDINPYNGGANFNQKFQG (SEQ ID NO: 216) | | EIPYFSNLYVMDY (SEQ ID NO: 251) |
| RASQSVDYDGENYLA (SEQ ID NO: 128) | | GYTFTSNYIS (SEQ ID NO: 186) | MGDINPYNGTTNYAQKFQG (SEQ ID NO: 217) | | EPPYFSNLYVIDY (SEQ ID NO: 252) |
| RASQSVSYNGDNYLN (SEQ ID NO: 129) | | GYTFSDYYIS (SEQ ID NO: 187) | MGDINPYNGTATFAQKFQG (SEQ ID NO: 218) | | ESSYFSNLYVMDY (SEQ ID NO: 253) |
| RASQSVEYHGDNYLN (SEQ ID NO: 130) | | GGTFTDYYMI (SEQ ID NO: 188) | MGDINPYNGTTNYNQKFQG (SEQ ID NO: 219) | | ESPYGSNLYVMDY (SEQ ID NO: 254) |
| RASQSVDYQGDNYLA (SEQ ID NO: 131) | | GYTFSDNYIS (SEQ ID NO: 189) | MGDINPYFGGTTYNQKFQG (SEQ ID NO: 220) | | EPPYLSNLYVMDY (SEQ ID NO: 255) |
| RASQSVDYDGDNYLA (SEQ ID NO: 132) | | GYTFTDYYMS (SEQ ID NO: 190) | MGDINPYNGTATFNQKFQG (SEQ ID NO: 221) | | EPPYFSNLYVADY (SEQ ID NO: 256) |
| RASQSVEYEGDNYLA (SEQ ID NO: 133) | | GGTFTDNYII (SEQ ID NO: 191) | MGDINPYNGTTNFNQKFQG (SEQ ID NO: 222) | | ESPYKSNLYVMDY (SEQ ID NO: 257) |
| RASQSVDYEGENYLA (SEQ ID NO: 134) | | GGTFTSNYII (SEQ ID NO: 192) | MGDINPYFGGATYAQKFQG (SEQ ID NO: 223) | | EGPYRSNLYVMDY (SEQ ID NO: 258) |
| RASQSVEYEGENYLA (SEQ ID NO: 135) | | GYTFTSNYMS (SEQ ID NO: 193) | MGDINPYFGTTTYAQKFQG (SEQ ID NO: 224) | | ESPRFSNLYVMDY (SEQ ID NO: 259) |
| RASQSVDYEGDNYLA (SEQ ID NO: 136) | | GYTFSDYYMS (SEQ ID NO: 194) | MGDINPYFGGATYNQKFQG (SEQ ID NO: 225) | | ESPMFSNLYVMDY (SEQ ID NO: 260) |
| RASQSVDYQGENYLA (SEQ ID NO: 137) | | GGTFTDYYIS (SEQ ID NO: 195) | MGDINPYNGTTNFAQKFQG (SEQ ID NO: 226) | | EYPYFSNLYVMDY (SEQ ID NO: 261) |
| | | | | | EGPYQSNLYVMDY (SEQ ID NO: 262) |

TABLE 3-continued

Unique CDRs from Fab clones shown to bind human and cyno CSF1R proteins.

| LCDR1 | LCDR2 | LCDR3 | HCDR1 | HCDR2 | HCDR3 |
|---|---|---|---|---|---|
| | | | | | EDPYFSNLWVMDY (SEQ ID NO: 263) |
| | | | | | ESPYFSNYYVMDY (SEQ ID NO: 264) |
| | | | | | ESPPFSNLYVMDY (SEQ ID NO: 265) |
| | | | | | EGPYLSNLYVMDY (SEQ ID NO: 266) |
| | | | | | ESNYFSNLYVMDY (SEQ ID NO: 267) |
| | | | | | EGPYYSNLYVMDY (SEQ ID NO: 268) |
| | | | | | EGPYMSNLYVMDY (SEQ ID NO: 269) |
| | | | | | ESPYFSGLYVMDY (SEQ ID NO: 270) |
| | | | | | ERPYFSNLYVMDY (SEQ ID NO: 271) |
| | | | | | ESTYFSNLYVMDY (SEQ ID NO: 272) |
| | | | | | EGPYTSNLYVMDY (SEQ ID NO: 273) |
| | | | | | EGPYDSNLYVMDY (SEQ ID NO: 274) |
| | | | | | EPPYFGNLYVMDY (SEQ ID NO: 275) |
| | | | | | EGPYFDNLYVMDY (SEQ ID NO: 276) |
| | | | | | EPPYFSNSYVMDY (SEQ ID NO: 277) |
| | | | | | EGPYFSHLYVMDY (SEQ ID NO: 278) |
| | | | | | EGPYFSHLYVMDY (SEQ ID NO: 279) |
| | | | | | EPPYFSNHYVMDY (SEQ ID NO: 280) |
| | | | | | ESPYWSNLYVMDY (SEQ ID NO: 281) |

TABLE 3-continued

Unique CDRs from Fab clones shown to bind human and cyno CSF1R proteins.

| LCDR1 | LCDR2 | LCDR3 | HCDR1 | HCDR2 | HCDR3 |
|---|---|---|---|---|---|
| | | | | | EGPYESNLYVMDY (SEQ ID NO: 282) |
| | | | | | EPPYFSELYVMDY (SEQ ID NO: 283) |
| | | | | | EGPYSSNLYVMDY (SEQ ID NO: 284) |
| | | | | | DSPYFSNLYVMDY (SEQ ID NO: 285) |

TABLE 4

CDR sequences of unique, library-derived and designer, CSF1R antagonistic IgGs

| Clone name | LCDR1 | LCDR2 | LCDR3 | HCDR1 | HCDR2 | HCDR3 |
|---|---|---|---|---|---|---|
| 29D10 | RASQSVSYEGENYLN (SEQ ID NO: 37) | AASNRAT (SEQ ID NO: 38) | QLSNEDLLT (SEQ ID NO: 39) | GYTFTSYYMI (SEQ ID NO: 41) | MGDINPYNGGANFAQKFQG (SEQ ID NO: 41) | EGPYFSNLYVMDY (SEQ ID NO: 33) |
| 29B07 | RASQSVEYEGDNYLN (SEQ ID NO: 49) | AASNRAT (SEQ ID NO: 38) | QLSNQDLLT (SEQ ID NO: 36) | GYTFTSYYII (SEQ ID NO: 46) | MGDINPYNGGATYAQKFQG (SEQ ID NO: 47) | EPPYFSNLYVMDY (SEQ ID NO: 48) |
| 30C11 | RASQSVSYEGDNYLN (SEQ ID NO: 110) | AASNLET (SEQ ID NO: 138) | QLSNQDLLT (SEQ ID NO: 36) | GYTFTSNYMI (SEQ ID NO: 164) | MGDINPYNGTATYAQKFQG (SEQ ID NO: 198) | EDPYFSNLYVMDY (SEQ ID NO: 230) |
| 26B07 | RASQSVEYQGDNYLN (SEQ ID NO: 45) | AASNRAT (SEQ ID NO: 38) | QLSNEDLLT (SEQ ID NO: 39) | GYTFSSYYMI (SEQ ID NO: 31) | MGDINPYNGGANYAQKFQG (SEQ ID NO: 32) | EGPYFSNLYVMDY (SEQ ID NO: 33) |
| 29A03 | RASQSVEYEGENYLN (SEQ ID NO: 52) | AASNRAT (SEQ ID NO: 38) | QLSNQDLLT (SEQ ID NO: 36) | GYTFSSNYMI (SEQ ID NO: 50) | MGDINPYNGGATYNQKFQG (SEQ ID NO: 51) | EPPYFSNLYVMDY (SEQ ID NO: 48) |
| 29E11 | RASQSVSYDGENYLA (SEQ ID NO: 122) | AASNRAT (SEQ ID NO: 38) | QLSNEDLLT (SEQ ID NO: 39) | GYTFTSYYMI (SEQ ID NO: 41) | MGDINPYNGTATYAQKFQG (SEQ ID NO: 198) | EGPYFSNLYVMDY (SEQ ID NO: 33) |
| 30G02 | RASQSVSYQGENYLN (SEQ ID NO: 115) | AASNRAT (SEQ ID NO: 38) | QLSSEDLLT (SEQ ID NO: 56) | GYTFTSNYII (SEQ ID NO: 54) | MGDINPYNGGTNYAQKFQG (SEQ ID NO: 55) | EGPYFSNLYVMDY (SEQ ID NO: 33) |
| 30E06 | RASQSVSYEGENYLA (SEQ ID NO: 40) | AASNLAT (SEQ ID NO: 43) | QLSNEDLLT (SEQ ID NO: 39) | GYTFTSYYMI (SEQ ID NO: 41) | MGDINPYNGGTTYAQKFQG (SEQ ID NO: 42) | EGPYFSNLYVMDY (SEQ ID NO: 33) |
| 29H09 | RASQSVSYEGENYLN (SEQ ID NO: 37) | AASNRAT (SEQ ID NO: 38) | QLSNEDLLT (SEQ ID NO: 39) | GYTFTSYYMI (SEQ ID NO: 41) | MGDINPYNGGANYAQKFQG (SEQ ID NO: 32) | EGPYFSNLYVMDY (SEQ ID NO: 33) |
| 30D02 | RASQSVEYQGENYLN (SEQ ID NO: 53) | AASNRAT (SEQ ID NO: 38) | QLSNQDLLT (SEQ ID NO: 36) | GYTFSSYYMI (SEQ ID NO: 31) | MGDINPYNGGTTYAQKFQG (SEQ ID NO: 42) | EGPYFSNLYVMDY (SEQ ID NO: 33) |

TABLE 4-continued

CDR sequences of unique, library-derived and designer, CSF1R antagonistic IgGs

| Clone name | LCDR1 | LCDR2 | LCDR3 | HCDR1 | HCDR2 | HCDR3 |
|---|---|---|---|---|---|---|
| MH1 | RASQSVSYQGENYLA (SEQ ID NO: 34) | DASNRAT (SEQ ID NO: 35) | QLSNQDLLT (SEQ ID NO: 36) | GGTFSSYYII (SEQ ID NO: 286) | MGDINPYNGTANYAQKFQG (SEQ ID NO: 211) | EGPYFSNLYVMDY (SEQ ID NO: 33) |
| MH2 | RASQSVSYEGENYLN (SEQ ID NO: 37) | AASNRAT (SEQ ID NO: 38) | QLSNEDLLT (SEQ ID NO: 39) | GGTFSSYYII (SEQ ID NO: 286) | MGDINPYNGTANYAQKFQG (SEQ ID NO: 211) | EGPYFSNLYVMDY (SEQ ID NO: 33) |
| MH3 | RASQSVSYEGENYLA (SEQ ID NO: 40) | AASNRAT (SEQ ID NO: 38) | QLSNQDLLT (SEQ ID NO: 36) | GGTFSSYYII (SEQ ID NO: 286) | MGDINPYNGTANYAQKFQG (SEQ ID NO: 211) | EGPYFSNLYVMDY (SEQ ID NO: 33) |
| MH4 | RASQSVSYQGENYLA (SEQ ID NO: 34) | DASNRAT (SEQ ID NO: 35) | QLSNQDLLT (SEQ ID NO: 36) | GYTFSSYYMI (SEQ ID NO: 31) | MGDINPYNGGANYAQKFQG (SEQ ID NO: 32) | EGPYFSNLYVMDY (SEQ ID NO: 33) |
| MH5 | RASQSVSYEGENYLN (SEQ ID NO: 37) | AASNRAT (SEQ ID NO: 38) | QLSNEDLLT (SEQ ID NO: 39) | GYTFSSYYMI (SEQ ID NO: 31) | MGDINPYNGGANYAQKFQG (SEQ ID NO: 32) | EGPYFSNLYVMDY (SEQ ID NO: 33) |
| MH6 | RASQSVSYEGENYLA (SEQ ID NO: 40) | AASNRAT (SEQ ID NO: 38) | QLSNQDLLT (SEQ ID NO: 36) | GYTFSSYYMI (SEQ ID NO: 31) | MGDINPYNGGANYAQKFQG (SEQ ID NO: 32) | EGPYFSNLYVMDY (SEQ ID NO: 33) |
| MH7 | RASQSVSYQGENYLA (SEQ ID NO: 34) | DASNRAT (SEQ ID NO: 35) | QLSNQDLLT (SEQ ID NO: 36) | GYTFSSYYII (SEQ ID NO: 172) | MGDINPYNGTANYAQKFQG (SEQ ID NO: 211) | EGPYFSNLYVMDY (SEQ ID NO: 33) |
| MH8 | RASQSVSYEGENYLN (SEQ ID NO: 37) | AASNRAT (SEQ ID NO: 38) | QLSNEDLLT (SEQ ID NO: 39) | GYTFSSYYII (SEQ ID NO: 172) | MGDINPYNGTANYAQKFQG (SEQ ID NO: 211) | EGPYFSNLYVMDY (SEQ ID NO: 33) |
| MH9 | RASQSVSYEGENYLA (SEQ ID NO: 40) | AASNRAT (SEQ ID NO: 38) | QLSNQDLLT (SEQ ID NO: 36) | GYTFSSYYII (SEQ ID NO: 172) | MGDINPYNGTANYAQKFQG (SEQ ID NO: 211) | EGPYFSNLYVMDY (SEQ ID NO: 33) |

TABLE 5

Alphascreen IC50 values of anti-CSF1R IgGs.

| Clone ID | IC50 nM |
|---|---|
| mu0301 | 1.29 |
| hu0301 | 2.38 |
| 30E06 | 1.53 |
| 29D10 | 1.93 |
| 29H09 | 2.16 |
| MH5 | 2.18 |
| 26B07 | 2.56 |
| 29B07 | 3.86 |
| 30D02 | 3.92 |
| 29A03 | 4.60 |
| MH6 | 7.74 |
| MH4 | 18.94 |

TABLE 6

Biacore affinity values for IgG binding to human and cyno monomeric CSF1R.

| Clone name | Human CSF1R | | | Cyno CSF1R | | |
|---|---|---|---|---|---|---|
| | Ka (1/Ms) | Kd (1/s) | KD (nM) | ka (1/Ms) | kd (1/s) | KD (nM) |
| mu0301 | 2.90E+06 | 6.90E−05 | 0.024 | 7.40E+05 | 7.40E−05 | 0.1 |
| hu0301 | 2.30E+06 | 4.70E−04 | 0.21 | 5.00E+05 | 3.30E−04 | 0.66 |
| 30E06 | 1.90E+06 | 1.90E−04 | 0.11 | 5.70E+05 | 1.40E−04 | 0.25 |
| 29H09 | 1.80E+06 | 3.40E−04 | 0.19 | 5.50E+05 | 2.30E−04 | 0.42 |
| 29D10 | 1.90E+06 | 3.70E−04 | 0.2 | 5.20E+05 | 2.20E−04 | 0.42 |
| MH5 | 1.70E+06 | 3.60E−04 | 0.22 | 5.00E+05 | 3.10E−04 | 0.62 |
| 26B07 | 1.50E+06 | 4.20E−04 | 0.29 | 3.10E+05 | 2.60E−04 | 0.85 |
| 29B07 | 1.50E+06 | 5.10E−04 | 0.34 | 3.10E+05 | 2.50E−04 | 0.79 |
| 29A03 | 1.60E+06 | 6.00E−04 | 0.39 | 2.70E+05 | 3.20E−04 | 1.2 |
| 30D02 | 1.00E+06 | 4.90E−04 | 0.48 | 1.90E+05 | 3.20E−04 | 1.7 |
| MH6 | 1.30E+06 | 1.20E−03 | 0.88 | 5.10E+05 | 6.40E−04 | 1.3 |
| MH4 | 1.30E+06 | 2.40E−03 | 1.9 | 4.70E+05 | 1.40E−03 | 2.9 |
| 30G02 | 1.20E+06 | 8.80E−03 | 7.2 | 4.70E+05 | 6.20E−03 | 13.2 |

TABLE 7

Human T cell epitope content in v-domains predicted by iTOPE ™ and TCED ™.

| Clone Name | Germline epitopes | Low Affinity Foreign | High Affinity Foreign | TCED+ |
|---|---|---|---|---|
| hu0301 | 8 | 4 | 3 | 2 |
| 30E06 | 9 | 2 | 4 | 2 |
| 29H09 | 9 | 1 | 4 | 1 |
| 29D10 | 9 | 1 | 4 | 1 |
| MH5 | 9 | 1 | 4 | 1 |
| 26B07 | 9 | 1 | 4 | 1 |
| 29B07 | 9 | 2 | 4 | 1 |
| 29A03 | 9 | 1 | 3 | 0 |
| 30D02 | 9 | 2 | 4 | 1 |
| MH6 | 9 | 2 | 4 | 1 |
| MH4 | 11 | 2 | 2 | 1 |
| 30G02 | 9 | 2 | 3 | 0 |

TABLE 8

The effect on iTope ™ scores of proposed deimmunising changes for the antibody MH5 associated with VH domain epitope with a p1 anchor at Y32 (Kabat numbering scheme).

| p1 Anchor | Sequence | MHC II Ligands | High Affinity Ligands |
|---|---|---|---|
| sY32 | YYMIWVRQA | 20 | 19 |
| | A******** | 0 | 0 |
| | D******** | 0 | 0 |
| | G******** | 0 | 0 |
| | H******** | 0 | 0 |
| | N******** | 0 | 0 |
| | S******** | 0 | 0 |
| | T******** | 0 | 0 |
| | *D***** | 18 | 10 |
| | *****G***** | 18 | 14 |
| | *****H***** | $20^{\Delta}$ | 17 |
| | *****N***** | $18^{\Delta\Delta}$ | 17 |
| | *****S***** | $19^{\Delta\Delta}$ | 19 |
| | *****T***** | $19^{\Delta\Delta}$ | 17 |
| | *****W***** | 20 | 14 |
| | *****Y***** | 20 | 15 |

Bold font in cells indicates the presence of a High Affinity Foreign T cell epitope and italic font in cells indicates the presence of a Low Affinity Foreign T cell epitope. $^{\Delta}$indicates that the core 9 mer peptide is encoded by germline sequence. $^{\Delta\Delta}$indicates that the core 9 mer peptide is encoded by a TCED ™ negative peptide. SEQ ID NOs are assigned to the sequences as shown below:

| Sequence | SEQ ID NO |
|---|---|
| YYMIWVRQA | 287 |
| AYMIWVRQA | 288 |
| DYMIWVRQA | 289 |
| GYMIWRQA | 290 |
| HYMIWVRQA | 291 |
| NYMIWVRQA | 292 |
| SYMIWVRQA | 293 |
| TYMIWRQA | 294 |
| YDMIWVRQA | 295 |
| YYMGWVRQA | 296 |
| YYMHWVRQA | 297 |
| YYMNWVRQA | 298 |
| YYMSWVRQA | 299 |
| YYMTWRQA | 300 |

TABLE 8-continued

| | |
|---|---|
| YYMWWRQA | 301 |
| YYMYWWRQA | 302 |

TABLE 9

The effect on iTope™ scores of proposed deimmunising changes for the antibody MH5 associated with the VH domain epitopes with p1 anchors at positions F99 and L100B (Kabat numbering scheme).

| p1 Anchor | Sequence | MHC II Ligands | High Affinity Ligands | P1 Anchor | Sequence | MHC II Ligands | High Affinity Ligands |
|---|---|---|---|---|---|---|---|
| F99 | FSNLYVMDYWGQ | 19 | 16 | L100B | FSNLYVMDYWGQ | 25 | 17 |
| | A********** | 0* | 0 | | A********** | 25* | 17 |
| | H********** | 0* | 0 | | H********** | 25* | 17 |
| | T********** | 0* | 0 | | T********** | 25* | 17 |
| | *D**** | 10 | 7 | | *D******** | 0 | 0 |
| | *G**** | 12$^a$ | 8 | | *G******** | 0$^a$ | 0 |
| | *H**** | 16 | 11 | | *H******** | 0 | 0 |
| | *P**** | 9 | 3 | | *P******** | 0 | 0 |
| | *Q**** | 15 | 12 | | *Q******** | 0 | 0 |
| | *R**** | 12 | 9 | | *R******** | 0 | 0 |
| | *S**** | 12 | 9 | | *S******** | 0 | 0 |
| | *T**** | 14 | 8 | | *T******** | 0 | 0 |
| | *W**** | 15 | 10 | | *W******** | 16 | 10 |
| | *Y**** | 16 | 12 | | *Y******** | 16 | 10 |
| | **D*** | 19 | 16 | | **D*** | 1 | 0 |
| | **S*** | 19 | 16 | | **S*** | 15 | 1 |
| | **W*** | 19 | 16 | | **W*** | 16 | 3 |
| | ***D** | 6 | 0 | | *D**** | 6 | 0 |
| | ****D* | 8 | 1 | | **D*** | 5 | 3 |
| | ****E* | 13 | 6 | | **E*** | 2 | 0 |
| | ****G* | 14 | 7 | | **G*** | 7 | 6 |
| | ****H* | 16 | 13 | | **H*** | 9 | 5 |
| | ****P* | 16 | 10 | | **P*** | 1 | 0 |
| | ****S* | 16 | 9 | | **S*** | 5 | 0 |
| | ****T* | 15 | 9 | | **T*** | 6 | 1 |
| | ****W* | 16 | 10 | | **W*** | 12 | 4 |
| | ********K | 19 | 16 | | ********K | 15 | 4 |
| | ********R | 19 | 16 | | ********R | 12 | 4 |

Bold font in cells indicates the presence of a High Affinity Foreign T cell epitope and italic font in cells indicates the presence of a Low Affinity Foreign T cell epitope. *Changes at this position affect the MHC ligand with p1 anchor at F99 only. **Changes at this position affect the MHC ligand with p1 anchor at L100B only. $^a$Mutation using glycine in this position was discounted to avoid introducing a potential deamidation site. SEQ ID NOs are assigned to the sequences as shown below:

| Sequence | SEQ ID NO |
|---|---|
| FSNLYVMDYWGQ | 303 |
| ASNLYVMDYWGQ | 304 |
| HSNLYVMDYWGQ | 305 |
| TSNLYVMDYWGQ | 306 |
| FSNDYVMDYWGQ | 307 |
| FSNGYVMDYWGQ | 308 |
| FSNRYVMDYWGQ | 309 |

TABLE 9-continued

| | |
|---|---|
| FSNSYVMDYWGQ | 310 |
| FSNTYVMDYWGQ | 311 |
| FSNWYVMDYWGQ | 312 |
| FSNYYVMDYWGQ | 313 |
| FSNLDVMDYWGQ | 314 |
| FSNLSVMDYWGQ | 315 |
| FSNLWVMDYWGQ | 316 |
| FSNLYDMDYWGQ | 317 |
| FSNLYVDDYWGQ | 318 |
| FSNLYVEDYWGQ | 319 |
| FSNLYVGDYWGQ | 320 |
| FSNLYVHDYWGQ | 321 |
| FSNLYVPDYWGQ | 322 |
| FSNLYVSDYWGQ | 323 |
| FSNLYVTDYWGQ | 324 |
| FSNLYVWDYWGQ | 325 |
| FSNLYVMDYWGK | 326 |
| FSNLYVMDYWGR | 327 |

TABLE 10

The effect on iTope ™ scores of proposed deimmunising changes for the antibody MH5 associated with the VL domain epitopes with p1 anchors at positions L46 and L47 (Kabat numbering scheme).

| p1 Anchor | Sequence | MHC 11 Liqands | High Affinity Ligands | P1 Anchor | Sequence | MHC 11 Ligands | High Affinity Ligands |
|---|---|---|---|---|---|---|---|
| L46 | LLIYAASNRA | 28 | 17 | L47 | LLIYAASNRA | 31 | 24 |
| | A********* | 0* | 0 | | A********* | 31* | 24 |
| | R********* | 0* | 0 | | R********* | 31* | 24 |
| | S********* | 0* | 0 | | S********* | 31* | 24 |
| | T********* | 0* | 0 | | T********* | 31* | 24 |
| | *A******** | 17 | 10 | | *A******** | 0 | 0 |
| | L***** | 24 | 13 | | L***** | 31 | 22 |
| | *H**** | 26 | 16 | | *H**** | 26 | 16 |
| | *K**** | 26 | 16 | | *K**** | 24 | 11 |
| | *S**** | 23 | 14 | | *S**** | 26 | 16 |
| | ****D***** | 28**[Δ] | 17 | | ****D***** | 23**[a] | 14 |
| | ****E***** | 28** | 17 | | ****E***** | 20** | 11 |
| | ****T***** | 28** | 17 | | ****T***** | 25** | 16 |
| | *****D**** | 9* | 4 | | *****D**** | 31* | 24 |
| | *****G**** | 17* | 12 | | *****G**** | 31* | 24 |
| | ******D*** | 17 | 9 | | ******D*** | 10 | 7 |
| | ******G*** | 23 | 16 | | ******G*** | 26 | 12 |
| | *******D** | 28** | 17 | | *******D** | 15** | 8 |
| | *******E** | 28** | 17 | | *******E** | 24** | 12 |
| | *********D | 28** | 17 | | *********D | 21** | 14 |
| | *********E | 28** | 17 | | *********E | 23** | 16 |
| | *********G | 28** | 17 | | *********G | 31** | 16 |
| | *********P | 28** | 17 | | *********P | 22** | 10 |

TABLE 10-continued

| Bold font in cells indicates the presence of a High Affinity Foreign T cell epitope and italic font in cells indicates the presence of a Low Affinity Foreign T cell epitope. *Changes at this position affect the MHC ligand with p1 anchor at L46 only. **Changes at this position affect the MHC ligand with p1 anchor at L47 only. [A]Indicates the core 9 mer peptide is encoded by germline sequence. SEQ ID NOs are assigned to the sequences as shown below: | |
|---|---|
| Sequence | SEQ ID NO |
| LLIYAASNRA | 0328 |
| ALIYAASNRA | 0329 |
| RLIYAASNRA | 0330 |
| SLIYAASNRA | 0331 |
| TLIYAASNRA | 0332 |
| LAIYAASNRA | 0333 |
| LLLYAASNRA | 0334 |
| LLIHAASNRA | 0335 |
| LLIKAASNRA | 0336 |
| LLISAASNRA | 0337 |
| LLIYDASNRA | 0338 |
| LLIYEASNRA | 0339 |
| LLIYTASNRA | 0340 |
| LLIYADSNRA | 0341 |
| LLIYAGSNRA | 0342 |
| LLIYAADNRA | 0343 |
| LLIYAAGNRA | 0344 |
| LLIYAASDRA | 0345 |
| LLIYAASERA | 0346 |
| LLIYAASNRD | 0347 |
| LLIYAASNRE | 0348 |
| LLIYAASNRG | 0349 |
| LLIYAASNRP | 0350 |

TABLE 11

| V-domain sequences of unique, designer, deimmunized, CSF1R-antagonistic IgGs. | |
|---|---|
| MH-5.1 VH | QVQLVQSGAEVKKPGSSVKVSCKAS**GYTFSS*N*YMIWVRQAPGQGLEWMGDINPYNGGANYAQKFQGRVTITADESTSTAYMELSSLRSEDTAVYYCAREGPYFSNLYVMDY**WGQGTLVTVSS |
| MH-5.2 VH | QVQLVQSGAEVKKPGSSVKVSCKAS**GYTFSS*A*YMIWVRQAPGQGLEWMGDINPYNGGANYAQKFQGRVTITADESTSTAYMELSSLRSEDTAVYYCAREGPYFSNLYVMDY**WGQGTLVTVSS |
| MH-5.3 VH | QVQLVQSGAEVKKPGSSVKVSCKAS**GYTFSS*S*YMIWVRQAPGQGLEWMGDINPYNGGANYAQKFQGRVTITADESTSTAYMELSSLRSEDTAVYYCAREGPYFSNLYVMDY**WGQGTLVTVSS |
| MH-5.4 VH | QVQLVQSGAEVKKPGSSVKVSCKAS**GYTFSS*H*YMIWVRQAPGQGLEWMGDINPYNGGANYAQKFQGRVTITADESTSTAYMELSSLRSEDTAVYYCAREGPYFSNLYVMDY**WGQGTLVTVSS |
| MH-5.5 VH | QVQLVQSGAEVKKPGSSVKVSCKAS**GYTFSS*N*YMIWVRQAPGQGLEWMGDINPYNGGANYAQKFQGRVTITADESTSTAYMELSSLRSEDTAVYYCAREGPYFSNLYVMDY**WG*R*GTLVTVSS |
| MH-5.6 VH | QVQLVQSGAEVKKPGSSVKVSCKAS**GYTFSS*A*YMIWVRQAPGQGLEWMGDINPYNGGANYAQKFQGRVTITADESTSTAYMELSSLRSEDTAVYYCAREGPYFSNLYVMDY**WG*R*GTLVTVSS |
| MH-5.7 VH | QVQLVQSGAEVKKPGSSVKVSCKAS**GYTFSS*S*YMIWVRQAPGQGLEWMGDINPYNGGANYAQKFQGRVTITADESTSTAYMELSSLRSEDTAVYYCAREGPYFSNLYVMDY**WG*R*GTLVTVSS |
| MH-5.8 VH | QVQLVQSGAEVKKPGSSVKVSCKAS**GYTFSS*H*YMIWVRQAPGQGLEWMGDINPYNGGANYAQKFQGRVTITADESTSTAYMELSSLRSEDTAVYYCAREGPYFSNLYVMDY**WG*R*GTLVTVSS |
| MH-5.1 VL | EIVLTQSPATLSLSPGERATLSCRASQSVSYEGENYLNWYQQKPGQAPR*SA*IYAASNRATGIPARFSGSGSGTDFTLTISSPEPEDFAVYYCQLSNEDLLTFGGGTKVEIK |
| MH-5.2 VL | EIVLTQSPATLSLSPGERATLSCRASQSVSYEGENYLNWYQQKPGQAPR*AA*IYAASNRATGIPARFSGSGSGTDFTLTISSPEPEDFAVYYCQLSNEDLLTFGGGTKVEIK |
| MH-5.3 VL | EIVLTQSPATLSLSPGERATLSCRASQSVSYEGENYLNWYQQKPGQAPR*S*LIY**AAS*D*RATGIPARFSGSGSGTDFTLTISSPEPEDFAVYYCQLSNEDLLT**FGGGTKVEIK |
| MH-Min VL | EIVLTQSPATLSLSPGERATLSCRASQSVSYEGENYLNWYQQKPGQAPRLLIYAASNRATGIPARFSGSGSGTDFTLTISSPEPEDFAVYYCQLSNEDLLTFGGGTKVEIK |

CDRs are in bold font. Deimmunizing mutations are in italic and underlined font. SEQ ID NOs are assigned to the V-domain sequences as shown below:
MH-5.1 VH (SEQ ID NO: 1)
MH-5.2 VH (SEQ ID NO: 2)
MH-5.3 VH (SEQ ID NO: 3)
MH-5.4 VH (SEQ ID NO: 4)
MH-5.5 VH (SEQ ID NO: 5)
MH-5.6 VH (SEQ ID NO: 6)
MH-5.7 VH (SEQ ID NO: 7)
MH-5.8 VH (SEQ ID NO: 8)
MH-5.1 VL (SEQ ID NO: 9)
MH-5.2 VL (SEQ ID NO: 10)
MH-5.3 VL (SEQ ID NO: 11)
MH-Min VL (SEQ ID NO: 12)

TABLE 12

V-domain sequence combinations of unique, designer, deimmunized, CSF1R-antagonistic IgGs.

| Clone name | VH sequence | VL sequence |
|---|---|---|
| MH10 | MH 5.1 VH | MH 5.1 VL |
| MH11 |  | MH 5.2 VL |
| MH12 |  | MH 5.3 VL |

TABLE 16-continued

Examples of antibody variable region amino acid sequences.

Antibody MH12 light chain variable (VL) region
QVQLVQSGAEVKKPGSSVKVSCKASGYTFSSNYMIWVRQAPGQGLEWMGDINPYNGGA
NYAQKFQGRVTITADESTSTAYMELSSLRSEDTAVYYCAREGPYFSNLYVMDYWGQGT
LVTVSS (SEQ ID NO: 353)

Antibody MH12 heavy chain variable (VH) region
EIVLTQSPATLSLSPGERATLSCRASQSVSYEGENYLNWYQQKPGQAPRSLIYAASDR
ATGIPARFSGSGSGTDFTLTISSPEPEDFAVYYCQLSNEDLLTFGGGTKVEIK (SEQ
ID NO: 354)

Antibody MH16 light chain variable (VL) region
QVQLVQSGAEVKKPGSSVKVSCKASGYTFSSAYMIWVRQAPGQGLEWMGDINPYNGGA
NYAQKFQGRVTITADESTSTAYMELSSLRSEDTAVYYCAREGPYFSNLYVMDYWGQGT
LVTVSS (SEQ ID NO: 355)

Antibody MH16 heavy chain variable (VH) region
EIVLTQSPATLSLSPGERATLSCRASQSVSYEGENYLNWYQQKPGQAPRSLIYAASDR
ATGIPARFSGSGSGTDFTLTISSPEPEDFAVYYCQLSNEDLLTFGGGTKVEIK (SEQ
ID NO: 356)

Antibody 30E06 light chain variable (VL) region
EIVLTQSPATLSLSPGERATLSCRASQSVSYEGENYLAWYQQKPGQAPRLLIYAASNL
ATGIPARFSGSGSGTDFTLTISSLEPEDFAVYYCQLSNEDLLTFGGGTKVEIK (SEQ
ID NO: 357)

Antibody 30E06 heavy chain variable (VH) region
QVQLVQSGAEVKKPGSSVKVSCKASGYTFTSYYMIWVRQAPGQGLEWMGDINPYNGGT
TYAQKFQGRVTITADESTSTAYMELSSLRSEDTAVYYCAREGPYFSNLYVMDYWGQGT
LVTVSS (SEQ ID NO: 358)

TABLE 17

Examples of antibody Fc region amino acid sequences.

Human IgG4 wild type
ASTKGPSVFPLAPCSRSTSESTAALGCLVKDYFPEPVTVSWNSGALTSGVHTFPAVLQSSGLYSLSSVVT
VPSSSLGTKTYTCNVDHKPSNTKVDKRVESKYGPPCPSCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKS LSLSLGK (SEQ ID NO: 359)

Human IgG4 (S228P)
ASTKGPSVFPLAPCSRSTSESTAALGCLVKDYFPEPVTVSWNSGALTSGVHTFPAVLQSSGLYSLSSVVT
VPSSSLGTKTYTCNVDHKPSNTKVDKRVESKYGPPCPPCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKS LSLSLGK (SEQ ID NO: 360)

Human IgG1 wild type
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO: 361)

Human IgG1-3M
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPEAAGAPSVFLFPPKPKDTLMISRTPE
VTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO: 362)

Human IgG1 wild type "REEM" allotype
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO: 363)

TABLE 17-continued

Examples of antibody Fc region amino acid sequences.

Human IgG1-3M "REEM" allotype
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPEAAGAPSVFLFPPKPKDTLMISRTPE
VTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPS<u>REEM</u>KNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 364)

TABLE 18

Examples of CSFR1 amino acid sequences.

Human CSF1R sequence
MGPGVLLLLLVATAWHGQGIPVIEPSVPELVVKPGATVTLRCVGNGSVEWDGPPSPHWTL
YSDGSSSILSTNNATFQNTGTYRCTEPGDPLGGSAAIHLYVKDPARPWNVLAQEVVVFED
QDALLPCLLTDPVLEAGVSLVRVRGRPLMRHTNYSFSPWHGFTIHRAKFIQSQDYQCSAL
MGGRKVMSISIRLKVQKVIPGPPALTLVPAELVRIRGEAAQIVCSASSVDVNFDVFLQHN
NTKLAIPQQSDFHNNRYQKVLTLNLDQVDFQHAGNYSCVASNVQGKHSTSMFFRVVESAY
LNLSSEQNLIQEVTVGEGLNLKVMVEAYPGLQGFNWTYLGPFSDHQPEPKLANATTKDTY
RHTFTLSLPRLKPSEAGRYSFLARNPGGWRALTFELTLRYPPEVSVIWTFINGSGTLLCA
ASGYPQPNVTWLQCSGHTDRCDEAQVLQVWDDPYPEVLSQEPFHKVTVQSLLTVETLEHN
QTYECRAHNSVGSGSWAFIPISAGAHTHPPDEFLFTPVVVACMSIMALLLLLLLLLLYKY
KQKPKYQVRWKIIESYEGNSYTFIDPTQLPYNEKWEFPRNNLQFGKTLGAGAFGKVVEAT
AFGLGKEDAVLKVAVKMLKSTAHADEKEALMSELKIMSHLGQHENIVNLLGACTHGGPVL
VITEYCCYGDLLNFLRRKAEAMLGPSLSPGQDPEGGVDYKNIHLEKKYVRRDSGFSSQGV
DTYVEMRPVSTSSNDSFSEQDLDKEDGRPLELRDLLHFSSQVAQGMAFLASKNCIHRDVA
ARNVLLTNGHVAKIGDFGLARDIMNDSNYIVKGNARLPVKWMAPESIFDCVYTVQSDVWS
YGILLWEIFSLGLNPYPGILVNSKFYKLVKDGYQMAQPAFAPKNIYSIMQACWALEPTHR
PTFQQICSFLQEQAQEDRRERDYTNLPSSSRSGGSGSSSSELEEESSSEHLTCCEQGDIA
QPLLQPNNYQFC (SEQ ID NO: 365)

Cynomolgus monkey CSF1R sequence
MGPGVLLLLLVVTAWHGQGIPVIEPSPELVVKPGETVTLRCVGNGSVEWDGPISPHWTL
YSDGPSSVLTTNNATFQNTRTYRCTEPGDPLGGSAAIHLYVKDPARPWNVLAKEVVVFED
QDALLPCLLTDPVLEAGVSLVRLRGRPLLRHTNYSFSPWHGFIIHRAKFIQGQDYQCSAL
MGGRKVMSISIRLKVQKVIPGPPALTLVPAELVRIRGEAAQIVCSASNIDVDFDVFLQHN
TTKLAIPQRSDFHDNRYQKVLTLSLGQVDFQHAGNYSCVASNVQGKHSTSMFFRVVESAY
LDLSSEQNLIQEVTVGEGLNLKVMVEAYPGLQGFNWTYLGPFSDHQPEPKLANATTKDTY
RHTFTLSLPRLKPSEAGRYSFLARNPGGWRALTFELTLRYPPEVSVIWTSINGSGTLLCA
ASGYPQPNVTWLQCAGHTDRCDEAQVLQVWVDPHPEVLSQEPFQKVTVQSLLTAETLEHN
QTYECRAHNSVGSGSWAFIPISAGARTHPPDEFLFTPVVVACMSVMALLLLLLLLLLYKY
KQKPKYQVRWKIIESYEGNSYTFIDPTQLPYNEKWEFPRNNLQFGKTLGAGAFGKVVEAT
AFGLGKEDAVLKVAVKMLKSTAHADEKEALMSELKIMSHLGQHENIVNLLGACTHGGPVL
VITEYCCYGDLLNFLRRKAEAMLGPSLSPGQDPEGGADYKNIHLEKKYVRRDSGFSSQGV
DTYVEMRPVSTSSNDSFSEQDLDKEDGRPLELWDLLHFSSQVAQGMAFLASKNCIHRDVA
ARNVLLTNGHVAKIGDFGLARDIMNDSNYIVKGNARLPVKWMAPESIFDCVYTVQSDVWS
YGILLWEIFSLGLNPYPGILVNSKFYKLVKDGYQMAQPAFAPKNIYSIMQACWALEPTHR
PTFQQICSLLQEQAQEDRRERDYTNLPSSSRSGGSGSGSSSSSEPEEESSSEHLACCEQ
GDIAQPLLQPNNYQFC (SEQ ID NO: 366)

The invention claimed is:

1. An anti-CSF1R antibody or an antigen-binding portion thereof, wherein the antibody or antigen-binding portion comprises a heavy chain variable (VH) region and a light chain variable (VL) region, wherein (a) the VH region amino acid sequence comprises HCDR1 of GYTFSSYYMI (SEQ ID NO: 31), HCDR2 of MGDINPYNGGANYAQKFQG (SEQ ID NO: 32) and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38) and LCDR3 of QLSNEDLLT (SEQ ID NO: 39);

(b) the VH region amino acid sequence comprises HCDR1 of GYTFSSNYMI (SEQ ID NO:50), HCDR2 of MGDINPYNGGANYAQKFQG (SEQ ID NO: 32), HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60) and LCDR3 of QLSNEDLLT (SEQ ID NO: 39);

(c) the VH region amino acid sequence comprises HCDR1 of GYTFSSAYMI (SEQ ID NO:57), HCDR2 of MGDINPYNGGANYAQKFQG (SEQ ID NO:32) and HCDR3 of EGPYFSNLYVMDY (HCDR3; SEQ ID NO: 33); and the VL region amino acid sequence comprises LCDR1 of RASQSVSYEGENYLN (SEQ ID NO:37), LCDR2 of AASDRAT (SEQ ID NO:60) and LCDR3 of QLSNEDLLT (SEQ ID NO:39);

(d) the VH region amino acid sequence comprises HCDR1 of GYTFTSYYMI (SEQ ID NO:41), HCDR2 of MGDINPYNGGTTYAQKFQG (SEQ ID NO:42) and HCDR3 of EGPYFSNLYVMDY (SEQ ID NO:33); and the VL region amino acid sequence comprises LCDR1 of RASQSVSYEGENYLA (SEQ ID NO:40), LCDR2 of AASNLAT (SEQ ID NO:43) and LCDR3 of QLSNEDLLT (SEQ ID NO:39);

(e) the VH region amino acid sequence comprises HCDR1 of GYTFSSYYMI (SEQ ID NO: 31), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYQGENYLA (SEQ ID NO: 34), LCDR2 of DASNRAT (SEQ ID NO: 35), and LCDR3 of QLSNQDLLT (SEQ ID NO: 36);

(f) the VH region amino acid sequence comprises HCDR1 of GYTFSSYYMI (SEQ ID NO: 31), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(g) the VH region amino acid sequence comprises HCDR1 of GYTFSSYYMI (SEQ ID NO: 31), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLA (SEQ ID NO:40), LCDR2 of AASNRAT (SEQ ID NO:38), and LCDR3 of QLSNQDLLT (SEQ ID NO: 36);

(h) the VH region amino acid sequence comprises HCDR1 of GYTFTSYYMI (SEQ ID NO:41), HCDR2 of MGDINPYNGGTTYAQKFQG (SEQ ID NO: 42), and HCDR3 of EGPYFSNLYVMDY (SEQ ID NO: 33); and the VL region amino acid sequence comprises LCDR1 of RASQSVSYEGENYLA (SEQ ID NO:40), LCDR2 of AASNLAT (SEQ ID NO:43), and LCDR3 of QLSNEDLLT (SEQ ID NO: 39);

(i) the VH region amino acid sequence comprises HCDR1 of GYTFTSYYMI (SEQ ID NO:41), HCDR2 of MGDINPYNGGANFAQKFQG (SEQ ID NO:44), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(j) the VH region amino acid sequence comprises HCDR1 of GYTFTSYYMI (SEQ ID NO:41), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(k) the VH region amino acid sequence comprises HCDR1 of GYTFSSYYMI (SEQ ID NO: 31), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVEYQGDNYLN (SEQ ID NO:45), LCDR2 of AASNRAT (SEQ ID NO:38), and LCDR3 of QLSNEDLLT (SEQ ID NO: 39);

(l) the VH region amino acid sequence comprises HCDR1 of GYTFTSYYII (SEQ ID NO:46), HCDR2 of MGDINPYNGGATYAQKFQG (SEQ ID NO:47), and HCDR3 of EPPYFSNLYVMDY (SEQ ID NO:48); and the VL region amino acid sequence comprises LCDR1 of RASQSVEYEGDNYLN (SEQ ID NO:49), LCDR2 of AASNRAT (SEQ ID NO:38), and LCDR3 of QLSNQDLLT (SEQ ID NO: 36);

(m) the VH region amino acid sequence comprises HCDR1 of GYTFSSNYMI (SEQ ID NO:50), HCDR2 of MGDINPYNGGATYNQKFQG (SEQ ID NO:51), and HCDR3 of EPPYFSNLYVMDY (SEQ ID NO:48); and the VL region amino acid sequence comprises LCDR1 of RASQSVEYEGENYLN (SEQ ID NO:52), LCDR2 of AASNRAT (SEQ ID NO:38), and LCDR3 of QLSNQDLLT (SEQ ID NO: 36);

(n) the VH region amino acid sequence comprises HCDR1 of GYTFSSYYMI (SEQ ID NO: 31), HCDR2 of MGDINPYNGGTTYAQKFQG (SEQ ID NO: 42), and HCDR3 of EGPYFSNLYVMDY (SEQ ID NO: 33); and the VL region amino acid sequence comprises LCDR1 of RASQSVEYQGENYLN (SEQ ID NO:53), LCDR2 of AASNRAT (SEQ ID NO:38), and LCDR3 of QLSNQDLLT (SEQ ID NO: 36);

(o) the VH region amino acid sequence comprises HCDR1 of GYTFTSNYII (SEQ ID NO:54), HCDR2 of MGDINPYNGGTNYAQKFQG (SEQ ID NO:55), and HCDR3 of EGPYFSNLYVMDY (SEQ ID NO: 33); and the VL region amino acid sequence comprises LCDR1 of RASQSVEYQGENYLN (SEQ ID NO:53), LCDR2 of AASNRAT (SEQ ID NO:38), and LCDR3 of QLSSEDLLT (SEQ ID NO:56);

(p) the VH region amino acid sequence comprises HCDR1 of GYTFSSNYMI (SEQ ID NO:50), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(q) the VH region amino acid sequence comprises HCDR1 of GYTFSSAYMI (SEQ ID NO:57), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(r) the VH region amino acid sequence comprises HCDR1 of GYTFSSSYMI (SEQ ID NO:58), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(s) the VH region amino acid sequence comprises HCDR1 of GYTFSSHYMI (SEQ ID NO:59), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASNRAT (SEQ ID NO:38), and LCDR3 of QLSNEDLLT (SEQ ID NO: 39);

(t) the VH region amino acid sequence comprises HCDR1 of GYTFSSNYMI (SEQ ID NO:50), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39);

(u) the VH region amino acid sequence comprises HCDR1 of GYTFSSAYMI (SEQ ID NO:57), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39);

(v) the VH region amino acid sequence comprises HCDR1 of GYTFSSSYMI (SEQ ID NO:58), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39); or (w) the VH region amino acid sequence comprises HCDR1 of GYTFSSHYMI (SEQ ID NO:59), HCDR2 of MGDINPYNGGANYAQKFQG (SEQ ID NO:32), and HCDR3 of EGPYFSNLYVMDY (SEQ ID NO: 33); and the VL region amino acid sequence comprises LCDR1 of RASQSVSYEGENYLN (SEQ ID NO: 37), LCDR2 of AASDRAT (SEQ ID NO:60), and LCDR3 of QLSNEDLLT (SEQ ID NO: 39).

2. The antibody or antigen-binding portion of claim 1, wherein
   (a) the VH region amino acid sequence comprises SEQ ID NO:352 and the VL region amino acid sequence comprises SEQ ID NO:351;
   (b) the VH region amino acid sequence comprises SEQ ID NO:354 and the VL region amino acid sequence comprises SEQ ID NO:353;
   (c) the VH region amino acid sequence comprises SEQ ID NO:356 and the VL region amino acid sequence comprises SEQ ID NO:355; or
   (d) the VH region amino acid sequence comprises SEQ ID NO:358 and the VL region amino acid sequence comprises SEQ ID NO:357.

3. The antibody or antigen-binding portion of claim 1, wherein the antibody is humanized or chimeric.

4. The antibody or antigen-binding portion of claim 1, wherein the VH region, the VL region, or both the VH and the VL region comprise one or more human framework region amino acid sequences.

5. The antibody or antigen-binding portion of claim 1, wherein the VH region, the VL region, or both the VH and the VL region comprise a human variable region framework scaffold amino acid sequence into which the CDRs have been inserted.

6. The antibody or antigen-binding portion of claim 1, wherein the VH region comprises an IGHV1-69*01 human germline scaffold amino acid sequence into which the HCDR1, HCDR2 and HCDR3 amino acid sequences have been inserted.

7. The antibody or antigen-binding portion of claim 1, wherein the VL region comprises an IGKV3-11 human germline scaffold amino acid sequence into which the LCDR1, LCDR2 and LCDR3 amino acid sequences have been inserted.

8. The antibody or antigen-binding portion of claim 1, wherein the antibody or antigen-binding portion comprises an immunoglobulin constant region.

9. The antibody or antigen-binding portion of claim 8, wherein the immunoglobulin constant region is IgG, IgE, IgM, IgD, IgA or IgY.

10. The antibody or antigen-binding portion of claim 9, wherein the immunoglobulin constant region is IgG1, IgG2, IgG3, IgG4, IgA1 or IgA2.

11. The antibody or antigen-binding portion of claim 8, wherein the immunoglobulin constant region is immunologically inert.

12. The antibody or antigen-binding portion of claim 8, wherein the immunoglobulin constant region is a wild-type human IgG4 constant region, a human IgG4 constant region comprising the amino acid substitution S228P, a wild-type human IgG1 constant region or a human IgG1 constant region comprising the amino acid substitutions L234A, L235A and G237A.

13. The antibody or antigen-binding portion of claim 8, wherein the immunoglobulin constant region comprises any one of SEQ ID NOS:359-364.

14. The antibody or antigen-binding portion of claim 1, wherein the antibody or antigen-binding portion is an Fab, an Fab', an F(ab')$_2$, an Fv, an scFv, a maxibody, a minibody, a diabody, a triabody, a tetrabody, or a bis-scFv.

15. The antibody or antigen-binding portion of claim 1, wherein the antibody is monoclonal.

16. The antibody or antigen-binding portion of claim 1, wherein the antibody or antigen-binding portion is tetrameric, tetravalent or multispecific.

17. The antibody or antigen-binding portion of claim 1, wherein the antibody is a bispecific antibody that binds specifically to a first antigen and a second antigen, wherein the first antigen is CSF1R and the second antigen is not CSF1R, and wherein the second antigen does not comprise SEQ ID NO: 365 or SEQ ID NO: 366.

18. The antibody or antigen-binding portion of claim 1, wherein the antibody or antigen-binding portion binds specifically to (a) human CSF1R, (b) human CSF1R and cynomolgus CSF1R, or (c) human CSF1R, cynomolgus CSF1R, and rhesus CSF1R.

19. A pharmaceutical composition comprising the antibody or antigen-binding portion of claim 1, and a pharmaceutically acceptable carrier, diluent or excipient.

20. An immunoconjugate comprising the antibody or antigen-binding portion of claim 1 linked to a therapeutic agent.

21. The immunoconjugate of claim 20, wherein the therapeutic agent is a cytotoxin, a radioisotope, a chemotherapeutic agent, an immunomodulatory agent, a cytostatic enzyme, a cytolytic enzyme, a therapeutic nucleic acid, an anti-angiogenic agent, an anti-proliferative agent, or a pro-apoptotic agent.

* * * * *

SEQUENCE LISTING

<160> NUMBER OF SEQ ID NOS: 366

<210> SEQ ID NO 1
<211> LENGTH: 122
<212> TYPE: PRT
<213> ORGANISM: Artificial Sequence
<220> FEATURE:
<223> OTHER INFORMATION: CSF1R-antagonistic IgG VH

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Tyr Met Ile Trp Val Arg Gln Ala Pro Gly Gln Gly Leu Glu Trp Met

```
                35                  40                  45
Gly Asp Ile Asn Pro Tyr Asn Gly Gly Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Pro Tyr Phe Ser Asn Leu Tyr Val Met Asp Tyr Trp
                100                 105                 110
Gly Gln Gly Thr Leu Val Thr Val Ser Ser
        115                 120

<210> SEQ ID NO 2
<211> LENGTH: 122
<212> TYPE: PRT
<213> ORGANISM: Artificial Sequence
<220> FEATURE:
<223> OTHER INFORMATION: CSF1R-antagonistic IgG VH

<400> SEQUENCE: 2

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Ser Ser Ala
                20                  25                  30
Tyr Met Ile Trp Val Arg Gln Ala Pro Gly Gln Gly Leu Glu Trp Met
                35                  40                  45
Gly Asp Ile Asn Pro Tyr Asn Gly Gly Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Pro Tyr Phe Ser Asn Leu Tyr Val Met Asp Tyr Trp
                100                 105                 110
Gly Gln Gly Thr Leu Val Thr Val Ser Ser
        115                 120

<210> SEQ ID NO 3
<211> LENGTH: 122
<212> TYPE: PRT
<213> ORGANISM: Artificial Sequence
<220> FEATURE:
<223> OTHER INFORMATION: CSF1R-antagonistic IgG VH

<400> SEQUENCE: 3

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Ser Ser Ser
                20                  25                  30
Tyr Met Ile Trp Val Arg Gln Ala Pro Gly Gln Gly Leu Glu Trp Met
                35                  40                  45
Gly Asp Ile Asn Pro Tyr Asn Gly Gly Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
```

Ala Arg Glu Gly Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 4
<211> LENGTH: 122
<212> TYPE: PRT
<213> ORGANISM: Artificial Sequence
<220> FEATURE:
<223> OTHER INFORMATION: CSF1R-antagonistic IgG VH

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser His
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 5
<211> LENGTH: 122
<212> TYPE: PRT
<213> ORGANISM: Artificial Sequence
<220> FEATURE:
<223> OTHER INFORMATION: CSF1R-antagonistic IgG VH

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Phe Ser Asn Leu Tyr Val Met Asp Tyr Trp
            100                 105                 110

Gly Arg Gly Thr Leu Val Thr Val Ser Ser
        115                 120

<210> SEQ ID NO 6
<211> LENGTH: 122
<212> TYPE: PRT
<213> ORGANISM: Artificial Sequence

```
<220> FEATURE:
<223> OTHER INFORMATION: CSF1R-antagonistic IgG VH

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Ala
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Phe Ser Asn Leu Tyr Val Met Asp Tyr Trp
            100                 105                 110

Gly Arg Gly Thr Leu Val Thr Val Ser Ser
        115                 120

<210> SEQ ID NO 7
<211> LENGTH: 122
<212> TYPE: PRT
<213> ORGANISM: Artificial Sequence
<220> FEATURE:
<223> OTHER INFORMATION: CSF1R-antagonistic IgG VH

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Ser
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Phe Ser Asn Leu Tyr Val Met Asp Tyr Trp
            100                 105                 110

Gly Arg Gly Thr Leu Val Thr Val Ser Ser
        115                 120

<210> SEQ ID NO 8
<211> LENGTH: 122
<212> TYPE: PRT
<213> ORGANISM: Artificial Sequence
<220> FEATURE:
<223> OTHER INFORMATION: CSF1R-antagonistic IgG VH

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser His
            20                  25                  30
```

```
Tyr Met Ile Trp Val Arg Gln Ala Pro Gly Gln Gly Leu Glu Trp Met
            35                  40                  45

Gly Asp Ile Asn Pro Tyr Asn Gly Gly Ala Asn Tyr Ala Gln Lys Phe
 50                      55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Pro Tyr Phe Ser Asn Leu Tyr Val Met Asp Tyr Trp
            100                 105                 110

Gly Arg Gly Thr Leu Val Thr Val Ser Ser
            115                 120

<210> SEQ ID NO 9
<211> LENGTH: 111
<212> TYPE: PRT
<213> ORGANISM: Artificial Sequence
<220> FEATURE:
<223> OTHER INFORMATION: CSF1R-antagonistic IgG VL

<400> SEQUENCE: 9

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Tyr Glu
                 20                  25                  30

Gly Glu Asn Tyr Leu Asn Trp Tyr Gln Gln Lys Pro Gly Gln Ala Pro
             35                  40                  45

Arg Ser Ala Ile Tyr Ala Ala Ser Asn Arg Ala Thr Gly Ile Pro Ala
 50                  55                  60

Arg Phe Ser Gly Ser Gly Ser Gly Thr Asp Phe Thr Leu Thr Ile Ser
 65                  70                  75                  80

Ser Pro Glu Pro Glu Asp Phe Ala Val Tyr Tyr Cys Gln Leu Ser Asn
                 85                  90                  95

Glu Asp Leu Leu Thr Phe Gly Gly Gly Thr Lys Val Glu Ile Lys
            100                 105                 110

<210> SEQ ID NO 10
<211> LENGTH: 111
<212> TYPE: PRT
<213> ORGANISM: Artificial Sequence
<220> FEATURE:
<223> OTHER INFORMATION: CSF1R-antagonistic IgG VL

<400> SEQUENCE: 10

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Tyr Glu
                 20                  25                  30

Gly Glu Asn Tyr Leu Asn Trp Tyr Gln Gln Lys Pro Gly Gln Ala Pro
             35                  40                  45

Arg Ala Ala Ile Tyr Ala Ala Ser Asn Arg Ala Thr Gly Ile Pro Ala
 50                  55                  60

Arg Phe Ser Gly Ser Gly Ser Gly Thr Asp Phe Thr Leu Thr Ile Ser
 65                  70                  75                  80

Ser Pro Glu Pro Glu Asp Phe Ala Val Tyr Tyr Cys Gln Leu Ser Asn
                 85                  90                  95

Glu Asp Leu Leu Thr Phe Gly Gly Gly Thr Lys Val Glu Ile Lys
            100                 105                 110
```

```
<210> SEQ ID NO 11
<211> LENGTH: 111
<212> TYPE: PRT
<213> ORGANISM: Artificial Sequence
<220> FEATURE:
<223> OTHER INFORMATION: CSF1R-antagonistic IgG VL

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Glu
            20                  25                  30

Gly Glu Asn Tyr Leu Asn Trp Tyr Gln Gln Lys Pro Gly Gln Ala Pro
        35                  40                  45

Arg Ser Leu Ile Tyr Ala Ala Ser Asp Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Pro Glu Pro Glu Asp Phe Ala Val Tyr Tyr Cys Gln Leu Ser Asn
                85                  90                  95

Glu Asp Leu Leu Thr Phe Gly Gly Gly Thr Lys Val Glu Ile Lys
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: CSF1R-antagonistic IgG VL

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Glu
            20                  25                  30

Gly Glu Asn Tyr Leu Asn Trp Tyr Gln Gln Lys Pro Gly Gln Ala Pro
        35                  40                  45

Arg Leu Leu Ile Tyr Ala Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Pro Glu Pro Glu Asp Phe Ala Val Tyr Tyr Cys Gln Leu Ser Asn
                85                  90                  95

Glu Asp Leu Leu Thr Phe Gly Gly Gly Thr Lys Val Glu Ile Lys
            100                 105                 110

<210> SEQ ID NO 13
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1
<220> FEATURE:
<221> NAME/KEY: MISC_FEATURE
<222> LOCATION: (2)..(2)
<223> OTHER INFORMATION: Xaa is Tyr or Gly
<220> FEATURE:
<221> NAME/KEY: MISC_FEATURE
<222> LOCATION: (5)..(5)
<223> OTHER INFORMATION: Xaa is Thr or Ser
```

```
<220> FEATURE:
<221> NAME/KEY: MISC_FEATURE
<222> LOCATION: (6)..(6)
<223> OTHER INFORMATION: Xaa is Asp or Ser
<220> FEATURE:
<221> NAME/KEY: MISC_FEATURE
<222> LOCATION: (7)..(7)
<223> OTHER INFORMATION: Xaa is Asn, Ala, Ser, His or Tyr
<220> FEATURE:
<221> NAME/KEY: MISC_FEATURE
<222> LOCATION: (8)..(8)
<223> OTHER INFORMATION: Xaa is Tyr or Ala
<220> FEATURE:
<221> NAME/KEY: MISC_FEATURE
<222> LOCATION: (9)..(9)
<223> OTHER INFORMATION: Xaa is Met or Ile
<220> FEATURE:
<221> NAME/KEY: MISC_FEATURE
<222> LOCATION: (10)..(10)
<223> OTHER INFORMATION: Xaa is  Ile or Ser

<400> SEQUENCE: 13

Gly Xaa Thr Phe Xaa Xaa Xaa Xaa Xaa Xaa
1               5                   10

<210> SEQ ID NO 14
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2
<220> FEATURE:
<221> NAME/KEY: MISC_FEATURE
<222> LOCATION: (3)..(3)
<223> OTHER INFORMATION: Xaa is Asp or Gly
<220> FEATURE:
<221> NAME/KEY: MISC_FEATURE
<222> LOCATION: (5)..(5)
<223> OTHER INFORMATION: Xaa is Asn or Ile
<220> FEATURE:
<221> NAME/KEY: MISC_FEATURE
<222> LOCATION: (7)..(7)
<223> OTHER INFORMATION: Xaa is Tyr or Ile
<220> FEATURE:
<221> NAME/KEY: MISC_FEATURE
<222> LOCATION: (8)..(8)
<223> OTHER INFORMATION: Xaa is Asn or Phe
<220> FEATURE:
<221> NAME/KEY: MISC_FEATURE
<222> LOCATION: (10)..(10)
<223> OTHER INFORMATION: Xaa is Gly or Thr
<220> FEATURE:
<221> NAME/KEY: MISC_FEATURE
<222> LOCATION: (11)..(11)
<223> OTHER INFORMATION: Xaa is Thr or Ala
<220> FEATURE:
<221> NAME/KEY: MISC_FEATURE
<222> LOCATION: (12)..(12)
<223> OTHER INFORMATION: Xaa is Thr or Asn
<220> FEATURE:
<221> NAME/KEY: MISC_FEATURE
<222> LOCATION: (13)..(13)
<223> OTHER INFORMATION: Xaa is Phe or Tyr
<220> FEATURE:
<221> NAME/KEY: MISC_FEATURE
<222> LOCATION: (14)..(14)
<223> OTHER INFORMATION: Xaa is Asn or Ala
<220> FEATURE:
<221> NAME/KEY: MISC_FEATURE
<222> LOCATION: (18)..(18)
<223> OTHER INFORMATION: Xaa is Gln or Lys

<400> SEQUENCE: 14

Met Gly Xaa Ile Xaa Pro Xaa Xaa Gly Xaa Xaa Xaa Xaa Xaa Gln Lys
1               5                   10                  15
```

Phe Xaa Gly

```
<210> SEQ ID NO 15
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3
<220> FEATURE:
<221> NAME/KEY: MISC_FEATURE
<222> LOCATION: (1)..(1)
<223> OTHER INFORMATION: Xaa is Glu or a conservative substitution of
      Glu, such as Asp
<220> FEATURE:
<221> NAME/KEY: MISC_FEATURE
<222> LOCATION: (2)..(2)
<223> OTHER INFORMATION: Xaa is Asp, Gly, His, Ser, Thr, Pro, Val, Asn,
      Ile or Tyr
<220> FEATURE:
<221> NAME/KEY: MISC_FEATURE
<222> LOCATION: (3)..(3)
<223> OTHER INFORMATION: Xaa is Pro, Thr, Asn, Glu, Leu, Ala, Asp or Ser
<220> FEATURE:
<221> NAME/KEY: MISC_FEATURE
<222> LOCATION: (4)..(4)
<223> OTHER INFORMATION: Xaa is Tyr, Lys, Arg, Met or Pro
<220> FEATURE:
<221> NAME/KEY: MISC_FEATURE
<222> LOCATION: (5)..(5)
<223> OTHER INFORMATION: Xaa is Phe, Asp, Ser, Thr, Glu, Trp, Met, Tyr,
      Leu, Gln, Lys, Gly, Ala or Ile
<220> FEATURE:
<221> NAME/KEY: MISC_FEATURE
<222> LOCATION: (6)..(6)
<223> OTHER INFORMATION: Xaa is Ser, Glu, Gly or Arg
<220> FEATURE:
<221> NAME/KEY: MISC_FEATURE
<222> LOCATION: (7)..(7)
<223> OTHER INFORMATION: Xaa is Asn, Glu, Gln, Gly, His or Met
<220> FEATURE:
<221> NAME/KEY: MISC_FEATURE
<222> LOCATION: (8)..(8)
<223> OTHER INFORMATION: Xaa is Leu, His, Ser or Tyr
<220> FEATURE:
<221> NAME/KEY: MISC_FEATURE
<222> LOCATION: (9)..(9)
<223> OTHER INFORMATION: Xaa is Tyr or Trp

<400> SEQUENCE: 15

Xaa Xaa Xaa Xaa Xaa Xaa Xaa Xaa Xaa Val Met Asp Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: 0301 murine/humanized antibody HCDR1

<400> SEQUENCE: 16

Gly Tyr Thr Phe Thr Asp Asn Tyr Met Ile
1               5                   10

<210> SEQ ID NO 17
<211> LENGTH: 17
<212> TYPE: PRT
<213> ORGANISM: Artificial Sequence
<220> FEATURE:
<223> OTHER INFORMATION: 0301 murine/humanized antibody HCDR2

<400> SEQUENCE: 17
```

```
Asp Ile Asn Pro Tyr Asn Gly Gly Thr Thr Phe Asn Gln Lys Phe Lys
1               5                   10                  15

Gly

<210> SEQ ID NO 18
<211> LENGTH: 13
<212> TYPE: PRT
<213> ORGANISM: Artificial Sequence
<220> FEATURE:
<223> OTHER INFORMATION: 0301 murine/humanized antibody HCDR3

<400> SEQUENCE: 18

Glu Ser Pro Tyr Phe Ser Asn Leu Tyr Val Met Asp Tyr
1               5                   10

<210> SEQ ID NO 19
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1
<220> FEATURE:
<221> NAME/KEY: MISC_FEATURE
<222> LOCATION: (7)..(7)
<223> OTHER INFORMATION: Xaa is Ser, Asp or Glu
<220> FEATURE:
<221> NAME/KEY: MISC_FEATURE
<222> LOCATION: (9)..(9)
<223> OTHER INFORMATION: Xaa is Asp, Glu or Gln
<220> FEATURE:
<221> NAME/KEY: MISC_FEATURE
<222> LOCATION: (11)..(11)
<223> OTHER INFORMATION: Xaa is Asp or Glu
<220> FEATURE:
<221> NAME/KEY: MISC_FEATURE
<222> LOCATION: (15)..(15)
<223> OTHER INFORMATION: Xaa is Asn or Ala

<400> SEQUENCE: 19

Arg Ala Ser Gln Ser Val Xaa Tyr Xaa Gly Xaa Asn Tyr Leu Xaa
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2
<220> FEATURE:
<221> NAME/KEY: MISC_FEATURE
<222> LOCATION: (1)..(1)
<223> OTHER INFORMATION: Xaa is Ala or Asp
<220> FEATURE:
<221> NAME/KEY: MISC_FEATURE
<222> LOCATION: (4)..(4)
<223> OTHER INFORMATION: Xaa is Asn or Asp
<220> FEATURE:
<221> NAME/KEY: MISC_FEATURE
<222> LOCATION: (5)..(5)
<223> OTHER INFORMATION: Xaa is Leu or Arg
<220> FEATURE:
<221> NAME/KEY: MISC_FEATURE
<222> LOCATION: (6)..(6)
<223> OTHER INFORMATION: Xaa is Glu or Ala

<400> SEQUENCE: 20

Xaa Ala Ser Xaa Xaa Xaa Thr
1               5
```

```
<210> SEQ ID NO 21
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3
<220> FEATURE:
<221> NAME/KEY: MISC_FEATURE
<222> LOCATION: (1)..(1)
<223> OTHER INFORMATION: Xaa is Gln, His or Asn
<220> FEATURE:
<221> NAME/KEY: MISC_FEATURE
<222> LOCATION: (2)..(2)
<223> OTHER INFORMATION: Xaa is Leu or Gln
<220> FEATURE:
<221> NAME/KEY: MISC_FEATURE
<222> LOCATION: (4)..(4)
<223> OTHER INFORMATION: Xaa is Asn or Ser
<220> FEATURE:
<221> NAME/KEY: MISC_FEATURE
<222> LOCATION: (5)..(5)
<223> OTHER INFORMATION: Xaa is Glu, Gln or Asn
<220> FEATURE:
<221> NAME/KEY: MISC_FEATURE
<222> LOCATION: (6)..(6)
<223> OTHER INFORMATION: Xaa is Asp or Trp
<220> FEATURE:
<221> NAME/KEY: MISC_FEATURE
<222> LOCATION: (8)..(8)
<223> OTHER INFORMATION: Xaa is Leu or Ser

<400> SEQUENCE: 21

Xaa Xaa Ser Xaa Xaa Xaa Leu Xaa Thr
1               5

<210> SEQ ID NO 22
<211> LENGTH: 15
<212> TYPE: PRT
<213> ORGANISM: Artificial Sequence
<220> FEATURE:
<223> OTHER INFORMATION: 0301 murine/humanized antibody LCDR1

<400> SEQUENCE: 22

Lys Ala Ser Gln Ser Val Asp Tyr Asp Gly Asp Asn Tyr Met Asn
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: 0301 murine/humanized antibody LCDR2

<400> SEQUENCE: 23

Ala Ala Ser Asn Leu Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: 0301 murine/humanized antibody LCDR3

<400> SEQUENCE: 24

His Leu Ser Asn Glu Asp Leu Ser Thr
1               5

<210> SEQ ID NO 25
<211> LENGTH: 10
```

```
<212> TYPE: PRT
<213> ORGANISM: Artificial Sequence
<220> FEATURE:
<223> OTHER INFORMATION: anti-CSF1R antibody molecule or antigen-binding
      portion HCDR1
<220> FEATURE:
<221> NAME/KEY: MISC_FEATURE
<222> LOCATION: (2)..(2)
<223> OTHER INFORMATION: Xaa is Tyr or Gly
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (6)..(6)
<223> OTHER INFORMATION: Xaa is Asp or Ser
<220> FEATURE:
<221> NAME/KEY: MISC_FEATURE
<222> LOCATION: (7)..(7)
<223> OTHER INFORMATION: Xaa is Asn, Ala, Ser, His or Tyr
<220> FEATURE:
<221> NAME/KEY: MISC_FEATURE
<222> LOCATION: (8)..(8)
<223> OTHER INFORMATION: Xaa is Tyr or Ala
<220> FEATURE:
<221> NAME/KEY: MISC_FEATURE
<222> LOCATION: (9)..(9)
<223> OTHER INFORMATION: Xaa is Met or Ile
<220> FEATURE:
<221> NAME/KEY: MISC_FEATURE
<222> LOCATION: (10)..(10)
<223> OTHER INFORMATION: Xaa is Ile or Ser

<400> SEQUENCE: 25

Gly Xaa Thr Phe Xaa Xaa Xaa Xaa Xaa Xaa
1               5                   10

<210> SEQ ID NO 26
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2
<220> FEATURE:
<221> NAME/KEY: MISC_FEATURE
<222> LOCATION: (1)..(1)
<223> OTHER INFORMATION: Xaa is Met or a conservative substitution of
      Met
<220> FEATURE:
<221> NAME/KEY: MISC_FEATURE
<222> LOCATION: (3)..(3)
<223> OTHER INFORMATION: Xaa is Asp or Gly
<220> FEATURE:
<221> NAME/KEY: MISC_FEATURE
<222> LOCATION: (5)..(5)
<223> OTHER INFORMATION: Xaa is Asn or Ile
<220> FEATURE:
<221> NAME/KEY: MISC_FEATURE
<222> LOCATION: (7)..(7)
<223> OTHER INFORMATION: Xaa is Tyr or Ile
<220> FEATURE:
<221> NAME/KEY: MISC_FEATURE
<222> LOCATION: (8)..(8)
<223> OTHER INFORMATION: Xaa is Asn or Phe
<220> FEATURE:
<221> NAME/KEY: MISC_FEATURE
<222> LOCATION: (10)..(10)
<223> OTHER INFORMATION: Xaa is Gly or Thr
<220> FEATURE:
<221> NAME/KEY: MISC_FEATURE
<222> LOCATION: (11)..(11)
<223> OTHER INFORMATION: Xaa is Thr or Ala
<220> FEATURE:
<221> NAME/KEY: MISC_FEATURE
<222> LOCATION: (12)..(12)
```

```
<223> OTHER INFORMATION: Xaa is Thr or Asn
<220> FEATURE:
<221> NAME/KEY: MISC_FEATURE
<222> LOCATION: (13)..(13)
<223> OTHER INFORMATION: Xaa is Phe or Tyr
<220> FEATURE:
<221> NAME/KEY: MISC_FEATURE
<222> LOCATION: (14)..(14)
<223> OTHER INFORMATION: Xaa is Asn or Ala
<220> FEATURE:
<221> NAME/KEY: MISC_FEATURE
<222> LOCATION: (18)..(18)
<223> OTHER INFORMATION: Xaa is Gln or Lys

<400> SEQUENCE: 26

Xaa Gly Xaa Ile Xaa Pro Xaa Xaa Gly Xaa Xaa Xaa Xaa Xaa Gln Lys
1               5                   10                  15

Phe Xaa Gly

<210> SEQ ID NO 27
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3
<220> FEATURE:
<221> NAME/KEY: MISC_FEATURE
<222> LOCATION: (1)..(1)
<223> OTHER INFORMATION: Xaa is Glu or a conservative substitution of
      Glu
<220> FEATURE:
<221> NAME/KEY: MISC_FEATURE
<222> LOCATION: (2)..(2)
<223> OTHER INFORMATION: Xaa is Asp, Gly, His, Ser, Thr, Pro, Val, Asn,
      Ile, or Tyr
<220> FEATURE:
<221> NAME/KEY: MISC_FEATURE
<222> LOCATION: (3)..(3)
<223> OTHER INFORMATION: Xaa is Pro, Thr, Asn, Glu, Leu, Ala, Asp, or
      Ser
<220> FEATURE:
<221> NAME/KEY: MISC_FEATURE
<222> LOCATION: (4)..(4)
<223> OTHER INFORMATION: Xaa is Tyr, Lys, Arg, Met, or Pro
<220> FEATURE:
<221> NAME/KEY: MISC_FEATURE
<222> LOCATION: (5)..(5)
<223> OTHER INFORMATION: Xaa is Phe, Asp, Ser, Thr, Glu, Trp, Met, Tyr,
      Leu, Gln, Lys, Gly, Ala, or Ile
<220> FEATURE:
<221> NAME/KEY: MISC_FEATURE
<222> LOCATION: (6)..(6)
<223> OTHER INFORMATION: Xaa is Ser, Glu, Gly, or Arg
<220> FEATURE:
<221> NAME/KEY: MISC_FEATURE
<222> LOCATION: (7)..(7)
<223> OTHER INFORMATION: Xaa is Asn, Glu, Gln, Gly, His, or Met
<220> FEATURE:
<221> NAME/KEY: MISC_FEATURE
<222> LOCATION: (8)..(8)
<223> OTHER INFORMATION: Xaa is Leu, His, Ser, or Tyr
<220> FEATURE:
<221> NAME/KEY: MISC_FEATURE
<222> LOCATION: (9)..(9)
<223> OTHER INFORMATION: Xaa is Tyr or Trp

<400> SEQUENCE: 27

Xaa Xaa Xaa Xaa Xaa Xaa Xaa Xaa Xaa Val Met Asp Tyr
1               5                   10

<210> SEQ ID NO 28
<211> LENGTH: 15
<212> TYPE: PRT
```

```
<213> ORGANISM: Artificial Sequence
<220> FEATURE:
<223> OTHER INFORMATION: anti-CSF1R antibody molecule or antigen-binding
      portion LCDR1
<220> FEATURE:
<221> NAME/KEY: MISC_FEATURE
<222> LOCATION: (7)..(7)
<223> OTHER INFORMATION: Xaa is Ser, Asp, or Glu
<220> FEATURE:
<221> NAME/KEY: MISC_FEATURE
<222> LOCATION: (9)..(9)
<223> OTHER INFORMATION: Xaa is Asp, Glu, or Gln
<220> FEATURE:
<221> NAME/KEY: MISC_FEATURE
<222> LOCATION: (11)..(11)
<223> OTHER INFORMATION: Xaa is Asp or Glu
<220> FEATURE:
<221> NAME/KEY: MISC_FEATURE
<222> LOCATION: (15)..(15)
<223> OTHER INFORMATION: Xaa is Asn or Ala

<400> SEQUENCE: 28

Arg Ala Ser Gln Ser Val Xaa Tyr Xaa Gly Xaa Asn Tyr Leu Xaa
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2
<220> FEATURE:
<221> NAME/KEY: MISC_FEATURE
<222> LOCATION: (1)..(1)
<223> OTHER INFORMATION: Xaa is Ala or Asp
<220> FEATURE:
<221> NAME/KEY: MISC_FEATURE
<222> LOCATION: (4)..(4)
<223> OTHER INFORMATION: Xaa is Asp or Asn
<220> FEATURE:
<221> NAME/KEY: MISC_FEATURE
<222> LOCATION: (5)..(5)
<223> OTHER INFORMATION: Xaa is Leu or Arg
<220> FEATURE:
<221> NAME/KEY: MISC_FEATURE
<222> LOCATION: (6)..(6)
<223> OTHER INFORMATION: Xaa is Glu or Ala

<400> SEQUENCE: 29

Xaa Ala Ser Xaa Xaa Xaa Thr
1               5

<210> SEQ ID NO 30
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3
<220> FEATURE:
<221> NAME/KEY: MISC_FEATURE
<222> LOCATION: (1)..(1)
<223> OTHER INFORMATION: Xaa is Gln, His, or Asn
<220> FEATURE:
<221> NAME/KEY: MISC_FEATURE
<222> LOCATION: (2)..(2)
<223> OTHER INFORMATION: Xaa is Leu or Gln
<220> FEATURE:
<221> NAME/KEY: MISC_FEATURE
<222> LOCATION: (4)..(4)
<223> OTHER INFORMATION: Xaa is Asn or Ser
<220> FEATURE:
<221> NAME/KEY: MISC_FEATURE
<222> LOCATION: (5)..(5)
```

<223> OTHER INFORMATION: Xaa is Glu, Gln, or Asn
<220> FEATURE:
<221> NAME/KEY: MISC_FEATURE
<222> LOCATION: (6)..(6)
<223> OTHER INFORMATION: Xaa is Asp or Trp
<220> FEATURE:
<221> NAME/KEY: MISC_FEATURE
<222> LOCATION: (8)..(8)
<223> OTHER INFORMATION: Xaa is Leu or Ser

<400> SEQUENCE: 30

Xaa Xaa Ser Xaa Xaa Xaa Leu Xaa Thr
1               5

<210> SEQ ID NO 31
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 31

Gly Tyr Thr Phe Ser Ser Tyr Tyr Met Ile
1               5                   10

<210> SEQ ID NO 32
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 32

Met Gly Asp Ile Asn Pro Tyr Asn Gly Gly Ala Asn Tyr Ala Gln Lys
1               5                   10                  15

Phe Gln Gly

<210> SEQ ID NO 33
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 33

Glu Gly Pro Tyr Phe Ser Asn Leu Tyr Val Met Asp Tyr
1               5                   10

<210> SEQ ID NO 34
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 34

Arg Ala Ser Gln Ser Val Ser Tyr Gln Gly Glu Asn Tyr Leu Ala
1               5                   10                  15

<210> SEQ ID NO 35
<211> LENGTH: 7
<212> TYPE: PRT
<213> ORGANISM: Artificial Sequence
<220> FEATURE:

```
<223> OTHER INFORMATION: anti-CSF1R antibody molecule or antigen-binding
      portion LCDR2

<400> SEQUENCE: 35

Asp Ala Ser Asn Arg Ala Thr
1               5

<210> SEQ ID NO 36
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 36

Gln Leu Ser Asn Gln Asp Leu Leu Thr
1               5

<210> SEQ ID NO 37
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 37

Arg Ala Ser Gln Ser Val Ser Tyr Glu Gly Glu Asn Tyr Leu Asn
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 38

Ala Ala Ser Asn Arg Ala Thr
1               5

<210> SEQ ID NO 39
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 39

Gln Leu Ser Asn Glu Asp Leu Leu Thr
1               5

<210> SEQ ID NO 40
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 40

Arg Ala Ser Gln Ser Val Ser Tyr Glu Gly Glu Asn Tyr Leu Ala
1               5                   10                  15
```

```
<210> SEQ ID NO 41
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 41

Gly Tyr Thr Phe Thr Ser Tyr Tyr Met Ile
1               5                   10

<210> SEQ ID NO 42
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 42

Met Gly Asp Ile Asn Pro Tyr Asn Gly Gly Thr Thr Tyr Ala Gln Lys
1               5                   10                  15

Phe Gln Gly

<210> SEQ ID NO 43
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 43

Ala Ala Ser Asn Leu Ala Thr
1               5

<210> SEQ ID NO 44
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 44

Met Gly Asp Ile Asn Pro Tyr Asn Gly Gly Ala Asn Phe Ala Gln Lys
1               5                   10                  15

Phe Gln Gly

<210> SEQ ID NO 45
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 45

Arg Ala Ser Gln Ser Val Glu Tyr Gln Gly Asp Asn Tyr Leu Asn
1               5                   10                  15

<210> SEQ ID NO 46
<211> LENGTH: 10
<212> TYPE: PRT
<213> ORGANISM: Artificial Sequence
<220> FEATURE:
```

```
<223> OTHER INFORMATION: anti-CSF1R antibody molecule or antigen-binding
      portion HCDR1

<400> SEQUENCE: 46

Gly Tyr Thr Phe Thr Ser Tyr Tyr Ile Ile
1               5                   10

<210> SEQ ID NO 47
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 47

Met Gly Asp Ile Asn Pro Tyr Asn Gly Gly Ala Thr Tyr Ala Gln Lys
1               5                   10                  15

Phe Gln Gly

<210> SEQ ID NO 48
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 48

Glu Pro Pro Tyr Phe Ser Asn Leu Tyr Val Met Asp Tyr
1               5                   10

<210> SEQ ID NO 49
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 49

Arg Ala Ser Gln Ser Val Glu Tyr Glu Gly Asp Asn Tyr Leu Asn
1               5                   10                  15

<210> SEQ ID NO 50
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 50

Gly Tyr Thr Phe Ser Ser Asn Tyr Met Ile
1               5                   10

<210> SEQ ID NO 51
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 51

Met Gly Asp Ile Asn Pro Tyr Asn Gly Gly Ala Thr Tyr Asn Gln Lys
1               5                   10                  15
```

Phe Gln Gly

<210> SEQ ID NO 52
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 52

Arg Ala Ser Gln Ser Val Glu Tyr Glu Gly Glu Asn Tyr Leu Asn
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 53

Arg Ala Ser Gln Ser Val Glu Tyr Gln Gly Glu Asn Tyr Leu Asn
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 54

Gly Tyr Thr Phe Thr Ser Asn Tyr Ile Ile
1               5                   10

<210> SEQ ID NO 55
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 55

Met Gly Asp Ile Asn Pro Tyr Asn Gly Gly Thr Asn Tyr Ala Gln Lys
1               5                   10                  15
Phe Gln Gly

<210> SEQ ID NO 56
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 56

Gln Leu Ser Ser Glu Asp Leu Leu Thr
1               5

<210> SEQ ID NO 57
<211> LENGTH: 10
<212> TYPE: PRT

```
<213> ORGANISM: Artificial Sequence
<220> FEATURE:
<223> OTHER INFORMATION: anti-CSF1R antibody molecule or antigen-binding
      portion HCDR1

<400> SEQUENCE: 57

Gly Tyr Thr Phe Ser Ser Ala Tyr Met Ile
1               5                   10

<210> SEQ ID NO 58
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 58

Gly Tyr Thr Phe Ser Ser Ser Tyr Met Ile
1               5                   10

<210> SEQ ID NO 59
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 59

Gly Tyr Thr Phe Ser Ser His Tyr Met Ile
1               5                   10

<210> SEQ ID NO 60
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 60

Ala Ala Ser Asp Arg Ala Thr
1               5

<210> SEQ ID NO 61
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1
<220> FEATURE:
<221> NAME/KEY: misc_feature
<222> LOCATION: (2)..(2)
<223> OTHER INFORMATION: Xaa is Tyr or Gly
<220> FEATURE:
<221> NAME/KEY: misc_feature
<222> LOCATION: (5)..(5)
<223> OTHER INFORMATION: Xaa is Thr or Ser
<220> FEATURE:
<221> NAME/KEY: misc_feature
<222> LOCATION: (6)..(6)
<223> OTHER INFORMATION: Xaa is Asp or Ser
<220> FEATURE:
<221> NAME/KEY: misc_feature
<222> LOCATION: (7)..(7)
<223> OTHER INFORMATION: Xaa is Asn, Ala, Ser, His or Tyr
<220> FEATURE:
<221> NAME/KEY: misc_feature
<222> LOCATION: (8)..(8)
```

```
<223> OTHER INFORMATION: Xaa is Tyr or Ala
<220> FEATURE:
<221> NAME/KEY: misc_feature
<222> LOCATION: (9)..(9)
<223> OTHER INFORMATION: Xaa is Met or Ile

<400> SEQUENCE: 61

Gly Xaa Thr Phe Xaa Xaa Xaa Xaa Xaa Ile
1               5                   10

<210> SEQ ID NO 62
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2
<220> FEATURE:
<221> NAME/KEY: MISC_FEATURE
<222> LOCATION: (5)..(5)
<223> OTHER INFORMATION: Xaa is Asn or Ile
<220> FEATURE:
<221> NAME/KEY: MISC_FEATURE
<222> LOCATION: (7)..(7)
<223> OTHER INFORMATION: Xaa is Tyr or Ile
<220> FEATURE:
<221> NAME/KEY: MISC_FEATURE
<222> LOCATION: (8)..(8)
<223> OTHER INFORMATION: Xaa is Asn or Phe
<220> FEATURE:
<221> NAME/KEY: MISC_FEATURE
<222> LOCATION: (10)..(10)
<223> OTHER INFORMATION: Xaa is Gly or Thr
<220> FEATURE:
<221> NAME/KEY: MISC_FEATURE
<222> LOCATION: (11)..(11)
<223> OTHER INFORMATION: Xaa is Thr or Ala
<220> FEATURE:
<221> NAME/KEY: MISC_FEATURE
<222> LOCATION: (12)..(12)
<223> OTHER INFORMATION: Xaa is Thr or Asn
<220> FEATURE:
<221> NAME/KEY: MISC_FEATURE
<222> LOCATION: (13)..(13)
<223> OTHER INFORMATION: Xaa is Phe or Tyr
<220> FEATURE:
<221> NAME/KEY: MISC_FEATURE
<222> LOCATION: (14)..(14)
<223> OTHER INFORMATION: Xaa is Asn or Ala

<400> SEQUENCE: 62

Met Gly Asp Ile Xaa Pro Tyr Xaa Gly Xaa Xaa Xaa Xaa Xaa Gln Lys
1               5                   10                  15

Phe Gln Gly

<210> SEQ ID NO 63
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3
<220> FEATURE:
<221> NAME/KEY: MISC_FEATURE
<222> LOCATION: (1)..(1)
<223> OTHER INFORMATION: Xaa is Glu or Asp
<220> FEATURE:
<221> NAME/KEY: MISC_FEATURE
<222> LOCATION: (2)..(2)
<223> OTHER INFORMATION: Xaa is Asp, Gly, His, Ser, Thr, Pro, Val, Asn,
      Ile, or Tyr
<220> FEATURE:
<221> NAME/KEY: MISC_FEATURE
<222> LOCATION: (3)..(3)
```

```
<223> OTHER INFORMATION: Xaa is Pro, Thr, Asn, Glu, Leu, Ala, Asp, or
      Ser
<220> FEATURE:
<221> NAME/KEY: MISC_FEATURE
<222> LOCATION: (4)..(4)
<223> OTHER INFORMATION: Xaa is Tyr, Lys, Arg, Met, or Pro
<220> FEATURE:
<221> NAME/KEY: MISC_FEATURE
<222> LOCATION: (5)..(5)
<223> OTHER INFORMATION: Xaa is Phe, Asp, Ser, Thr, Glu, Trp, Met, Tyr,
      Leu, Gln, Lys, Gly, Ala, or Ile
<220> FEATURE:
<221> NAME/KEY: MISC_FEATURE
<222> LOCATION: (6)..(6)
<223> OTHER INFORMATION: Xaa is Ser, Glu, Gly, or Arg
<220> FEATURE:
<221> NAME/KEY: MISC_FEATURE
<222> LOCATION: (7)..(7)
<223> OTHER INFORMATION: Xaa is Asn, Glu, Gln, Gly, His, or Met
<220> FEATURE:
<221> NAME/KEY: MISC_FEATURE
<222> LOCATION: (8)..(8)
<223> OTHER INFORMATION: Xaa is Leu, His, Ser, or Tyr
<220> FEATURE:
<221> NAME/KEY: MISC_FEATURE
<222> LOCATION: (9)..(9)
<223> OTHER INFORMATION: Xaa is Tyr or Trp

<400> SEQUENCE: 63

Xaa Xaa Xaa Xaa Xaa Xaa Xaa Xaa Xaa Val Met Asp Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (7)..(7)
<223> OTHER INFORMATION: Xaa is Asn, Ala, Ser, His or Tyr
<220> FEATURE:
<221> NAME/KEY: MISC_FEATURE
<222> LOCATION: (9)..(9)
<223> OTHER INFORMATION: Xaa is Met or Ile
<220> FEATURE:
<221> NAME/KEY: MISC_FEATURE
<222> LOCATION: (10)..(10)
<223> OTHER INFORMATION: Xaa is Ile or Ser

<400> SEQUENCE: 64

Gly Tyr Thr Phe Xaa Ser Xaa Tyr Xaa Xaa
1               5                   10

<210> SEQ ID NO 65
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2
<220> FEATURE:
<221> NAME/KEY: misc_feature
<222> LOCATION: (10)..(10)
<223> OTHER INFORMATION: Xaa is Gly or Thr
<220> FEATURE:
<221> NAME/KEY: misc_feature
<222> LOCATION: (11)..(11)
<223> OTHER INFORMATION: Xaa is Thr or Ala
```

```
<220> FEATURE:
<221> NAME/KEY: misc_feature
<222> LOCATION: (12)..(12)
<223> OTHER INFORMATION: Xaa is Thr or Asn
<220> FEATURE:
<221> NAME/KEY: misc_feature
<222> LOCATION: (14)..(14)
<223> OTHER INFORMATION: Xaa is Asn or Ala

<400> SEQUENCE: 65

Met Gly Asp Ile Asn Pro Tyr Asn Gly Xaa Xaa Xaa Tyr Xaa Gln Lys
1               5                   10                  15

Phe Gln Gly

<210> SEQ ID NO 66
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3
<220> FEATURE:
<221> NAME/KEY: misc_feature
<222> LOCATION: (2)..(2)
<223> OTHER INFORMATION: Xaa is Gly, Pro or Asp

<400> SEQUENCE: 66

Glu Xaa Pro Tyr Phe Ser Asn Leu Tyr Val Met Asp Tyr
1               5                   10

<210> SEQ ID NO 67
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2
<220> FEATURE:
<221> NAME/KEY: misc_feature
<222> LOCATION: (1)..(1)
<223> OTHER INFORMATION: Xaa is Ala or Asp
<220> FEATURE:
<221> NAME/KEY: misc_feature
<222> LOCATION: (4)..(4)
<223> OTHER INFORMATION: Xaa is Asp or Asn
<220> FEATURE:
<221> NAME/KEY: misc_feature
<222> LOCATION: (5)..(5)
<223> OTHER INFORMATION: Xaa is Leu or Arg
<220> FEATURE:
<221> NAME/KEY: misc_feature
<222> LOCATION: (6)..(6)
<223> OTHER INFORMATION: Xaa is Glu or Ala

<400> SEQUENCE: 67

Xaa Ala Ser Xaa Xaa Xaa Thr
1               5

<210> SEQ ID NO 68
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3
<220> FEATURE:
<221> NAME/KEY: misc_feature
<222> LOCATION: (1)..(1)
<223> OTHER INFORMATION: Xaa is Gln, His or Asn
<220> FEATURE:
<221> NAME/KEY: misc_feature
<222> LOCATION: (2)..(2)
```

```
<223> OTHER INFORMATION: Xaa is Leu or Gln
<220> FEATURE:
<221> NAME/KEY: misc_feature
<222> LOCATION: (4)..(4)
<223> OTHER INFORMATION: Xaa is Asn or Ser
<220> FEATURE:
<221> NAME/KEY: misc_feature
<222> LOCATION: (5)..(5)
<223> OTHER INFORMATION: Xaa is Glu, Gln or Asn

<400> SEQUENCE: 68

Xaa Xaa Ser Xaa Xaa Asp Leu Leu Thr
1               5

<210> SEQ ID NO 69
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1
<220> FEATURE:
<221> NAME/KEY: misc_feature
<222> LOCATION: (7)..(7)
<223> OTHER INFORMATION: Xaa is Ser or Glu
<220> FEATURE:
<221> NAME/KEY: misc_feature
<222> LOCATION: (9)..(9)
<223> OTHER INFORMATION: Xaa is Glu or Gln
<220> FEATURE:
<221> NAME/KEY: misc_feature
<222> LOCATION: (11)..(11)
<223> OTHER INFORMATION: Xaa is Asp or Glu
<220> FEATURE:
<221> NAME/KEY: misc_feature
<222> LOCATION: (15)..(15)
<223> OTHER INFORMATION: Xaa is Asn or Ala

<400> SEQUENCE: 69

Arg Ala Ser Gln Ser Val Xaa Tyr Xaa Gly Xaa Asn Tyr Leu Xaa
1               5                   10                  15

<210> SEQ ID NO 70
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2
<220> FEATURE:
<221> NAME/KEY: misc_feature
<222> LOCATION: (1)..(1)
<223> OTHER INFORMATION: Xaa is Ala or Asp
<220> FEATURE:
<221> NAME/KEY: misc_feature
<222> LOCATION: (4)..(4)
<223> OTHER INFORMATION: Xaa is Asp or Asn
<220> FEATURE:
<221> NAME/KEY: misc_feature
<222> LOCATION: (5)..(5)
<223> OTHER INFORMATION: Xaa is Leu or Arg

<400> SEQUENCE: 70

Xaa Ala Ser Xaa Xaa Ala Thr
1               5

<210> SEQ ID NO 71
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3
```

```
<220> FEATURE:
<221> NAME/KEY: misc_feature
<222> LOCATION: (5)..(5)
<223> OTHER INFORMATION: Xaa is Glu or Gln

<400> SEQUENCE: 71

Gln Leu Ser Asn Xaa Asp Leu Leu Thr
1               5

<210> SEQ ID NO 72
<211> LENGTH: 5
<212> TYPE: PRT
<213> ORGANISM: Homo sapiens

<400> SEQUENCE: 72

Arg Asp Glu Leu Thr
1               5

<210> SEQ ID NO 73
<211> LENGTH: 4
<212> TYPE: PRT
<213> ORGANISM: Homo sapiens

<400> SEQUENCE: 73

Arg Glu Glu Met
1

<210> SEQ ID NO 74
<211> LENGTH: 5
<212> TYPE: PRT
<213> ORGANISM: Artificial Sequence
<220> FEATURE:
<223> OTHER INFORMATION: amino acid motif

<400> SEQUENCE: 74

Tyr Asp Gly Asp Asn
1               5

<210> SEQ ID NO 75
<211> LENGTH: 9
<212> TYPE: PRT
<213> ORGANISM: Artificial Sequence
<220> FEATURE:
<223> OTHER INFORMATION: TCED+ and LAF peptide

<400> SEQUENCE: 75

Phe Ala Val Tyr Tyr Cys His Leu Ser
1               5

<210> SEQ ID NO 76
<211> LENGTH: 9
<212> TYPE: PRT
<213> ORGANISM: Artificial Sequence
<220> FEATURE:
<223> OTHER INFORMATION: TCED+ and LAF peptide

<400> SEQUENCE: 76

Ile Tyr Ala Ala Ser Asn Leu Glu Ser
1               5

<210> SEQ ID NO 77
<211> LENGTH: 9
<212> TYPE: PRT
<213> ORGANISM: Artificial Sequence
<220> FEATURE:
<223> OTHER INFORMATION: LAF peptide
```

```
<400> SEQUENCE: 77

Phe Lys Gly Arg Val Thr Ile Thr Ala
1               5

<210> SEQ ID NO 78
<211> LENGTH: 10
<212> TYPE: PRT
<213> ORGANISM: Mus musculus

<400> SEQUENCE: 78

Gly Tyr Thr Phe Thr Asp Asn Tyr Met Ile
1               5                   10

<210> SEQ ID NO 79
<211> LENGTH: 5
<212> TYPE: PRT
<213> ORGANISM: Mus musculus

<400> SEQUENCE: 79

Asp Asn Tyr Met Ile
1               5

<210> SEQ ID NO 80
<211> LENGTH: 7
<212> TYPE: PRT
<213> ORGANISM: Mus musculus

<400> SEQUENCE: 80

Gly Tyr Thr Phe Thr Asp Asn
1               5

<210> SEQ ID NO 81
<211> LENGTH: 9
<212> TYPE: PRT
<213> ORGANISM: Mus musculus

<400> SEQUENCE: 81

Gly Tyr Thr Phe Thr Asp Asn Tyr Met
1               5

<210> SEQ ID NO 82
<211> LENGTH: 6
<212> TYPE: PRT
<213> ORGANISM: Mus musculus

<400> SEQUENCE: 82

Thr Asp Asn Tyr Met Ile
1               5

<210> SEQ ID NO 83
<211> LENGTH: 19
<212> TYPE: PRT
<213> ORGANISM: Mus musculus

<400> SEQUENCE: 83

Ile Gly Asp Ile Asn Pro Tyr Asn Gly Gly Thr Thr Phe Asn Gln Lys
1               5                   10                  15

Phe Lys Gly

<210> SEQ ID NO 84
<211> LENGTH: 17
<212> TYPE: PRT
<213> ORGANISM: Mus musculus
```

```
<400> SEQUENCE: 84

Asp Ile Asn Pro Tyr Asn Gly Gly Thr Thr Phe Asn Gln Lys Phe Lys
1               5                   10                  15

Gly

<210> SEQ ID NO 85
<211> LENGTH: 6
<212> TYPE: PRT
<213> ORGANISM: Mus musculus

<400> SEQUENCE: 85

Asn Pro Tyr Asn Gly Gly
1               5

<210> SEQ ID NO 86
<211> LENGTH: 7
<212> TYPE: PRT
<213> ORGANISM: Mus musculus

<400> SEQUENCE: 86

Ile Asn Pro Tyr Asn Gly Gly
1               5

<210> SEQ ID NO 87
<211> LENGTH: 16
<212> TYPE: PRT
<213> ORGANISM: Mus musculus

<400> SEQUENCE: 87

Ile Asn Pro Tyr Asn Gly Gly Thr Thr Phe Asn Gln Lys Phe Lys Gly
1               5                   10                  15

<210> SEQ ID NO 88
<211> LENGTH: 10
<212> TYPE: PRT
<213> ORGANISM: Mus musculus

<400> SEQUENCE: 88

Asp Ile Asn Pro Tyr Asn Gly Gly Thr Thr
1               5                   10

<210> SEQ ID NO 89
<211> LENGTH: 12
<212> TYPE: PRT
<213> ORGANISM: Mus musculus

<400> SEQUENCE: 89

Ile Gly Asp Ile Asn Pro Tyr Asn Gly Gly Thr Thr
1               5                   10

<210> SEQ ID NO 90
<211> LENGTH: 13
<212> TYPE: PRT
<213> ORGANISM: Mus musculus

<400> SEQUENCE: 90

Glu Ser Pro Tyr Phe Ser Asn Leu Tyr Val Met Asp Tyr
1               5                   10

<210> SEQ ID NO 91
<211> LENGTH: 15
<212> TYPE: PRT
<213> ORGANISM: Mus musculus
```

<400> SEQUENCE: 91

Ala Arg Glu Ser Pro Tyr Phe Ser Asn Leu Tyr Val Met Asp Tyr
1               5                   10                  15

<210> SEQ ID NO 92
<211> LENGTH: 12
<212> TYPE: PRT
<213> ORGANISM: Mus musculus

<400> SEQUENCE: 92

Glu Ser Pro Tyr Phe Ser Asn Leu Tyr Val Met Asp
1               5                   10

<210> SEQ ID NO 93
<211> LENGTH: 15
<212> TYPE: PRT
<213> ORGANISM: Mus musculus

<400> SEQUENCE: 93

Ala Arg Glu Ser Pro Tyr Phe Ser Asn Leu Tyr Val Met Asp Tyr
1               5                   10                  15

<210> SEQ ID NO 94
<211> LENGTH: 15
<212> TYPE: PRT
<213> ORGANISM: Mus musculus

<400> SEQUENCE: 94

Lys Ala Ser Gln Ser Val Asp Tyr Asp Gly Asp Asn Tyr Met Asn
1               5                   10                  15

<210> SEQ ID NO 95
<211> LENGTH: 10
<212> TYPE: PRT
<213> ORGANISM: Mus musculus

<400> SEQUENCE: 95

Gln Ser Val Asp Tyr Asp Gly Asp Asn Tyr
1               5                   10

<210> SEQ ID NO 96
<211> LENGTH: 12
<212> TYPE: PRT
<213> ORGANISM: Mus musculus

<400> SEQUENCE: 96

Ala Ser Gln Ser Val Asp Tyr Asp Gly Asp Asn Tyr
1               5                   10

<210> SEQ ID NO 97
<211> LENGTH: 11
<212> TYPE: PRT
<213> ORGANISM: Mus musculus

<400> SEQUENCE: 97

Asp Tyr Asp Gly Asp Asn Tyr Met Asn Trp Tyr
1               5                   10

<210> SEQ ID NO 98
<211> LENGTH: 7
<212> TYPE: PRT
<213> ORGANISM: Mus musculus

<400> SEQUENCE: 98

Ala Ala Ser Asn Leu Glu Ser
1               5

<210> SEQ ID NO 99
<211> LENGTH: 10
<212> TYPE: PRT
<213> ORGANISM: Mus musculus

<400> SEQUENCE: 99

Leu Leu Ile Tyr Ala Ala Ser Asn Leu Glu
1               5                   10

<210> SEQ ID NO 100
<211> LENGTH: 9
<212> TYPE: PRT
<213> ORGANISM: Mus musculus

<400> SEQUENCE: 100

His Leu Ser Asn Glu Asp Leu Ser Thr
1               5

<210> SEQ ID NO 101
<211> LENGTH: 6
<212> TYPE: PRT
<213> ORGANISM: Mus musculus

<400> SEQUENCE: 101

Ser Asn Glu Asp Leu Ser
1               5

<210> SEQ ID NO 102
<211> LENGTH: 8
<212> TYPE: PRT
<213> ORGANISM: Mus musculus

<400> SEQUENCE: 102

His Leu Ser Asn Glu Asp Leu Ser
1               5

<210> SEQ ID NO 103
<211> LENGTH: 122
<212> TYPE: PRT
<213> ORGANISM: Mus musculus

<400> SEQUENCE: 103

Glu Val Gln Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Asp Asn
                20                  25                  30

Tyr Met Ile Trp Val Lys Gln Ser His Gly Lys Ser Leu Glu Trp Ile
            35                  40                  45

Gly Asp Ile Asn Pro Tyr Asn Gly Gly Thr Thr Phe Asn Gln Lys Phe
    50                  55                  60

Lys Gly Lys Ala Thr Leu Thr Val Glu Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Ser Pro Tyr Phe Ser Asn Leu Tyr Val Met Asp Tyr Trp
                100                 105                 110

Gly Gln Gly Thr Ser Val Thr Val Ser Ser
            115                 120

```
<210> SEQ ID NO 104
<211> LENGTH: 122
<212> TYPE: PRT
<213> ORGANISM: Artificial Sequence
<220> FEATURE:
<223> OTHER INFORMATION: Hu0301-VH IGHV1-69

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
            35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
                100                 105                 110

Gly Gln Gly Thr Leu Val Thr Val Ser Ser
            115                 120

<210> SEQ ID NO 105
<211> LENGTH: 122
<212> TYPE: PRT
<213> ORGANISM: Artificial Sequence
<220> FEATURE:
<223> OTHER INFORMATION: VH-graft IGHV1-69

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
            35                  40                  45

Gly Asp Ile Asn Pro Tyr Asn Gly Gly Thr Thr Phe Asn Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
                100                 105                 110

Gly Gln Gly Thr Leu Val Thr Val Ser Ser
            115                 120

<210> SEQ ID NO 106
<211> LENGTH: 111
<212> TYPE: PRT
<213> ORGANISM: Mus musculus

<400> SEQUENCE: 106

Asn Ile Val Leu Thr Gln Ser Pro Ala Ser Leu Ala Val Ser Leu Gly
1               5                   10                  15
```

Gln Arg Ala Thr Ile Ser Cys Lys Ala Ser Gln Ser Val Asp Tyr Asp
            20                  25                  30

Gly Asp Asn Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His Leu Ser Asn
                85                  90                  95

Glu Asp Leu Ser Thr Phe Gly Gly Gly Thr Lys Leu Glu Ile Lys
            100                 105                 110

<210> SEQ ID NO 107
<211> LENGTH: 111
<212> TYPE: PRT
<213> ORGANISM: Artificial Sequence
<220> FEATURE:
<223> OTHER INFORMATION: Hu0301-VL IGKV3-11

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
            35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 108
<211> LENGTH: 111
<212> TYPE: PRT
<213> ORGANISM: Artificial Sequence
<220> FEATURE:
<223> OTHER INFORMATION: VL-graft IGKV3-11

<400> SEQUENCE: 108

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asp
            20                  25                  30

Gly Asp Asn Tyr Met Asn Trp Tyr Gln Gln Lys Pro Gly Gln Ala Pro
            35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 109
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 109

Arg Ala Ser Gln Ser Val Ser Tyr Asp Gly Glu Asn Tyr Leu Asn
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 110

Arg Ala Ser Gln Ser Val Ser Tyr Glu Gly Asp Asn Tyr Leu Asn
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 111

Arg Ala Ser Gln Ser Val Glu Tyr Asp Gly Glu Asn Tyr Leu Asn
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 112

Arg Ala Ser Gln Ser Val Glu Tyr Gln Gly Asp Asn Tyr Leu Ala
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 113

Arg Ala Ser Gln Ser Val Asp Tyr Glu Gly Glu Asn Tyr Leu Asn
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 114

Arg Ala Ser Gln Ser Val Asp Tyr Asp Gly Asp Asn Tyr Leu Asn
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 115

Arg Ala Ser Gln Ser Val Ser Tyr Gln Gly Glu Asn Tyr Leu Asn
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 116

Arg Ala Ser Gln Ser Val Asp Tyr Asp Gly Glu Asn Tyr Leu Asn
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 117

Arg Ala Ser Gln Ser Val Ser Tyr Gln Gly Asp Asn Tyr Leu Asn
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 118

Arg Ala Ser Gln Ser Val Asp Tyr Glu Gly Asp Asn Tyr Leu Asn
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 119

Arg Ala Ser Gln Ser Val Asp Tyr Gln Gly Glu Asn Tyr Leu Asn
1               5                   10                  15

<210> SEQ ID NO 120
<211> LENGTH: 15

```
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 120

Arg Ala Ser Gln Ser Val Glu Tyr Asp Gly Asp Asn Tyr Leu Asn
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 121

Arg Ala Ser Gln Ser Val Ser Tyr Asp Gly Asp Asn Tyr Leu Asn
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 122

Arg Ala Ser Gln Ser Val Ser Tyr Asp Gly Glu Asn Tyr Leu Ala
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 123

Arg Ala Ser Gln Ser Val Glu Tyr Asp Gly Asp Asn Tyr Leu Ala
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 124

Arg Ala Ser Gln Ser Val Ser Tyr Asp Gly Asp Asn Tyr Leu Ala
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 125

Arg Ala Ser Gln Ser Val Glu Tyr Asp Gly Glu Asn Tyr Leu Ala
```

```
<210> SEQ ID NO 126
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 126

Arg Ala Ser Gln Ser Val Glu Tyr Gln Gly Glu Asn Tyr Leu Ala
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 127

Arg Ala Ser Gln Ser Val Asp Tyr Gln Gly Asp Asn Tyr Leu Asn
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 128

Arg Ala Ser Gln Ser Val Asp Tyr Asp Gly Glu Asn Tyr Leu Ala
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 129

Arg Ala Ser Gln Ser Val Ser Tyr Asn Gly Asp Asn Tyr Leu Asn
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 130

Arg Ala Ser Gln Ser Val Glu Tyr His Gly Asp Asn Tyr Leu Asn
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
```

```
            portion LCDR1

<400> SEQUENCE: 131

Arg Ala Ser Gln Ser Val Asp Tyr Gln Gly Asp Asn Tyr Leu Ala
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 132

Arg Ala Ser Gln Ser Val Asp Tyr Asp Gly Asp Asn Tyr Leu Ala
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 133

Arg Ala Ser Gln Ser Val Glu Tyr Glu Gly Asp Asn Tyr Leu Ala
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 134

Arg Ala Ser Gln Ser Val Asp Tyr Glu Gly Glu Asn Tyr Leu Ala
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 135

Arg Ala Ser Gln Ser Val Glu Tyr Glu Gly Glu Asn Tyr Leu Ala
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 136

Arg Ala Ser Gln Ser Val Asp Tyr Glu Gly Asp Asn Tyr Leu Ala
1               5                   10                  15

<210> SEQ ID NO 137
```

```
<211> LENGTH: 15
<212> TYPE: PRT
<213> ORGANISM: Artificial Sequence
<220> FEATURE:
<223> OTHER INFORMATION: anti-CSF1R antibody molecule or antigen-binding
      portion LCDR1

<400> SEQUENCE: 137

Arg Ala Ser Gln Ser Val Asp Tyr Gln Gly Glu Asn Tyr Leu Ala
1               5                   10                  15

<210> SEQ ID NO 138
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 138

Ala Ala Ser Asn Leu Glu Thr
1               5

<210> SEQ ID NO 139
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 139

Ala Ala Ser Asn Arg Glu Thr
1               5

<210> SEQ ID NO 140
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 140

Asp Ala Ser Asn Leu Ala Thr
1               5

<210> SEQ ID NO 141
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 141

Asp Ala Ser Asn Arg Glu Thr
1               5

<210> SEQ ID NO 142
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 142
```

Asp Ala Ser Asn Leu Glu Thr
1               5

<210> SEQ ID NO 143
<211> LENGTH: 7
<212> TYPE: PRT
<213> ORGANISM: Artificial Sequence
<220> FEATURE:
<223> OTHER INFORMATION: anti-CSF1R antibody molecule or antigen-binding
      portion LCDR2

<400> SEQUENCE: 143

Gly Ala Ser Asn Arg Ala Thr
1               5

<210> SEQ ID NO 144
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 144

His Leu Ser Asn Glu Asp Leu Leu Thr
1               5

<210> SEQ ID NO 145
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 145

Gln Leu Ser Asn Glu Trp Leu Leu Thr
1               5

<210> SEQ ID NO 146
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 146

Gln Leu Ser Asn Glu Asp Leu Ser Thr
1               5

<210> SEQ ID NO 147
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 147

Gln Leu Ser Ser Glu Trp Leu Leu Thr
1               5

<210> SEQ ID NO 148
<211> LENGTH: 9
<212> TYPE: PRT
<213> ORGANISM: Artificial Sequence
<220> FEATURE:

```
<223> OTHER INFORMATION: anti-CSF1R antibody molecule or antigen-binding
      portion LCDR3

<400> SEQUENCE: 148

Gln Leu Ser Asn Asn Asp Leu Leu Thr
1               5

<210> SEQ ID NO 149
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 149

Gln Leu Ser Ser Gln Asp Leu Leu Thr
1               5

<210> SEQ ID NO 150
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 150

His Leu Ser Asn Gln Asp Leu Leu Thr
1               5

<210> SEQ ID NO 151
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 151

Gln Gln Ser Asn Gln Asp Leu Leu Thr
1               5

<210> SEQ ID NO 152
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 152

Gln Leu Ser Asn Glu Trp Leu Ser Thr
1               5

<210> SEQ ID NO 153
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 153

Gln Leu Ser Asn Gln Trp Leu Leu Thr
1               5
```

```
<210> SEQ ID NO 154
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 154

Asn Leu Ser Asn Glu Asp Leu Leu Thr
1               5

<210> SEQ ID NO 155
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 155

Gln Leu Ser Asn Gln Asp Leu Ser Thr
1               5

<210> SEQ ID NO 156
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 156

His Leu Ser Asn Asn Asp Leu Leu Thr
1               5

<210> SEQ ID NO 157
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 157

His Leu Ser Asn Gln Asp Leu Ser Thr
1               5

<210> SEQ ID NO 158
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 158

Gln Gln Ser Asn Glu Asp Leu Leu Thr
1               5

<210> SEQ ID NO 159
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 159
```

Gln Leu Ser Ser Glu Asp Leu Ser Thr
1               5

<210> SEQ ID NO 160
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 160

His Gln Ser Asn Glu Asp Leu Leu Thr
1               5

<210> SEQ ID NO 161
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 161

Gln Leu Ser Ser Asn Asp Leu Leu Thr
1               5

<210> SEQ ID NO 162
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 162

Gln Leu Ser Asn Asn Asp Leu Ser Thr
1               5

<210> SEQ ID NO 163
<211> LENGTH: 9
<212> TYPE: PRT
<213> ORGANISM: Artificial Sequence
<220> FEATURE:
<223> OTHER INFORMATION: anti-CSF1R antibody molecule or antigen-binding
      portion LCDR3

<400> SEQUENCE: 163

Gln Gln Ser Ser Glu Asp Leu Leu Thr
1               5

<210> SEQ ID NO 164
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 164

Gly Tyr Thr Phe Thr Ser Asn Tyr Met Ile
1               5                   10

<210> SEQ ID NO 165
<211> LENGTH: 10
<212> TYPE: PRT
<213> ORGANISM: Artificial Sequence

```
<220> FEATURE:
<223> OTHER INFORMATION: anti-CSF1R antibody molecule or antigen-binding
      portion HCDR1

<400> SEQUENCE: 165

Gly Tyr Thr Phe Thr Asp Tyr Tyr Met Ile
1               5                   10

<210> SEQ ID NO 166
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 166

Gly Tyr Thr Phe Ser Asp Asn Tyr Met Ile
1               5                   10

<210> SEQ ID NO 167
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 167

Gly Tyr Thr Phe Ser Ser Asn Tyr Ile Ile
1               5                   10

<210> SEQ ID NO 168
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 168

Gly Tyr Thr Phe Thr Asp Asn Tyr Ile Ile
1               5                   10

<210> SEQ ID NO 169
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 169

Gly Tyr Thr Phe Ser Asp Asn Tyr Ile Ile
1               5                   10

<210> SEQ ID NO 170
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 170

Gly Gly Thr Phe Ser Ser Asn Tyr Ile Ile
1               5                   10
```

<210> SEQ ID NO 171
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 171

Gly Tyr Thr Phe Ser Asp Tyr Tyr Met Ile
1               5                   10

<210> SEQ ID NO 172
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 172

Gly Tyr Thr Phe Ser Ser Tyr Tyr Ile Ile
1               5                   10

<210> SEQ ID NO 173
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 173

Gly Tyr Thr Phe Thr Asp Tyr Tyr Ile Ser
1               5                   10

<210> SEQ ID NO 174
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 174

Gly Gly Thr Phe Ser Asp Tyr Tyr Met Ile
1               5                   10

<210> SEQ ID NO 175
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 175

Gly Gly Thr Phe Thr Ser Tyr Tyr Met Ile
1               5                   10

<210> SEQ ID NO 176
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

```
<400> SEQUENCE: 176

Gly Tyr Thr Phe Thr Ser Tyr Tyr Ile Ser
1               5                   10

<210> SEQ ID NO 177
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 177

Gly Tyr Thr Phe Thr Ser Tyr Tyr Met Ser
1               5                   10

<210> SEQ ID NO 178
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 178

Gly Tyr Thr Phe Ser Ser Asn Tyr Ile Ser
1               5                   10

<210> SEQ ID NO 179
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 179

Gly Tyr Thr Phe Ser Ser Asn Tyr Met Ser
1               5                   10

<210> SEQ ID NO 180
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 180

Gly Gly Thr Phe Ser Asp Asn Tyr Met Ile
1               5                   10

<210> SEQ ID NO 181
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 181

Gly Tyr Thr Phe Ser Ser Tyr Tyr Met Ser
1               5                   10

<210> SEQ ID NO 182
<211> LENGTH: 10
<212> TYPE: PRT
```

```
<213> ORGANISM: Artificial Sequence
<220> FEATURE:
<223> OTHER INFORMATION: anti-CSF1R antibody molecule or antigen-binding
      portion HCDR1

<400> SEQUENCE: 182

Gly Tyr Thr Phe Thr Asp Tyr Tyr Ile Ile
1               5                   10

<210> SEQ ID NO 183
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 183

Gly Tyr Thr Phe Thr Asp Asn Tyr Ile Ser
1               5                   10

<210> SEQ ID NO 184
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 184

Gly Tyr Thr Phe Thr Asp Asn Tyr Met Ser
1               5                   10

<210> SEQ ID NO 185
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 185

Gly Tyr Thr Phe Ser Ser Tyr Tyr Ile Ser
1               5                   10

<210> SEQ ID NO 186
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 186

Gly Tyr Thr Phe Thr Ser Asn Tyr Ile Ser
1               5                   10

<210> SEQ ID NO 187
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 187

Gly Tyr Thr Phe Ser Asp Tyr Tyr Ile Ser
1               5                   10
```

<210> SEQ ID NO 188
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 188

Gly Gly Thr Phe Thr Asp Tyr Tyr Met Ile
1               5                   10

<210> SEQ ID NO 189
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 189

Gly Tyr Thr Phe Ser Asp Asn Tyr Ile Ser
1               5                   10

<210> SEQ ID NO 190
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 190

Gly Tyr Thr Phe Thr Asp Tyr Tyr Met Ser
1               5                   10

<210> SEQ ID NO 191
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 191

Gly Gly Thr Phe Thr Asp Asn Tyr Ile Ile
1               5                   10

<210> SEQ ID NO 192
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 192

Gly Gly Thr Phe Thr Ser Asn Tyr Ile Ile
1               5                   10

<210> SEQ ID NO 193
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

```
<400> SEQUENCE: 193

Gly Tyr Thr Phe Thr Ser Asn Tyr Met Ser
1               5                   10

<210> SEQ ID NO 194
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 194

Gly Tyr Thr Phe Ser Asp Tyr Tyr Met Ser
1               5                   10

<210> SEQ ID NO 195
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 195

Gly Gly Thr Phe Thr Asp Tyr Tyr Ile Ser
1               5                   10

<210> SEQ ID NO 196
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 196

Met Gly Asp Ile Asn Pro Tyr Asn Gly Thr Thr Thr Phe Ala Gln Lys
1               5                   10                  15

Phe Gln Gly

<210> SEQ ID NO 197
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 197

Met Gly Asp Ile Asn Pro Tyr Asn Gly Gly Thr Thr Tyr Asn Gln Lys
1               5                   10                  15

Phe Gln Gly

<210> SEQ ID NO 198
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 198

Met Gly Asp Ile Asn Pro Tyr Asn Gly Thr Ala Thr Tyr Ala Gln Lys
1               5                   10                  15
```

Phe Gln Gly

<210> SEQ ID NO 199
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 199

Met Gly Asp Ile Asn Pro Tyr Asn Gly Gly Thr Thr Phe Ala Gln Lys
1               5                   10                  15

Phe Gln Gly

<210> SEQ ID NO 200
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 200

Met Gly Asp Ile Asn Pro Tyr Asn Gly Gly Thr Asn Phe Ala Gln Lys
1               5                   10                  15

Phe Gln Gly

<210> SEQ ID NO 201
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 201

Met Gly Asp Ile Asn Pro Tyr Asn Gly Gly Thr Thr Phe Asn Gln Lys
1               5                   10                  15

Phe Lys Gly

<210> SEQ ID NO 202
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 202

Met Gly Asp Ile Asn Pro Tyr Asn Gly Gly Ala Thr Phe Ala Gln Lys
1               5                   10                  15

Phe Gln Gly

<210> SEQ ID NO 203
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 203

Met Gly Asp Ile Asn Pro Tyr Asn Gly Thr Thr Thr Phe Asn Gln Lys

Phe Gln Gly

<210> SEQ ID NO 204
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 204

Met Gly Asp Ile Asn Pro Tyr Asn Gly Gly Ala Asn Tyr Asn Gln Lys
1               5                   10                  15

Phe Gln Gly

<210> SEQ ID NO 205
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 205

Met Gly Asp Ile Asn Pro Tyr Asn Gly Gly Thr Asn Tyr Asn Gln Lys
1               5                   10                  15

Phe Gln Gly

<210> SEQ ID NO 206
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 206

Met Gly Asp Ile Asn Pro Tyr Asn Gly Gly Thr Asn Phe Asn Gln Lys
1               5                   10                  15

Phe Gln Gly

<210> SEQ ID NO 207
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 207

Met Gly Asp Ile Asn Pro Tyr Asn Gly Thr Ala Asn Tyr Asn Gln Lys
1               5                   10                  15

Phe Gln Gly

<210> SEQ ID NO 208
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 208

Met Gly Asp Ile Asn Pro Tyr Asn Gly Thr Ala Asn Phe Asn Gln Lys
1               5                   10                  15

Phe Gln Gly

<210> SEQ ID NO 209
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 209

Met Gly Asp Ile Asn Pro Tyr Phe Gly Gly Thr Thr Tyr Ala Gln Lys
1               5                   10                  15

Phe Gln Gly

<210> SEQ ID NO 210
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 210

Met Gly Asp Ile Asn Pro Tyr Asn Gly Gly Ala Thr Phe Asn Gln Lys
1               5                   10                  15

Phe Gln Gly

<210> SEQ ID NO 211
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 211

Met Gly Asp Ile Asn Pro Tyr Asn Gly Thr Ala Asn Tyr Ala Gln Lys
1               5                   10                  15

Phe Gln Gly

<210> SEQ ID NO 212
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 212

Met Gly Asp Ile Asn Pro Tyr Asn Gly Thr Ala Thr Tyr Asn Gln Lys
1               5                   10                  15

Phe Gln Gly

<210> SEQ ID NO 213
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 213

```
<210> SEQ ID NO 214
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 214

Met Gly Asp Ile Asn Pro Tyr Asn Gly Thr Thr Thr Tyr Asn Gln Lys
1               5                   10                  15

Phe Gln Gly

<210> SEQ ID NO 214
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 214

Met Gly Asp Ile Asn Pro Tyr Asn Gly Thr Ala Asn Phe Ala Gln Lys
1               5                   10                  15

Phe Gln Gly

<210> SEQ ID NO 215
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 215

Met Gly Asp Ile Asn Pro Tyr Asn Gly Thr Thr Thr Tyr Ala Gln Lys
1               5                   10                  15

Phe Gln Gly

<210> SEQ ID NO 216
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 216

Met Gly Asp Ile Asn Pro Tyr Asn Gly Gly Ala Asn Phe Asn Gln Lys
1               5                   10                  15

Phe Gln Gly

<210> SEQ ID NO 217
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 217

Met Gly Asp Ile Asn Pro Tyr Asn Gly Thr Thr Asn Tyr Ala Gln Lys
1               5                   10                  15

Phe Gln Gly

<210> SEQ ID NO 218
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2
```

```
<400> SEQUENCE: 218

Met Gly Asp Ile Asn Pro Tyr Asn Gly Thr Ala Thr Phe Ala Gln Lys
1               5                   10                  15

Phe Gln Gly

<210> SEQ ID NO 219
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 219

Met Gly Asp Ile Asn Pro Tyr Asn Gly Thr Thr Asn Tyr Asn Gln Lys
1               5                   10                  15

Phe Gln Gly

<210> SEQ ID NO 220
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 220

Met Gly Asp Ile Asn Pro Tyr Phe Gly Thr Thr Tyr Asn Gln Lys
1               5                   10                  15

Phe Gln Gly

<210> SEQ ID NO 221
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 221

Met Gly Asp Ile Asn Pro Tyr Asn Gly Thr Ala Thr Phe Asn Gln Lys
1               5                   10                  15

Phe Gln Gly

<210> SEQ ID NO 222
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 222

Met Gly Asp Ile Asn Pro Tyr Asn Gly Thr Thr Asn Phe Asn Gln Lys
1               5                   10                  15

Phe Gln Gly

<210> SEQ ID NO 223
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2
```

<400> SEQUENCE: 223

Met Gly Asp Ile Asn Pro Tyr Phe Gly Gly Ala Thr Tyr Ala Gln Lys
1               5                   10                  15

Phe Gln Gly

<210> SEQ ID NO 224
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 224

Met Gly Asp Ile Asn Pro Tyr Phe Gly Thr Thr Thr Tyr Ala Gln Lys
1               5                   10                  15

Phe Gln Gly

<210> SEQ ID NO 225
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 225

Met Gly Asp Ile Asn Pro Tyr Phe Gly Gly Ala Thr Tyr Asn Gln Lys
1               5                   10                  15

Phe Gln Gly

<210> SEQ ID NO 226
<211> LENGTH: 19
<212> TYPE: PRT
<213> ORGANISM: Artificial Sequence
<220> FEATURE:
<223> OTHER INFORMATION: anti-CSF1R antibody molecule or antigen-binding
      portion HCDR2

<400> SEQUENCE: 226

Met Gly Asp Ile Asn Pro Tyr Asn Gly Thr Thr Asn Phe Ala Gln Lys
1               5                   10                  15

Phe Gln Gly

<210> SEQ ID NO 227
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 227

Glu Gly Pro Tyr Phe Gly Asn Leu Tyr Val Met Asp Tyr
1               5                   10

<210> SEQ ID NO 228
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

```
<400> SEQUENCE: 228

Glu Ser Asp Tyr Phe Ser Asn Leu Tyr Val Met Asp Tyr
1               5                   10

<210> SEQ ID NO 229
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 229

Glu Val Pro Tyr Phe Ser Asn Leu Tyr Val Met Asp Tyr
1               5                   10

<210> SEQ ID NO 230
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 230

Glu Asp Pro Tyr Phe Ser Asn Leu Tyr Val Met Asp Tyr
1               5                   10

<210> SEQ ID NO 231
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 231

Glu Ser Pro Tyr Thr Ser Asn Leu Tyr Val Met Asp Tyr
1               5                   10

<210> SEQ ID NO 232
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 232

Glu Pro Pro Tyr Phe Arg Asn Leu Tyr Val Met Asp Tyr
1               5                   10

<210> SEQ ID NO 233
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 233

Glu Ser Pro Tyr Asp Ser Asn Leu Tyr Val Met Asp Tyr
1               5                   10

<210> SEQ ID NO 234
<211> LENGTH: 13
<212> TYPE: PRT
```

```
<213> ORGANISM: Artificial Sequence
<220> FEATURE:
<223> OTHER INFORMATION: anti-CSF1R antibody molecule or antigen-binding
      portion HCDR3

<400> SEQUENCE: 234

Glu Thr Pro Tyr Phe Ser Asn Leu Tyr Val Met Asp Tyr
1               5                   10

<210> SEQ ID NO 235
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 235

Glu His Pro Tyr Phe Ser Asn Leu Tyr Val Met Asp Tyr
1               5                   10

<210> SEQ ID NO 236
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 236

Glu Ser Pro Tyr Ala Ser Asn Leu Tyr Val Met Asp Tyr
1               5                   10

<210> SEQ ID NO 237
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 237

Glu Ser Pro Tyr Ile Ser Asn Leu Tyr Val Met Asp Tyr
1               5                   10

<210> SEQ ID NO 238
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 238

Glu His Pro Tyr Ser Ser Asn Leu Tyr Val Met Asp Tyr
1               5                   10

<210> SEQ ID NO 239
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 239

Glu Ser Ala Tyr Phe Ser Asn Leu Tyr Val Met Asp Tyr
1               5                   10
```

```
<210> SEQ ID NO 240
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 240

Glu Gly Pro Tyr Phe Arg Asn Leu Tyr Val Met Asp Tyr
1               5                   10

<210> SEQ ID NO 241
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 241

Glu Gly Pro Tyr Phe Glu Asn Leu Tyr Val Met Asp Tyr
1               5                   10

<210> SEQ ID NO 242
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 242

Glu Ser Pro Tyr His Ser Asn Leu Tyr Val Met Asp Tyr
1               5                   10

<210> SEQ ID NO 243
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 243

Glu Ser Pro Tyr Arg Ser Asn Leu Tyr Val Met Asp Tyr
1               5                   10

<210> SEQ ID NO 244
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 244

Glu Ser Pro Tyr Met Ser Asn Leu Tyr Val Met Asp Tyr
1               5                   10

<210> SEQ ID NO 245
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3
```

```
<400> SEQUENCE: 245

Glu Gly Pro Lys Phe Ser Asn Leu Tyr Val Met Asp Tyr
1               5                   10

<210> SEQ ID NO 246
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 246

Glu Ser Leu Tyr Phe Ser Asn Leu Tyr Val Met Asp Tyr
1               5                   10

<210> SEQ ID NO 247
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 247

Glu His Pro Tyr Phe Ser Gln Leu Tyr Val Met Asp Tyr
1               5                   10

<210> SEQ ID NO 248
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 248

Glu Ser Pro Tyr Gln Ser Asn Leu Tyr Val Met Asp Tyr
1               5                   10

<210> SEQ ID NO 249
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 249

Glu Ser Glu Tyr Phe Ser Asn Leu Tyr Val Met Asp Tyr
1               5                   10

<210> SEQ ID NO 250
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 250

Glu Asn Pro Tyr Phe Ser Asn Leu Tyr Val Met Asp Tyr
1               5                   10

<210> SEQ ID NO 251
<211> LENGTH: 13
```

```
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 251

Glu Ile Pro Tyr Phe Ser Asn Leu Tyr Val Met Asp Tyr
1               5                   10

<210> SEQ ID NO 252
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 252

Glu Pro Pro Tyr Phe Ser Asn Leu Tyr Val Ile Asp Tyr
1               5                   10

<210> SEQ ID NO 253
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 253

Glu Ser Ser Tyr Phe Ser Asn Leu Tyr Val Met Asp Tyr
1               5                   10

<210> SEQ ID NO 254
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 254

Glu Ser Pro Tyr Gly Ser Asn Leu Tyr Val Met Asp Tyr
1               5                   10

<210> SEQ ID NO 255
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 255

Glu Pro Pro Tyr Leu Ser Asn Leu Tyr Val Met Asp Tyr
1               5                   10

<210> SEQ ID NO 256
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 256

Glu Pro Pro Tyr Phe Ser Asn Leu Tyr Val Ala Asp Tyr
```

```
1               5                   10
```

<210> SEQ ID NO 257
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 257

```
Glu Ser Pro Tyr Lys Ser Asn Leu Tyr Val Met Asp Tyr
1               5                   10
```

<210> SEQ ID NO 258
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 258

```
Glu Gly Pro Tyr Arg Ser Asn Leu Tyr Val Met Asp Tyr
1               5                   10
```

<210> SEQ ID NO 259
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 259

```
Glu Ser Pro Arg Phe Ser Asn Leu Tyr Val Met Asp Tyr
1               5                   10
```

<210> SEQ ID NO 260
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 260

```
Glu Ser Pro Met Phe Ser Asn Leu Tyr Val Met Asp Tyr
1               5                   10
```

<210> SEQ ID NO 261
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 261

```
Glu Tyr Pro Tyr Phe Ser Asn Leu Tyr Val Met Asp Tyr
1               5                   10
```

<210> SEQ ID NO 262
<211> LENGTH: 13
<212> TYPE: PRT
<213> ORGANISM: Artificial Sequence
<220> FEATURE:
<223> OTHER INFORMATION: anti-CSF1R antibody molecule or antigen-binding portion HCDR3

<400> SEQUENCE: 262

Glu Gly Pro Tyr Gln Ser Asn Leu Tyr Val Met Asp Tyr
1               5                   10

<210> SEQ ID NO 263
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 263

Glu Asp Pro Tyr Phe Ser Asn Leu Trp Val Met Asp Tyr
1               5                   10

<210> SEQ ID NO 264
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 264

Glu Ser Pro Tyr Phe Ser Asn Tyr Tyr Val Met Asp Tyr
1               5                   10

<210> SEQ ID NO 265
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 265

Glu Ser Pro Pro Phe Ser Asn Leu Tyr Val Met Asp Tyr
1               5                   10

<210> SEQ ID NO 266
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 266

Glu Gly Pro Tyr Leu Ser Asn Leu Tyr Val Met Asp Tyr
1               5                   10

<210> SEQ ID NO 267
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 267

Glu Ser Asn Tyr Phe Ser Asn Leu Tyr Val Met Asp Tyr
1               5                   10

<210> SEQ ID NO 268

```
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 268

Glu Gly Pro Tyr Tyr Ser Asn Leu Tyr Val Met Asp Tyr
1               5                   10

<210> SEQ ID NO 269
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 269

Glu Gly Pro Tyr Met Ser Asn Leu Tyr Val Met Asp Tyr
1               5                   10

<210> SEQ ID NO 270
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 270

Glu Ser Pro Tyr Phe Ser Gly Leu Tyr Val Met Asp Tyr
1               5                   10

<210> SEQ ID NO 271
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 271

Glu Arg Pro Tyr Phe Ser Asn Leu Tyr Val Met Asp Tyr
1               5                   10

<210> SEQ ID NO 272
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 272

Glu Ser Thr Tyr Phe Ser Asn Leu Tyr Val Met Asp Tyr
1               5                   10

<210> SEQ ID NO 273
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 273
```

```
Glu Gly Pro Tyr Thr Ser Asn Leu Tyr Val Met Asp Tyr
1               5                   10
```

<210> SEQ ID NO 274
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 274

```
Glu Gly Pro Tyr Asp Ser Asn Leu Tyr Val Met Asp Tyr
1               5                   10
```

<210> SEQ ID NO 275
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 275

```
Glu Pro Pro Tyr Phe Gly Asn Leu Tyr Val Met Asp Tyr
1               5                   10
```

<210> SEQ ID NO 276
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 276

```
Glu Gly Pro Tyr Phe Asp Asn Leu Tyr Val Met Asp Tyr
1               5                   10
```

<210> SEQ ID NO 277
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 277

```
Glu Pro Pro Tyr Phe Ser Asn Ser Tyr Val Met Asp Tyr
1               5                   10
```

<210> SEQ ID NO 278
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 278

```
Glu Gly Pro Tyr Phe Ser His Leu Tyr Val Met Asp Tyr
1               5                   10
```

<210> SEQ ID NO 279
<211> LENGTH: 13
<212> TYPE: PRT
<213> ORGANISM: Artificial Sequence
<220> FEATURE:

<223> OTHER INFORMATION: anti-CSF1R antibody molecule or antigen-binding
      portion HCDR3

<400> SEQUENCE: 279

Glu Gly Pro Tyr Phe Ser Met Leu Tyr Val Met Asp Tyr
1               5                   10

<210> SEQ ID NO 280
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 280

Glu Pro Pro Tyr Phe Ser Asn His Tyr Val Met Asp Tyr
1               5                   10

<210> SEQ ID NO 281
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 281

Glu Ser Pro Tyr Trp Ser Asn Leu Tyr Val Met Asp Tyr
1               5                   10

<210> SEQ ID NO 282
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 282

Glu Gly Pro Tyr Glu Ser Asn Leu Tyr Val Met Asp Tyr
1               5                   10

<210> SEQ ID NO 283
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 283

Glu Pro Pro Tyr Phe Ser Glu Leu Tyr Val Met Asp Tyr
1               5                   10

<210> SEQ ID NO 284
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 284

Glu Gly Pro Tyr Ser Ser Asn Leu Tyr Val Met Asp Tyr
1               5                   10

```
<210> SEQ ID NO 285
<211> LENGTH: 13
<212> TYPE: PRT
<213> ORGANISM: Artificial Sequence
<220> FEATURE:
<223> OTHER INFORMATION: anti-CSF1R antibody molecule or antigen-binding
      portion HCDR3

<400> SEQUENCE: 285

Asp Ser Pro Tyr Phe Ser Asn Leu Tyr Val Met Asp Tyr
1               5                   10

<210> SEQ ID NO 286
<211> LENGTH: 10
<212> TYPE: PRT
<213> ORGANISM: Artificial Sequence
<220> FEATURE:
<223> OTHER INFORMATION: anti-CSF1R antibody molecule or antigen-binding
      portion HCDR1

<400> SEQUENCE: 286

Gly Gly Thr Phe Ser Ser Tyr Tyr Ile Ile
1               5                   10

<210> SEQ ID NO 287
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 287

Tyr Tyr Met Ile Trp Val Arg Gln Ala
1               5

<210> SEQ ID NO 288
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 288

Ala Tyr Met Ile Trp Val Arg Gln Ala
1               5

<210> SEQ ID NO 289
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 289

Asp Tyr Met Ile Trp Val Arg Gln Ala
1               5

<210> SEQ ID NO 290
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 290

Gly Tyr Met Ile Trp Val Arg Gln Ala
1               5
```

<210> SEQ ID NO 291
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 291

His Tyr Met Ile Trp Val Arg Gln Ala
1               5

<210> SEQ ID NO 292
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 292

Asn Tyr Met Ile Trp Val Arg Gln Ala
1               5

<210> SEQ ID NO 293
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 293

Ser Tyr Met Ile Trp Val Arg Gln Ala
1               5

<210> SEQ ID NO 294
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 294

Thr Tyr Met Ile Trp Val Arg Gln Ala
1               5

<210> SEQ ID NO 295
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 295

Tyr Asp Met Ile Trp Val Arg Gln Ala
1               5

<210> SEQ ID NO 296
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 296

Tyr Tyr Met Gly Trp Val Arg Gln Ala
1               5

```
<210> SEQ ID NO 297
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 297

Tyr Tyr Met His Trp Val Arg Gln Ala
1               5

<210> SEQ ID NO 298
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 298

Tyr Tyr Met Asn Trp Val Arg Gln Ala
1               5

<210> SEQ ID NO 299
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 299

Tyr Tyr Met Ser Trp Val Arg Gln Ala
1               5

<210> SEQ ID NO 300
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 300

Tyr Tyr Met Thr Trp Val Arg Gln Ala
1               5

<210> SEQ ID NO 301
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 301

Tyr Tyr Met Trp Trp Val Arg Gln Ala
1               5

<210> SEQ ID NO 302
<211> LENGTH: 9
<212> TYPE: PRT
<213> ORGANISM: Artificial Sequence
<220> FEATURE:
<223> OTHER INFORMATION: T cell epitope in antibody variable region

<400> SEQUENCE: 302

Tyr Tyr Met Tyr Trp Val Arg Gln Ala
1               5

<210> SEQ ID NO 303
```

<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 303

Phe Ser Asn Leu Tyr Val Met Asp Tyr Trp Gly Gln
1 5 10

<210> SEQ ID NO 304
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 304

Ala Ser Asn Leu Tyr Val Met Asp Tyr Trp Gly Gln
1 5 10

<210> SEQ ID NO 305
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 305

His Ser Asn Leu Tyr Val Met Asp Tyr Trp Gly Gln
1 5 10

<210> SEQ ID NO 306
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 306

Thr Ser Asn Leu Tyr Val Met Asp Tyr Trp Gly Gln
1 5 10

<210> SEQ ID NO 307
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 307

Phe Ser Asn Asp Tyr Val Met Asp Tyr Trp Gly Gln
1 5 10

<210> SEQ ID NO 308
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 308

Phe Ser Asn Gly Tyr Val Met Asp Tyr Trp Gly Gln
1 5 10

<210> SEQ ID NO 309
<211> LENGTH: 12

```
<212> TYPE: PRT
<213> ORGANISM: Artificial Sequence
<220> FEATURE:
<223> OTHER INFORMATION: T cell epitope in antibody variable region

<400

```
<213> ORGANISM: Artificial Sequence
<220> FEATURE:
<223> OTHER INFORMATION: T cell epitope in antibody variable region

<400> SE

```
<220> FEATURE:
<223> OTHER INFORMATION: T cell epitope in antibody variable region

<400> SEQUENCE: 321

Phe Ser Asn Leu Tyr Val His Asp Tyr Trp Gly Gln
1               5                   10

<210> SEQ ID NO 322
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 322

Phe Ser Asn Leu Tyr Val Pro Asp Tyr Trp Gly Gln
1               5                   10

<210> SEQ ID NO 323
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 323

Phe Ser Asn Leu Tyr Val Ser Asp Tyr Trp Gly Gln
1               5                   10

<210> SEQ ID NO 324
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 324

Phe Ser Asn Leu Tyr Val Thr Asp Tyr Trp Gly Gln
1               5                   10

<210> SEQ ID NO 325
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 325

Phe Ser Asn Leu Tyr Val Trp Asp Tyr Trp Gly Gln
1               5                   10

<210> SEQ ID NO 326
<211> LENGTH: 12
<212> TYPE: PRT
<213> ORGANISM: Artificial Sequence
<220> FEATURE:
<223> OTHER INFORMATION: T cell epitope in antibody variable region

<400> SEQUENCE: 326

Phe Ser Asn Leu Tyr Val Met Asp Tyr Trp Gly Lys
1               5                   10

<210> SEQ ID NO 327
<211> LENGTH: 12
<212> TYPE: PRT
<213> ORGANISM: Artificial Sequence
<220> FEATURE:
```

<223> OTHER INFORMATION: T cell epitope in antibody variable region

<400> SEQUENCE: 327

Phe Ser Asn Leu Tyr Val Met Asp Tyr Trp Gly Arg
1 5 10

<210> SEQ ID NO 328
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 328

Leu Leu Ile Tyr Ala Ala Ser Asn Arg Ala
1 5 10

<210> SEQ ID NO 329
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 329

Ala Leu Ile Tyr Ala Ala Ser Asn Arg Ala
1 5 10

<210> SEQ ID NO 330
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 330

Arg Leu Ile Tyr Ala Ala Ser Asn Arg Ala
1 5 10

<210> SEQ ID NO 331
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 331

Ser Leu Ile Tyr Ala Ala Ser Asn Arg Ala
1 5 10

<210> SEQ ID NO 332
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 332

Thr Leu Ile Tyr Ala Ala Ser Asn Arg Ala
1 5 10

<210> SEQ ID NO 333
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 333

Leu Ala Ile Tyr Ala Ala Ser Asn Arg Ala
1               5                   10

<210> SEQ ID NO 334
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 334

Leu Leu Leu Tyr Ala Ala Ser Asn Arg Ala
1               5                   10

<210> SEQ ID NO 335
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 335

Leu Leu Ile His Ala Ala Ser Asn Arg Ala
1               5                   10

<210> SEQ ID NO 336
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 336

Leu Leu Ile Lys Ala Ala Ser Asn Arg Ala
1               5                   10

<210> SEQ ID NO 337
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 337

Leu Leu Ile Ser Ala Ala Ser Asn Arg Ala
1               5                   10

<210> SEQ ID NO 338
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 338

Leu Leu Ile Tyr Asp Ala Ser Asn Arg Ala
1               5                   10

<210> SEQ ID NO 339
<211> LENGTH: 10
<212> TYPE: PRT
<213> ORGANISM: Artificial Sequence
<220> FEATURE:
<223> OTHER INFORMATION: T cell epitope in antibody variable region

```
<400> SEQUENCE: 339

Leu Leu Ile Tyr Glu Ala Ser Asn Arg Ala
1               5                   10

<210> SEQ ID NO 340
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 340

Leu Leu Ile Tyr Thr Ala Ser Asn Arg Ala
1               5                   10

<210> SEQ ID NO 341
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 341

Leu Leu Ile Tyr Ala Asp Ser Asn Arg Ala
1               5                   10

<210> SEQ ID NO 342
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 342

Leu Leu Ile Tyr Ala Gly Ser Asn Arg Ala
1               5                   10

<210> SEQ ID NO 343
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 343

Leu Leu Ile Tyr Ala Ala Asp Asn Arg Ala
1               5                   10

<210> SEQ ID NO 344
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 344

Leu Leu Ile Tyr Ala Ala Gly Asn Arg Ala
1               5                   10

<210> SEQ ID NO 345
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 345
```

Leu Leu Ile Tyr Ala Ala Ser Asp Arg Ala
1 5 10

<210> SEQ ID NO 346
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 346

Leu Leu Ile Tyr Ala Ala Ser Glu Arg Ala
1 5 10

<210> SEQ ID NO 347
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 347

Leu Leu Ile Tyr Ala Ala Ser Asn Arg Asp
1 5 10

<210> SEQ ID NO 348
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 348

Leu Leu Ile Tyr Ala Ala Ser Asn Arg Glu
1 5 10

<210> SEQ ID NO 349
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 349

Leu Leu Ile Tyr Ala Ala Ser Asn Arg Gly
1 5 10

<210> SEQ ID NO 350
<211> LENGTH: 10
<212> TYPE: PRT
<213> ORGANISM: Artificial Sequence
<220> FEATURE:
<223> OTHER INFORMATION: T cell epitope in antibody variable region

<400> SEQUENCE: 350

Leu Leu Ile Tyr Ala Ala Ser Asn Arg Pro
1 5 10

<210> SEQ ID NO 351
<211> LENGTH: 111
<212> TYPE: PRT
<213> ORGANISM: Artificial Sequence
<220> FEATURE:
<223> OTHER INFORMATION: Antibody MH5 light chain variable (VL) region

<400> SEQUENCE: 351

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Glu
            20                  25                  30

Gly Glu Asn Tyr Leu Asn Trp Tyr Gln Gln Lys Pro Gly Gln Ala Pro
        35                  40                  45

Arg Leu Leu Ile Tyr Ala Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Pro Glu Pro Glu Asp Phe Ala Val Tyr Tyr Cys Gln Leu Ser Asn
                85                  90                  95

Glu Asp Leu Leu Thr Phe Gly Gly Gly Thr Lys Val Glu Ile Lys
            100                 105                 110
```

<210> SEQ ID NO 352
<211> LENGTH: 122
<212> TYPE: PRT
<213> ORGANISM: Artificial Sequence
<220> FEATURE:
<223> OTHER INFORMATION: Antibody MH5 heavy chain variable (VH) region

<400> SEQUENCE: 352

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Phe Ser Asn Leu Tyr Val Met Asp Tyr Trp
            100                 105                 110

Gly Gln Gly Thr Leu Val Thr Val Ser Ser
        115                 120
```

<210> SEQ ID NO 353
<211> LENGTH: 122
<212> TYPE: PRT
<213> ORGANISM: Artificial Sequence
<220> FEATURE:
<223> OTHER INFORMATION: Antibody MH12 light chain variable (VL) region

<400> SEQUENCE: 353

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu Gly Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 354
<211> LENGTH: 111
<212> TYPE: PRT
<213> ORGANISM: Artificial Sequence
<220> FEATURE:
<223> OTHER INFORMATION: Antibody MH12 heavy chain variable (VH) region

<400> SEQUENCE: 354

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Glu
            20                  25                  30

Gly Glu Asn Tyr Leu Asn Trp Tyr Gln Gln Lys Pro Gly Gln Ala Pro
        35                  40                  45

Arg Ser Leu Ile Tyr Ala Ala Ser Asp Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Pro Glu Pro Glu Asp Phe Ala Val Tyr Tyr Cys Gln Leu Ser Asn
                85                  90                  95

Glu Asp Leu Leu Thr Phe Gly Gly Gly Thr Lys Val Glu Ile Lys
            100                 105                 110

<210> SEQ ID NO 355
<211> LENGTH: 122
<212> TYPE: PRT
<213> ORGANISM: Artificial Sequence
<220> FEATURE:
<223> OTHER INFORMATION: Antibody MH16 light chain variable (VL) region

<400> SEQUENCE: 355

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Ala
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 356
<211> LENGTH: 111
<212> TYPE: PRT
```

```
<213> ORGANISM: Artificial Sequence
<220> FEATURE:
<223> OTHER INFORMATION: Antibody MH16 heavy chain variable (VH) region

<400> SEQUENCE: 356

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Glu
            20                  25                  30

Gly Glu Asn Tyr Leu Asn Trp Tyr Gln Gln Lys Pro Gly Gln Ala Pro
        35                  40                  45

Arg Ser Leu Ile Tyr Ala Ala Ser Asp Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Pro Glu Pro Glu Asp Phe Ala Val Tyr Tyr Cys Gln Leu Ser Asn
                85                  90                  95

Glu Asp Leu Leu Thr Phe Gly Gly Gly Thr Lys Val Glu Ile Lys
            100                 105                 110

<210> SEQ ID NO 357
<211> LENGTH: 111
<212> TYPE: PRT
<213> ORGANISM: Artificial Sequence
<220> FEATURE:
<223> OTHER INFORMATION: Antibody 30E06 light chain variable (VL) region

<400> SEQUENCE: 357

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Glu
            20                  25                  30

Gly Glu Asn Tyr Leu Ala Trp Tyr Gln Gln Lys Pro Gly Gln Ala Pro
        35                  40                  45

Arg Leu Leu Ile Tyr Ala Ala Ser Asn Leu Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Leu Ser Asn
                85                  90                  95

Glu Asp Leu Leu Thr Phe Gly Gly Gly Thr Lys Val Glu Ile Lys
            100                 105                 110

<210> SEQ ID NO 358
<211> LENGTH: 122
<212> TYPE: PRT
<213> ORGANISM: Artificial Sequence
<220> FEATURE:
<223> OTHER INFORMATION: Antibody 30E06 heavy chain variable (VH) region

<400> SEQUENCE: 358

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Tyr Ala Gln Lys Phe
    50                  55                  60
```

```
Gln Gly Arg Val Thr Ile Thr Ala Asp Glu Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Pro Tyr Phe Ser Asn Leu Tyr Val Met Asp Tyr Trp
            100                 105                 110

Gly Gln Gly Thr Leu Val Thr Val Ser Ser
            115                 120

<210> SEQ ID NO 359
<211> LENGTH: 327
<212> TYPE: PRT
<213> ORGANISM: Homo sapiens

<400> SEQUENCE: 359

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
```

305 310 315 320

Leu Ser Leu Ser Leu Gly Lys
            325

<210> SEQ ID NO 360
<211> LENGTH: 327
<212> TYPE: PRT
<213> ORGANISM: Homo sapiens

<400> SEQUENCE: 360

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 361
<211> LENGTH: 330

```
<212> TYPE: PRT
<213> ORGANISM: Homo sapiens

<400> SEQUENCE: 361

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 362
<211> LENGTH: 330
<212> TYPE: PRT
<213> ORGANISM: Homo sapiens

<400> SEQUENCE: 362

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 363
<211> LENGTH: 330
<212> TYPE: PRT
<213> ORGANISM: Homo sapiens

<400> SEQUENCE: 363

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

-continued

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 364
<211> LENGTH: 329
<212> TYPE: PRT
<213> ORGANISM: Homo sapiens

<400> SEQUENCE: 364

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys

```
                100             105                 110
Pro Ala Pro Glu Ala Ala Gly Ala Pro Ser Val Phe Leu Phe Pro Pro
            115                 120             125

Lys Pro Lys Asp Thr Leu Met Ile Ser Arg Thr Pro Glu Val Thr Cys
    130                 135             140

Val Val Val Asp Val Ser His Glu Asp Pro Glu Val Lys Phe Asn Trp
145                 150             155                 160

Tyr Val Asp Gly Val Glu Val His Asn Ala Lys Thr Lys Pro Arg Glu
                165                 170             175

Glu Gln Tyr Asn Ser Thr Tyr Arg Val Val Ser Val Leu Thr Val Leu
            180                 185             190

His Gln Asp Trp Leu Asn Gly Lys Glu Tyr Lys Cys Lys Val Ser Asn
        195                 200             205

Lys Ala Leu Pro Ala Pro Ile Glu Lys Thr Ile Ser Lys Ala Lys Gly
    210                 215             220

Gln Pro Arg Glu Pro Gln Val Tyr Thr Leu Pro Pro Ser Arg Glu Glu
225                 230             235                 240

Met Lys Asn Gln Val Ser Leu Thr Cys Leu Val Lys Gly Phe Tyr Pro
                245                 250             255

Ser Asp Ile Ala Val Glu Trp Glu Ser Asn Gly Gln Pro Glu Asn Asn
            260                 265             270

Tyr Lys Thr Thr Pro Pro Val Leu Asp Ser Asp Gly Ser Phe Phe Leu
        275                 280             285

Tyr Ser Lys Leu Thr Val Asp Lys Ser Arg Trp Gln Gln Gly Asn Val
    290                 295             300

Phe Ser Cys Ser Val Met His Glu Ala Leu His Asn His Tyr Thr Gln
305                 310             315                 320

Lys Ser Leu Ser Leu Ser Pro Gly Lys
                325

<210> SEQ ID NO 365
<211> LENGTH: 972
<212> TYPE: PRT
<213> ORGANISM: Homo sapiens

<400> SEQUENCE: 365

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25              30

Lys Pro Gly Ala Thr Val Thr Leu Arg Cys Val Gly Asn Gly Ser Val
        35                  40              45

Glu Trp Asp Gly Pro Pro Ser Pro His Trp Thr Leu Tyr Ser Asp Gly
    50                  55              60

Ser Ser Ser Ile Leu Ser Thr Asn Asn Ala Thr Phe Gln Asn Thr Gly
65                  70              75                  80

Thr Tyr Arg Cys Thr Glu Pro Gly Asp Pro Leu Gly Gly Ser Ala Ala
                85                  90              95

Ile His Leu Tyr Val Lys Asp Pro Ala Arg Pro Trp Asn Val Leu Ala
            100                 105             110

Gln Glu Val Val Val Phe Glu Asp Gln Asp Ala Leu Leu Pro Cys Leu
        115                 120             125

Leu Thr Asp Pro Val Leu Glu Ala Gly Val Ser Leu Val Arg Val Arg
    130                 135             140
```

-continued

```
Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
```

```
                565                 570                 575
Phe Pro Arg Asn Asn Leu Gln Phe Gly Lys Thr Leu Gly Ala Gly Ala
                580                 585                 590
Phe Gly Lys Val Val Glu Ala Thr Ala Phe Gly Leu Gly Lys Glu Asp
                595                 600                 605
Ala Val Leu Lys Val Ala Val Lys Met Leu Lys Ser Thr Ala His Ala
        610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
                660                 665                 670
Asn Phe Leu Arg Arg Lys Ala Glu Ala Met Leu Gly Pro Ser Leu Ser
                675                 680                 685
Pro Gly Gln Asp Pro Glu Gly Gly Val Asp Tyr Lys Asn Ile His Leu
        690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
                740                 745                 750
Arg Asp Leu Leu His Phe Ser Ser Gln Val Ala Gln Gly Met Ala Phe
                755                 760                 765
Leu Ala Ser Lys Asn Cys Ile His Arg Asp Val Ala Ala Arg Asn Val
        770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
                820                 825                 830
Thr Val Gln Ser Asp Val Trp Ser Tyr Gly Ile Leu Leu Trp Glu Ile
        835                 840                 845
Phe Ser Leu Gly Leu Asn Pro Tyr Pro Gly Ile Leu Val Asn Ser Lys
                850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
                900                 905                 910
Gln Ala Gln Glu Asp Arg Arg Glu Arg Asp Tyr Thr Asn Leu Pro Ser
        915                 920                 925
Ser Ser Arg Ser Gly Gly Ser Gly Ser Ser Ser Glu Leu Glu Glu
        930                 935                 940
Glu Ser Ser Ser Glu His Leu Thr Cys Cys Glu Gln Gly Asp Ile Ala
945                 950                 955                 960
Gln Pro Leu Leu Gln Pro Asn Asn Tyr Gln Phe Cys
                965                 970

<210> SEQ ID NO 366
```

```
<211> LENGTH: 976
<212> TYPE: PRT
<213> ORGANISM: Macaca fascicularis

<400> SEQUENCE: 366
```

| | | | | | | | | | | | | | | | |
|---|---|---|---|---|---|---|---|---|---|---|---|---|---|---|---|
|Met|Gly|Pro|Gly|Val|Leu|Leu|Leu|Leu|Val|Val|Thr|Ala|Trp|His| |
|1| | | |5| | | | |10| | | | |15| |

| | | | | | | | | | | | | | | | |
|---|---|---|---|---|---|---|---|---|---|---|---|---|---|---|---|
|Gly|Gln|Gly|Ile|Pro|Val|Ile|Glu|Pro|Ser|Gly|Pro|Glu|Leu|Val|Val|
| | | |20| | | |25| | | |30| | | | |

| | | | | | | | | | | | | | | | |
|---|---|---|---|---|---|---|---|---|---|---|---|---|---|---|---|
|Lys|Pro|Gly|Glu|Thr|Val|Thr|Leu|Arg|Cys|Val|Gly|Asn|Gly|Ser|Val|
| | |35| | | |40| | | |45| | | | | |

| | | | | | | | | | | | | | | | |
|---|---|---|---|---|---|---|---|---|---|---|---|---|---|---|---|
|Glu|Trp|Asp|Gly|Pro|Ile|Ser|Pro|His|Trp|Thr|Leu|Tyr|Ser|Asp|Gly|
|50| | | | |55| | | |60| | | | | | |

| | | | | | | | | | | | | | | | |
|---|---|---|---|---|---|---|---|---|---|---|---|---|---|---|---|
|Pro|Ser|Ser|Val|Leu|Thr|Thr|Asn|Asn|Ala|Thr|Phe|Gln|Asn|Thr|Arg|
|65| | | | |70| | | |75| | | | |80| |

| | | | | | | | | | | | | | | | |
|---|---|---|---|---|---|---|---|---|---|---|---|---|---|---|---|
|Thr|Tyr|Arg|Cys|Thr|Glu|Pro|Gly|Asp|Pro|Leu|Gly|Ser|Ala|Ala| |
| | | | |85| | | |90| | | |95| | | |

| | | | | | | | | | | | | | | | |
|---|---|---|---|---|---|---|---|---|---|---|---|---|---|---|---|
|Ile|His|Leu|Tyr|Val|Lys|Asp|Pro|Ala|Arg|Pro|Trp|Asn|Val|Leu|Ala|
| | | |100| | | |105| | | |110| | | | |

| | | | | | | | | | | | | | | | |
|---|---|---|---|---|---|---|---|---|---|---|---|---|---|---|---|
|Lys|Glu|Val|Val|Phe|Glu|Asp|Gln|Asp|Ala|Leu|Leu|Pro|Cys|Leu| |
| | |115| | | |120| | | |125| | | | | |

| | | | | | | | | | | | | | | | |
|---|---|---|---|---|---|---|---|---|---|---|---|---|---|---|---|
|Leu|Thr|Asp|Pro|Val|Leu|Glu|Ala|Gly|Val|Ser|Leu|Val|Arg|Leu|Arg|
|130| | | | |135| | | |140| | | | | | |

| | | | | | | | | | | | | | | | |
|---|---|---|---|---|---|---|---|---|---|---|---|---|---|---|---|
|Gly|Arg|Pro|Leu|Leu|Arg|His|Thr|Asn|Tyr|Ser|Phe|Ser|Pro|Trp|His|
|145| | | | |150| | | |155| | | | |160| |

| | | | | | | | | | | | | | | | |
|---|---|---|---|---|---|---|---|---|---|---|---|---|---|---|---|
|Gly|Phe|Ile|Ile|His|Arg|Ala|Lys|Phe|Ile|Gln|Gly|Gln|Asp|Tyr|Gln|
| | | | |165| | | |170| | | |175| | | |

| | | | | | | | | | | | | | | | |
|---|---|---|---|---|---|---|---|---|---|---|---|---|---|---|---|
|Cys|Ser|Ala|Leu|Met|Gly|Gly|Arg|Lys|Val|Met|Ser|Ile|Ser|Ile|Arg|
| | | |180| | | |185| | | |190| | | | |

| | | | | | | | | | | | | | | | |
|---|---|---|---|---|---|---|---|---|---|---|---|---|---|---|---|
|Leu|Lys|Val|Gln|Lys|Val|Ile|Pro|Gly|Pro|Pro|Ala|Leu|Thr|Leu|Val|
| | |195| | | |200| | | |205| | | | | |

| | | | | | | | | | | | | | | | |
|---|---|---|---|---|---|---|---|---|---|---|---|---|---|---|---|
|Pro|Ala|Glu|Leu|Val|Arg|Ile|Arg|Gly|Glu|Ala|Ala|Gln|Ile|Val|Cys|
| |210| | | | |215| | | |220| | | | | |

| | | | | | | | | | | | | | | | |
|---|---|---|---|---|---|---|---|---|---|---|---|---|---|---|---|
|Ser|Ala|Ser|Asn|Ile|Asp|Val|Asp|Phe|Asp|Val|Phe|Leu|Gln|His|Asn|
|225| | | | |230| | | |235| | | | | |240|

| | | | | | | | | | | | | | | | |
|---|---|---|---|---|---|---|---|---|---|---|---|---|---|---|---|
|Thr|Thr|Lys|Leu|Ala|Ile|Pro|Gln|Arg|Ser|Asp|Phe|His|Asp|Asn|Arg|
| | | |245| | | |250| | | |255| | | | |

| | | | | | | | | | | | | | | | |
|---|---|---|---|---|---|---|---|---|---|---|---|---|---|---|---|
|Tyr|Gln|Lys|Val|Leu|Thr|Leu|Ser|Leu|Gly|Gln|Val|Asp|Phe|Gln|His|
| | | |260| | | |265| | | |270| | | | |

| | | | | | | | | | | | | | | | |
|---|---|---|---|---|---|---|---|---|---|---|---|---|---|---|---|
|Ala|Gly|Asn|Tyr|Ser|Cys|Val|Ala|Ser|Asn|Val|Gln|Gly|Lys|His|Ser|
| | |275| | | |280| | | |285| | | | | |

| | | | | | | | | | | | | | | | |
|---|---|---|---|---|---|---|---|---|---|---|---|---|---|---|---|
|Thr|Ser|Met|Phe|Phe|Arg|Val|Val|Glu|Ser|Ala|Tyr|Leu|Asp|Leu|Ser|
| |290| | | | |295| | | |300| | | | | |

| | | | | | | | | | | | | | | | |
|---|---|---|---|---|---|---|---|---|---|---|---|---|---|---|---|
|Ser|Glu|Gln|Asn|Leu|Ile|Gln|Glu|Val|Thr|Val|Gly|Glu|Gly|Leu|Asn|
|305| | | | |310| | | |315| | | | | |320|

| | | | | | | | | | | | | | | | |
|---|---|---|---|---|---|---|---|---|---|---|---|---|---|---|---|
|Leu|Lys|Val|Met|Val|Glu|Ala|Tyr|Pro|Gly|Leu|Gln|Gly|Phe|Asn|Trp|
| | | |325| | | |330| | | |335| | | | |

| | | | | | | | | | | | | | | | |
|---|---|---|---|---|---|---|---|---|---|---|---|---|---|---|---|
|Thr|Tyr|Leu|Gly|Pro|Phe|Ser|Asp|His|Gln|Pro|Glu|Pro|Lys|Leu|Ala|
| | | |340| | | |345| | | |350| | | | |

| | | | | | | | | | | | | | | | |
|---|---|---|---|---|---|---|---|---|---|---|---|---|---|---|---|
|Asn|Ala|Thr|Thr|Lys|Asp|Thr|Tyr|Arg|His|Thr|Phe|Thr|Leu|Ser|Leu|
| | | |355| | | |360| | | |365| | | | |

| | | | | | | | | | | | | | | | |
|---|---|---|---|---|---|---|---|---|---|---|---|---|---|---|---|
|Pro|Arg|Leu|Lys|Pro|Ser|Glu|Ala|Gly|Arg|Tyr|Ser|Phe|Leu|Ala|Arg|
| |370| | | | |375| | | |380| | | | | |

| | | | | | | | | | | | | | | | |
|---|---|---|---|---|---|---|---|---|---|---|---|---|---|---|---|
|Asn|Pro|Gly|Gly|Trp|Arg|Ala|Leu|Thr|Phe|Glu|Leu|Thr|Leu|Arg|Tyr|

```
                385                 390                 395                 400
        Pro Pro Glu Val Ser Val Ile Trp Thr Ser Ile Asn Gly Ser Gly Thr
                        405                 410                 415

Leu Leu Cys Ala Ala Ser Gly Tyr Pro Gln Pro Asn Val Thr Trp Leu
                        420                 425                 430

Gln Cys Ala Gly His Thr Asp Arg Cys Asp Glu Ala Gln Val Leu Gln
                        435                 440                 445

Val Trp Val Asp Pro His Pro Glu Val Leu Ser Gln Glu Pro Phe Gln
                    450                 455                 460

Lys Val Thr Val Gln Ser Leu Leu Thr Ala Glu Thr Leu Glu His Asn
        465                 470                 475                 480

Gln Thr Tyr Glu Cys Arg Ala His Asn Ser Val Gly Ser Gly Ser Trp
                            485                 490                 495

Ala Phe Ile Pro Ile Ser Ala Gly Ala Arg Thr His Pro Pro Asp Glu
                        500                 505                 510

Phe Leu Phe Thr Pro Val Val Ala Cys Met Ser Val Met Ala Leu
                        515                 520                 525

Leu Leu Leu Leu Leu Leu Leu Leu Tyr Lys Tyr Lys Gln Lys Pro
                530                 535                 540

Lys Tyr Gln Val Arg Trp Lys Ile Ile Glu Ser Tyr Glu Gly Asn Ser
        545                 550                 555                 560

Tyr Thr Phe Ile Asp Pro Thr Gln Leu Pro Tyr Asn Glu Lys Trp Glu
                            565                 570                 575

Phe Pro Arg Asn Asn Leu Gln Phe Gly Lys Thr Leu Gly Ala Gly Ala
                        580                 585                 590

Phe Gly Lys Val Val Glu Ala Thr Ala Phe Gly Leu Gly Lys Glu Asp
                    595                 600                 605

Ala Val Leu Lys Val Ala Val Lys Met Leu Lys Ser Thr Ala His Ala
                        610                 615                 620

Asp Glu Lys Glu Ala Leu Met Ser Glu Leu Lys Ile Met Ser His Leu
        625                 630                 635                 640

Gly Gln His Glu Asn Ile Val Asn Leu Leu Gly Ala Cys Thr His Gly
                            645                 650                 655

Gly Pro Val Leu Val Ile Thr Glu Tyr Cys Cys Tyr Gly Asp Leu Leu
                        660                 665                 670

Asn Phe Leu Arg Arg Lys Ala Glu Ala Met Leu Gly Pro Ser Leu Ser
                        675                 680                 685

Pro Gly Gln Asp Pro Glu Gly Gly Ala Asp Tyr Lys Asn Ile His Leu
        690                 695                 700

Glu Lys Lys Tyr Val Arg Arg Asp Ser Gly Phe Ser Ser Gln Gly Val
        705                 710                 715                 720

Asp Thr Tyr Val Glu Met Arg Pro Val Ser Thr Ser Ser Asn Asp Ser
                            725                 730                 735

Phe Ser Glu Gln Asp Leu Asp Lys Glu Asp Gly Arg Pro Leu Glu Leu
                        740                 745                 750

Trp Asp Leu Leu His Phe Ser Ser Gln Val Ala Gln Gly Met Ala Phe
                        755                 760                 765

Leu Ala Ser Lys Asn Cys Ile His Arg Asp Val Ala Ala Arg Asn Val
                    770                 775                 780

Leu Leu Thr Asn Gly His Val Ala Lys Ile Gly Asp Phe Gly Leu Ala
        785                 790                 795                 800

Arg Asp Ile Met Asn Asp Ser Asn Tyr Ile Val Lys Gly Asn Ala Arg
                            805                 810                 815
```

| | | | | | | | | | | | |
|---|---|---|---|---|---|---|---|---|---|---|---|
|Leu|Pro|Val|Lys 820|Trp|Met|Ala|Pro|Glu 825|Ser|Ile|Phe|Asp|Cys 830|Val|Tyr|

Thr Val Gln Ser Asp Val Trp Ser Tyr Gly Ile Leu Leu Trp Glu Ile
835 840 845

Phe Ser Leu Gly Leu Asn Pro Tyr Pro Gly Ile Leu Val Asn Ser Lys
850 855 860

Phe Tyr Lys Leu Val Lys Asp Gly Tyr Gln Met Ala Gln Pro Ala Phe
865 870 875 880

Ala Pro Lys Asn Ile Tyr Ser Ile Met Gln Ala Cys Trp Ala Leu Glu
885 890 895

Pro Thr His Arg Pro Thr Phe Gln Gln Ile Cys Ser Leu Leu Gln Glu
900 905 910

Gln Ala Gln Glu Asp Arg Arg Glu Arg Asp Tyr Thr Asn Leu Pro Ser
915 920 925

Ser Ser Arg Ser Gly Gly Ser Gly Ser Gly Ser Ser Ser Ser Ser Ser
930 935 940

Glu Pro Glu Glu Glu Ser Ser Glu His Leu Ala Cys Cys Glu Gln Gln
945 950 955 960

Gly Asp Ile Ala Gln Pro Leu Leu Gln Pro Asn Asn Tyr Gln Phe Cys
965 970 975